(12) United States Patent
Ying et al.

(10) Patent No.: US 12,325,741 B2
(45) Date of Patent: Jun. 10, 2025

(54) ANTI-Aβ ANTIBODIES AND ANTIGEN-BINDING FRAGMENTS THEREOF

(71) Applicants: Jiangsu Hengrui Medicine Co., Ltd., Lianyungang (CN); Shanghai Hengrui Pharmaceutical Co., Ltd., Shanghai (CN)

(72) Inventors: Hua Ying, Shanghai (CN); Ling Zhang, Shanghai (CN); Jinping Shi, Shanghai (CN); Xiaomin Zhang, Shanghai (CN); Jiakang Sun, Shanghai (CN); Qiyue Hu, Shanghai (CN); Weikang Tao, Shanghai (CN)

(73) Assignees: Jiangsu Hengrui Medicine Co., Ltd., Lianyungang (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 1180 days.

(21) Appl. No.: 17/259,425

(22) PCT Filed: Jul. 16, 2019

(86) PCT No.: PCT/CN2019/096159
§ 371 (c)(1),
(2) Date: Aug. 2, 2021

(87) PCT Pub. No.: WO2020/015637
PCT Pub. Date: Jan. 23, 2020

(65) Prior Publication Data
US 2021/0371506 A1    Dec. 2, 2021

(30) Foreign Application Priority Data

Jul. 17, 2018  (CN) .......................... 201810782196.2

(51) Int. Cl.
| | | |
|---|---|---|
| *A61K 39/00* | (2006.01) | |
| *A61K 39/395* | (2006.01) | |
| *A61K 49/00* | (2006.01) | |
| *A61K 49/16* | (2006.01) | |
| *A61P 25/28* | (2006.01) | |
| *C07K 16/00* | (2006.01) | |
| *C07K 16/18* | (2006.01) | |

(52) U.S. Cl.
CPC ............. *C07K 16/18* (2013.01); *A61P 25/28* (2018.01); *A61K 2039/505* (2013.01); *C07K 2317/24* (2013.01); *C07K 2317/565* (2013.01); *C07K 2317/567* (2013.01); *C07K 2317/92* (2013.01)

(58) Field of Classification Search
CPC ............. C07K 16/18; C07K 2317/24; C07K 2317/565; C07K 2317/56; C07K 2317/21; C07K 2317/76; C07K 2317/92; C07K 16/00; C07K 2317/55; C07K 2317/33; C07K 2317/51; C07K 2317/515; C07K 2317/54; C07K 2317/622; C07K 2317/569; C07K 2317/624; C07K 2317/626; C07K 14/4711; A61K 2039/505; A61K 39/395; A61K 39/0007; A61K 51/1018; A61K 38/1709; A61K 39/00; A61K 38/1716; A61P 25/28; A61P 25/00; G01N 33/6896; G01N 2800/2821; G01N 2333/4709; G01N 33/5058
See application file for complete search history.

(56) References Cited

U.S. PATENT DOCUMENTS

| | | | |
|---|---|---|---|
| 5,750,349 A | 5/1998 | Suzuki et al. | |
| 7,780,963 B2 * | 8/2010 | Acton .................... | A61P 25/00 530/387.3 |
| 7,906,625 B2 * | 3/2011 | Shen ...................... | A61P 25/00 435/254.2 |
| 10,662,239 B2 | 5/2020 | Groves et al. | |
| 2012/0082667 A1 | 4/2012 | Yokoseki et al. | |
| 2014/0050719 A1 | 2/2014 | Burbidge et al. | |
| 2016/0244514 A1 | 8/2016 | Pfeifer et al. | |
| 2019/0315886 A1 | 10/2019 | Ying et al. | |

FOREIGN PATENT DOCUMENTS

| | | | |
|---|---|---|---|
| CN | 101415729 A | 4/2009 | |
| CN | 105164156 A | 12/2015 | |
| WO | 1994017197 A1 | 8/1994 | |
| WO | 1998044955 A1 | 10/1998 | |
| WO | 2003016466 A2 | 2/2003 | |
| WO | 2003070760 A2 | 8/2003 | |
| WO | 2004071408 A2 | 8/2004 | |
| WO | 2004108895 A2 | 12/2004 | |
| WO | WO-2006055178 A2 * | 5/2006 | ........... A61K 39/395 |
| WO | WO-2006081171 A1 * | 8/2006 | ............. C07K 16/18 |
| WO | 2007108756 A1 | 9/2007 | |

(Continued)

OTHER PUBLICATIONS

Maccallum et al.,J. Mol. Biol., 1996; 262: 732-745.*

(Continued)

*Primary Examiner* — Chang-Yu Wang
(74) *Attorney, Agent, or Firm* — Taft Stettinius & Hollister LLP

(57) ABSTRACT

Murine, chimeric or humanized anti-Abeta antibody having a specific CDR region, an antigen-binding fragment thereof, a pharmaceutical composition thereof, and usage thereof. Use of a humanized anti-Abeta antibody for the preparation of drugs for the treatment of a disease or disorder (such as Alzheimer's disease) caused by amyloid beta protein.

10 Claims, 20 Drawing Sheets
Specification includes a Sequence Listing.

(56) References Cited

FOREIGN PATENT DOCUMENTS

| WO | 2008011348 A2 | 1/2008 | |
|---|---|---|---|
| WO | 2008081008 A1 | 7/2008 | |
| WO | WO-2009085200 A2 * | 7/2009 | ............. A61P 25/16 |
| WO | 2012051498 A2 | 4/2012 | |
| WO | 2017133673 A1 | 8/2017 | |
| WO | 2018014126 A1 | 1/2018 | |

OTHER PUBLICATIONS

Pascalis et al., The Journal of Immunology, 2002; 169: 3076-3084.*
Casset et al., BBRC, 2003; 307: 198-205.*
Vajdos et al., J. Mol. Biol. 2002; 320: 415-428.*
Holm et al., Mol. Immunol., 2007; 44: 1075-1084.*
Chen et al., J. Mol. Bio., 1999; 293: 865-881.*
Wu et al., J. Mol. Biol., 1999; 294:151-162.*
Burgess et al. J of Cell Bio. 1990, 111:2129-2138.*
Bowie et al. Science, 1990, 247:1306-1310.*
Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al., Proc. Natl. Acad. Sci. USA 1982 vol. 79: p. 1979.*
International Search Report; China National Intellectual Property Administration (ISA/CN); International Application No. PCT/CN2019/096159; Oct. 14, 2019; 14 pages.
Esther S. Oh, M.D. et al.; Maximizing the Potential of Plasma Amyloid-beta as a Diagnostic Biomarker for Alzheimer's Disease; Neuromolecular Med.; 2008; 21 pages; vol. 10, No. 3.
Donna M. Wilcock et al.; Deglycosylated Anti-Amyloid-B Antibodies Eliminate Cognitive Deficits and Reduce Parenchymal Amyloid with Minimal Vascular Consequences in Aged Amyloid Precursor Protein Transgenic Mice; The Journal of Neuroscience; May 17, 2006; 15 pages; vol. 26, No. 20.
Joseph W. Arndt et al.; Structural and Kinetic Basis for the Selectivity of Aducanumab for Aggregated Forms of Amyloid-B; Nature; Apr. 23, 2018; 12 pages; vol. 8.
Fuxiang Bao et al.; Isolation and Identification of a Human Single Chain Fv Antibody Against Amyloid-Beta 1-42 Soluble Oligomers from a Human Phage Display Library; Chin J Biotech; Aug. 25, 2009; 22 pages; vol. 25, No. 8.
Bernd Bohrmann et al.; Gantenerumab: A Novel Human Anti-AB Antibody Demonstrates Sustained Cerebral Amyloid-B Binding and Elicits Cell-Mediated Removal of Human Amyloid-B; Journal of Alzheimer's Disease; 2012; 21 pages; vol. 28.
Lin et al.; Research Progress of B-Amyloid Protein in Alzheimer's Disease; Medical Recapitulate; Zhuhai Campus of Zunyi Medical College, Zhuhai, China; 2009; 8 pages.
Supplementary Partial European Search Report; European Patent Office; European Application No. 19838355.6; Apr. 1, 2022; 11 pages.

* cited by examiner

ANTI-Aβ ANTIBODIES AND ANTIGEN-BINDING FRAGMENTS THEREOF

CROSS-REFERENCE TO RELATED APPLICATIONS

This application is a U.S. National Phase of International PCT Application No. PCT/CN2019/096159 filed Jul. 16, 2019, which claims priority to Chinese Patent Application Serial No. 201810782196.2 filed Jul. 17, 2018, the contents of each application are incorporated herein by reference in their entirety.

SEQUENCE LISTING

This application incorporates by reference the material in the ASCII text file titled Revised_Sequence_Listing.txt, which was created on Jul. 11, 2021 and is 84 KB.

FIELD OF THE INVENTION

The present disclosure belongs to the field of biotechnology. More particularly, the present disclosure relates to anti-β-amyloid antibodies and applications thereof.

BACKGROUND OF THE INVENTION

The descriptions herein only provide background information about the present invention, and do not necessarily constitute prior art.

β-amyloid (Amyloid-beta, amyloid-beta, Abeta, Aβ) is a polypeptide comprising 39-43 amino acids produced from amyloid precursor protein (APP) by β- and γ-secretase proteolysis. It can be produced by a variety of cells and is circulating in blood, cerebrospinal fluid and cerebral interstitial fluid. Most of β-amyloid bind to chaperone molecules, and a few exist in a free state. Aβ is neurotoxic. It cannot be metabolized by cells when its content increases. Instead, it will be accumulated in large amounts within the cells to form Aβ senile plaques, and consequently promote neuron damage or death. The most common subtypes of Aβ in human body are Aβ1-40 and Aβ1-42, of which Aβ1-42 is more toxic and easier to be aggregated to form the core of Aβ plaque and trigger neurotoxic effects ("Medical Review", 2009, 15 (23): 3575-3577).

Alzheimer's disease (Alzheimer disease, AD) was first discovered in 1906 by German psychiatrist and neurologist, Alzheimer Alois, and was named after his name. It is also known as senile dementia, and is a chronic neurodegenerative disease. The main clinical manifestations of AD include gradual memory loss, cognitive disorder, abnormal behavior, and social disorder. Studies have found that AD patients mainly have the following pathological features: senile plaques formed by aggregation of β-amyloid in the cerebral cortex and hippocampus, neurofibrillary tangles formed by abnormal aggregation of Tau protein, and decreased nerve cells in the cortex and hippocampus. The deposition of Aβ is not only related to degenerative changes of neurons, but also capable of activating a series of pathological events, including the activation of astrocytes and microglial cells, the destruction of the blood-brain barrier and the alterations in microcirculation, and the like. It is a major cause of neuronal degeneration around senile plaques in brain and death in AD patients (Oh, E. S., Troncoso, J. C. & Fangmark Tucker, S. M. Neuromol Med (2008) 10: 195).

The deposition of Aβ was not only found in the senile plaques of Alzheimer's disease, but also found in a large amount in other cerebral amyloid diseases, such as cerebral amyloid angiopathy (CAA, also named as Congophilic amyloid angiopathy). The deposition of Aβ found in CAA is mainly composed of the shorter form of Aβ (Aβ1-40), and it also involves small amount of Aβ1-42 (Wilcock et al., Journal of Neuroinflammation 1 (24):1-11 (2004)).

Based on the important role of Aβ in the pathogenesis of AD, and the toxicity of Aβ is dependent on its quantity, degree of aggregation and clearance rate, researchers continuously developed various methods to interfere with Aβ diseases, attempting to retard or block the progress of AD by reducing the production of Aβ, preventing Aβ accumulation and deposition and interfering with the toxicity of Aβ. A variety of antibodies against Aβ have been published, including Aducanumab (Biogen), Bapineuzumab (Janssen, Elan, Pfizer), Solanezumab (Eli Lilly), Gantenerumab (Hoffman-LaRoche), and the anti-Aβ antibodies disclosed in Patent Application Nos WO1994017197A1, WO1998044955A1, WO2003016466A3, WO2003070760A3, WO2004071408A3, WO2006081171A1, WO2007108756A1, WO2008011348A3, WO2008081008A1, WO2012051498A3 and so on. However, most of the antibodies were ended in failure, including Bapineuzumab and Solanezumab, which have been rendered great expectations but failed in Phase III clinical trial. Currently, only Aducanumab is still in Phase III clinical trial, and it is considered to be the only new anti-Aβ antibody having promise of being approved for AD treatment, however further clinical trial outcomes are still needed to confirm whether it is qualified for marketing.

Therefore, there is still an urgent need to develop anti-Abeta antibodies with new structure for the treatment of diseases or disorders caused by β-amyloid (such as AD).

SUMMARY OF THE INVENTION

The inventors developed anti-Abeta antibodies and antigen-binding fragment thereof with completely new structure after extensive experimental studies. The anti-Abeta antibodies and antigen-binding fragment thereof are capable of specifically binding to human Abeta with high affinity, and exhibit excellent efficiency. They are expected to be useful for the treatment or prevention of diseases or disorders caused by Abeta (for example, Alzheimer's disease).

In some embodiments, the present disclosure provides an anti-Abeta antibody or antigen-binding fragment thereof specifically binding to human Abeta, said antibody comprising at least one CDR region selected from the following amino acid sequences or having at least 85% sequence identity therewith:

(1) the amino acid sequence of the heavy chain HCDR1 region as shown in SEQ ID NO: 11, 17 or 23;
(2) the amino acid sequence of the heavy chain HCDR2 region as shown in SEQ ID NO: 12, 18, 24 or 52;
(3) the amino acid sequence of the heavy chain HCDR3 region as shown in SEQ ID NO: 13, 19, 25 or 27;
(4) the amino acid sequence of the light chain LCDR1 region as shown in SEQ ID NO: 14 or 20;
(5) the amino acid sequence of the light chain LCDR2 region as shown in SEQ ID NO: 15 or 21; and
(6) the amino acid sequence of the light chain LCDR3 region as shown in SEQ ID NO: 16, 22, 26 or 53.

For the amino acid sequence having at least 85% sequence identity as indicated above, it preferably has at least 86%, 87%, 88%, 89%, 90%, 91%, 92%, 93%, 94%, 95%, 96%, 97%, 98% or 99% sequence identity; more preferably, it has more than 90%, more than 95% or more than 99% sequence identity, most preferably, it has at least 95% sequence identity. The above-mentioned amino acid sequence having at least 85% sequence identity may be obtained by deletion, insertion or substitution of one or more amino acid(s).

In some embodiments, said anti-Abeta antibody binds to human Aβ1-42 fibrils and/or Aβ1-42 monomer with a dissociation equilibrium constant (KD) of about $10^{-7}$M or even less; preferably, binds to human Abeta with a dissociation equilibrium constant (KD) of less than about $10^{-8}$M, $10^{-9}$M, or $10^{-10}$M or even less. The KD value may be determined by Surface Plasma Resonance (SPR) technology in Biacore T200 instrument. Preferably, said human Abeta is Aβ1-42 fibrils and Aβ1-42 monomer.

In some preferred embodiments, said anti-Abeta antibody or antigen-binding fragment thereof comprises HCDR1-3 regions or LCDR1-3 regions as indicated in any one of the follows:

(i) the antibody heavy chain HCDR1, HCDR2 and HCDR3 regions as shown in the amino acid sequences of SEQ ID NOs: 11, 12 and 13, respectively;

(ii) the antibody heavy chain HCDR1, HCDR2 and HCDR3 regions as shown in the amino acid sequences of SEQ ID NOs: 17, 18 and 19, respectively;

(iii) the antibody heavy chain HCDR1, HCDR2 and HCDR3 regions as shown in the amino acid sequences of SEQ ID NOs: 23, 24 and 25, respectively;

(iv) the antibody heavy chain HCDR1, HCDR2 and HCDR3 regions as shown in the amino acid sequences of SEQ ID NOs: 17, 18 and 27, respectively;

(v) the antibody heavy chain HCDR1, HCDR2 and HCDR3 regions as shown in the amino acid sequences of SEQ ID NOs: 17, 52 and 19, respectively;

(vi) the antibody heavy chain HCDR1, HCDR2 and HCDR3 regions as shown in the amino acid sequences of SEQ ID NOs: 17, 52 and 27, respectively;

and/or (vii) the antibody light chain LCDR1, LCDR2 and LCDR3 regions as shown in the amino acid sequences of SEQ ID NOs: 14, 15 and 16, respectively;

(viii) the antibody light chain LCDR1, LCDR2 and LCDR3 regions as shown in the amino acid sequences of SEQ ID NOs: 20, 21 and 22, respectively;

(viiii) the antibody light chain LCDR1, LCDR2 and LCDR3 regions as shown in the amino acid sequences of SEQ ID NOs: 20, 21 and 26, respectively; or (x) the antibody light chain LCDR1, LCDR2 and LCDR3 regions as shown in the amino acid sequences of SEQ ID NOs: 20, 21 and 53, respectively.

In some embodiments, the anti-Abeta antibody or antigen-binding fragment thereof of the present disclosure is any anti-Abeta antibody or antigen-binding fragment thereof selected from the following A to D:

A) an anti-Abeta antibody or antigen-binding fragment thereof, having heavy chain HCDR1 region as shown in amino acid sequence SEQ ID NO: 11, heavy chain HCDR2 region as shown in amino acid sequence SEQ ID NO: 12 and heavy chain HCDR3 region as shown in amino acid sequence SEQ ID NO:13, and light chain LCDR1 region as shown in amino acid sequence SEQ ID NO: 14, light chain LCDR2 region as shown in amino acid sequence SEQ ID NO: 15 and light chain LCDR3 region as shown in amino acid sequence SEQ ID NO: 16;

B) an anti-Abeta antibody or antigen-binding fragment thereof, having heavy chain HCDR1 region as shown in amino acid sequence SEQ ID NO: 17, heavy chain HCDR2 region as shown in amino acid sequence SEQ ID NO: 18 or 52 and heavy chain HCDR3 region as shown in amino acid sequence SEQ ID NO:19, and light chain LCDR1 region as shown in amino acid sequence SEQ ID NO: 20, light chain LCDR2 region as shown in amino acid sequence SEQ ID NO: 21 and light chain LCDR3 region as shown in amino acid sequence SEQ ID NO: 22;

C) an anti-Abeta antibody or antigen-binding fragment thereof, having heavy chain HCDR1 region as shown in amino acid sequence SEQ ID NO: 23, heavy chain HCDR2 region as shown in amino acid sequence SEQ ID NO: 24 and heavy chain HCDR3 region as shown in amino acid sequence SEQ ID NO:25, and light chain LCDR1 region as shown in amino acid sequence SEQ ID NO: 20, light chain LCDR2 region as shown in amino acid sequence SEQ ID NO: 21 and light chain LCDR3 region as shown in amino acid sequence SEQ ID NO: 26 or 53; and D) an anti-Abeta antibody or antigen-binding fragment thereof, having heavy chain HCDR1 region as shown in amino acid sequence SEQ ID NO: 17, heavy chain HCDR2 region as shown in amino acid sequence SEQ ID NO: 18 or 52 and heavy chain HCDR3 region as shown in amino acid sequence SEQ ID NO:27, and light chain LCDR1 region as shown in amino acid sequence SEQ ID NO: 20, light chain LCDR2 region as shown in amino acid sequence SEQ ID NO: 21 and light chain LCDR3 region as shown in amino acid sequence SEQ ID NO: 22.

In some embodiments, said anti-Abeta antibody or antigen-binding fragment thereof is murine, chimeric, humanized, or fully human antibody.

In some embodiments, said anti-Abeta antibody or antigen-binding fragment thereof is murine antibody, and the heavy chain variable region amino acid sequence of the antibody is shown in SEQ ID NO: 3, 5, 7 or 9 or having at least 85% sequence identity therewith; and/or the light chain variable region amino acid sequence of the antibody is shown in SEQ ID NO:4, 6, 8 or 10 or having at least 85% sequence identity therewith.

For the amino acid sequence having at least 85% sequence identity as indicated above, it preferably has at least 86%, 87%, 88%, 89%, 90%, 91%, 92%, 93%, 94%, 95%, 96%, 97%, 98% or 99% sequence identity; more preferably, it has more than 90%, more than 95% or more than 99% sequence identity, most preferably, it has at least 95% sequence identity. The above-mentioned amino acid sequence having at least 85% sequence identity may be obtained by deletion, insertion or substitution of one or more amino acid(s). Preferably, said antibody binds to human Abeta with a dissociation equilibrium constant (KD) of about $10^{-7}$M or even less. In some embodiments, said antibody binds to human Abeta with a dissociation equilibrium constant (KD) of less than about $10^{-8}$M, $10^{-9}$M, or $10^{-10}$M or even less, and the KD value may be determined by Surface Plasma Resonance (SPR) technology in Biacore T200 instrument. Preferably, said human Abeta is Aβ1-42 fibrils and Aβ1-42 monomer.

In some embodiments, said anti-Abeta antibody or antigen-binding fragment thereof is any anti-Abeta antibody or antigen-binding fragment thereof selected from the following E to H:

E) an anti-Abeta antibody or antigen-binding fragment thereof, comprising a heavy chain variable region as shown in amino acid sequence SEQ ID NO: 3 and a light chain variable region as shown in amino acid sequence SEQ ID NO: 4;

F) an anti-Abeta antibody or antigen-binding fragment thereof, comprising a heavy chain variable region as shown in amino acid sequence SEQ ID NO: 5 and a light chain variable region as shown in amino acid sequence SEQ ID NO: 6;

G) an anti-Abeta antibody or antigen-binding fragment thereof, comprising a heavy chain variable region as shown in amino acid sequence SEQ ID NO: 7 and a light chain variable region as shown in amino acid sequence SEQ ID NO: 8; and H) an anti-Abeta antibody or antigen-binding fragment thereof, comprising a heavy chain variable region as shown in amino acid sequence SEQ ID NO: 9 and a light chain variable region as shown in amino acid sequence SEQ ID NO: 10.

In some embodiments of the above-mentioned anti-Abeta antibody or antigen-binding fragment thereof of the present disclosure, said antibody is humanized antibody. Preferably, the FR region sequence of the antibody is derived from human germline antibody FR region sequence or variant thereof. Preferably, as required, the variant includes one or more amino acid deletions, insertions or substitutions; More preferably, the FR region variant has up to 10 amino acid back mutation(s) on the light chain framework region and/or heavy chain framework region of a human antibody, respectively.

In some embodiments, the heavy chain variable region amino acid sequence of the anti-Abeta antibody or antigen-binding fragment thereof is shown in SEQ ID NO: 44, 46, 48 or 50, or having at least 85% sequence identity therewith; and/or the light chain variable region amino acid sequence of the antibody is shown in SEQ ID NO:45, 47, 49 or 51, or having at least 85% sequence identity therewith.

For the amino acid sequence having at least 85% sequence identity as indicated above, it preferably has at least 86%, 87%, 88%, 89%, 90%, 91%, 92%, 93%, 94%, 95%, 96%, 97%, 98% or 99% sequence identity; more preferably, it has more than 90%, more than 95% or more than 99% sequence identity, most preferably, it has at least 95% sequence identity. The above-mentioned amino acid sequence having at least 85% sequence identity may be obtained by deletion, insertion or substitution of one or more amino acid(s). Preferably, said antibody binds to human Abeta with a dissociation equilibrium constant (KD) of about $10^{-10}$M or even less. In some embodiments, said antibody binds to human Abeta with a dissociation equilibrium constant (KD) of less than about $10^{-8}$M, $10^{-9}$M, or $10^{-10}$ M or even less, and the KD value may be determined by Surface Plasma Resonance (SPR) technology in Biacore T200 instrument. Preferably, said human Abeta is Aβ1-42 fibrils and Aβ1-42 monomer.

In some embodiments, said antibody is humanized antibody selected from any anti-Abeta antibody or antigen-binding fragment thereof of the following a) to d):

a) an anti-Abeta antibody or antigen-binding fragment thereof, the heavy chain variable region of the antibody having at least 90% sequence identity to that as shown in SEQ ID NO: 44, and the light chain variable region of the antibody having at least 90% sequence identity to that as shown in SEQ ID NO: 45;

b) an anti-Abeta antibody or antigen-binding fragment thereof, the heavy chain variable region of the antibody having at least 90% sequence identity to that as shown in SEQ ID NO: 46, and the light chain variable region of the antibody having at least 90% sequence identity to that as shown in SEQ ID NO: 47;

c) an anti-Abeta antibody or antigen-binding fragment thereof, the heavy chain variable region of the antibody having at least 90% sequence identity to that as shown in SEQ ID NO: 48, and the light chain variable region of the antibody having at least 90% sequence identity to that as shown in SEQ ID NO: 49; and d) an anti-Abeta antibody or antigen-binding fragment thereof, the heavy chain variable region of the antibody having at least 90% sequence identity to that as shown in SEQ ID NO: 50, and the light chain variable region of the antibody having at least 90% sequence identity to that as shown in SEQ ID NO: 51, wherein the above-mentioned at least 90% sequence identity includes at least 90%, 91%, 92%, 93%, 94%, 95%, 96%, 97%, 98%, 99% or 100% sequence identity.

In some embodiments, said antibody is humanized antibody comprising variable regions as shown in any of the following:

a) an antibody heavy chain variable region comprising HCDR1, HCDR2 and HCDR3 as shown in SEQ ID NO: 11, SEQ ID NO: 12 and SEQ ID NO: 13, respectively, and FR region(s) comprising one or more amino acid back mutation(s) selected from the group consisting of 1E, 71A and 94R; and an antibody light chain variable region comprising LCDR1, LCDR2 and LCDR3 as shown in SEQ ID NO: 14, SEQ ID NO: 15 and SEQ ID NO: 16, respectively;

b) an antibody heavy chain variable region comprising HCDR1 and HCDR3 as shown in SEQ ID NO: 17 and SEQ ID NO: 19, respectively, and HCDR2 as shown in SEQ ID NO: 18 or 52, and FR region(s) comprising one or more amino acid back mutation(s) selected from the group consisting of 28A and 82B T; and an antibody light chain variable region comprising LCDR1, LCDR2 and LCDR3 as shown in SEQ ID NO: 20, SEQ ID NO: 21 and SEQ ID NO: 22, respectively;

c) an antibody heavy chain variable region comprising HCDR1, HCDR2 and HCDR3 as shown in SEQ ID NO: 23, SEQ ID NO: 24 and SEQ ID NO: 25, respectively; and an antibody light chain variable region comprising LCDR1 and LCDR2 as shown in SEQ ID NO: 20 and SEQ ID NO: 21, respectively, and LCDR3 as shown in SEQ ID NO: 26 or 53, and FR region(s) comprising one or more amino acid back mutation(s) selected from the group consisting of 2V and 45K; and d) an antibody heavy chain variable region comprising HCDR1 and HCDR3 as shown in SEQ ID NO: 17 and SEQ ID NO: 27, respectively, and HCDR2 as shown in SEQ ID NO: 18 or 52; and an antibody light chain variable region comprising LCDR1, LCDR2 and LCDR3 as shown in SEQ ID NO: 20, SEQ ID NO: 21 and SEQ ID NO: 22, respectively, and FR region(s) comprising amino acid back mutation of 2V.

In some embodiments, said antibody is humanized antibody comprising variable regions as shown in any of the following:

a) an antibody heavy chain variable region as shown in amino acid sequence SEQ ID NO: 66 or FR region variant thereof; and an antibody light chain variable region as shown in amino acid sequence SEQ ID NO: 67 or FR region variant thereof;

b) an antibody heavy chain variable region as shown in amino acid sequence SEQ ID NO: 68 or FR region variant thereof; and an antibody light chain variable region as shown in amino acid sequence SEQ ID NO: 69 or FR region variant thereof;

c) an antibody heavy chain variable region as shown in amino acid sequence SEQ ID NO: 70 or FR region variant thereof; and an antibody light chain variable region as shown in amino acid sequence SEQ ID NO: 71 or FR region variant thereof; and d) an antibody heavy chain variable region as shown in amino acid sequence SEQ ID NO: 72 or FR region variant thereof; and an antibody light chain variable region as shown in amino acid sequence SEQ ID NO: 73 or FR region variant thereof; wherein the FR region variant has up to 10 amino acid back mutation(s) separately on the light chain framework region and/or heavy chain framework region.

In some embodiments, the above-mentioned anti-Abeta antibody or antigen-binding fragment thereof of the present disclosure is any anti-Abeta antibody or antigen-binding fragment thereof selected from the following M to P:

M) an anti-Abeta antibody or antigen-binding fragment thereof, comprising a heavy chain variable region as shown in amino acid sequence SEQ ID NO: 44 and a light chain variable region as shown in amino acid sequence SEQ ID NO: 45;

N) an anti-Abeta antibody or antigen-binding fragment thereof, comprising a heavy chain variable region as shown in amino acid sequence SEQ ID NO: 46 and a light chain variable region as shown in amino acid sequence SEQ ID NO: 47;

O) an anti-Abeta antibody or antigen-binding fragment thereof, comprising a heavy chain variable region as shown in amino acid sequence SEQ ID NO: 48 and a light chain variable region as shown in amino acid sequence SEQ ID NO: 49;

P) an anti-Abeta antibody or antigen-binding fragment thereof, comprising a heavy chain variable region as shown in amino acid sequence SEQ ID NO: 50 and a light chain variable region as shown in amino acid sequence SEQ ID NO: 51.

In some embodiments, said anti-Abeta antibody or antigen-binding fragment thereof further comprises constant region.

In some embodiments, the antibody heavy chain constant region is human IgG1 constant region, preferably, the amino acid sequence of the antibody heavy chain constant region is as shown in SEQ ID NO: 42 or having at least 85% sequence identity therewith; and the antibody light chain constant region is selected from human kappa constant region, and most preferably, the amino acid sequence of the antibody light chain constant region is as shown in SEQ ID NO: 43 or having at least 85% sequence identity therewith.

For the amino acid sequence having at least 85% sequence identity as indicated above, it preferably has at least 86%, 87%, 88%, 89%, 90%, 91%, 92%, 93%, 94%, 95%, 96%, 97%, 98% or 99% sequence identity; more preferably, it has more than 90%, more than 95% or more than 99% sequence identity, most preferably, it has at least 95% sequence identity. The above-mentioned amino acid sequence having at least 85% sequence identity may be obtained by deletion, insertion or substitution of one or more amino acid(s).

In some embodiments, the heavy chain amino acid sequence of the anti-Abeta antibody is as shown in SEQ ID NO: 30, 34, 38 or 40, or having at least 85% sequence identity therewith, and/or the light chain amino acid sequence of the antibody is shown in SEQ ID NO:31, 35, 39 or 41, or having at least 85% sequence identity therewith.

For the amino acid sequence having at least 85% sequence identity as indicated above, it preferably has at least 86%, 87%, 88%, 89%, 90%, 91%, 92%, 93%, 94%, 95%, 96%, 97%, 98% or 99% sequence identity; more preferably, it has more than 90%, more than 95% or more than 99% sequence identity, most preferably, it has at least 95% sequence identity. The above-mentioned amino acid sequence having at least 85% sequence identity may be obtained by deletion, insertion or substitution of one or more amino acid(s). Preferably, said antibody binds to human Abeta with a dissociation equilibrium constant (KD) of about $10^{-7}$M or even less. In some embodiments, said antibody binds to human Abeta with a dissociation equilibrium constant (KD) of less than about $10^{-8}$M, $10^{-9}$M, or $10^{-10}$ M or even less, and the KD value may be determined by Surface Plasma Resonance (SPR) technology in Biacore T200 instrument. Preferably, said human Abeta is Aβ1-42 fibrils and Aβ1-42 monomer.

In some embodiments, said anti-Abeta antibody or antigen-binding fragment thereof is any anti-Abeta antibody or antigen-binding fragment thereof selected from the following Q to T:

Q) an anti-Abeta antibody or antigen-binding fragment thereof, comprising a heavy chain as shown in amino acid sequence SEQ ID NO: 30 and a light chain as shown in amino acid sequence SEQ ID NO: 31;

R) an anti-Abeta antibody or antigen-binding fragment thereof, comprising a heavy chain as shown in amino acid sequence SEQ ID NO: 34 and a light chain as shown in amino acid sequence SEQ ID NO: 35;

S) an anti-Abeta antibody or antigen-binding fragment thereof, comprising a heavy chain as shown in amino acid sequence SEQ ID NO: 38 and a light chain as shown in amino acid sequence SEQ ID NO: 39; and T) an anti-Abeta antibody or antigen-binding fragment thereof, comprising a heavy chain as shown in amino acid sequence SEQ ID NO: 40 and a light chain as shown in amino acid sequence SEQ ID NO: 41.

In some embodiments, the antigen-binding fragment of the present disclosure is selected from the group consisting of Fab, Fab', F(ab')2, scFv, diabody, dsFv and antigen-binding fragment of peptide comprising CDR.

In some embodiments, provided is an anti-Abeta antibody competing with the above-mentioned antibody or antigen-binding fragment thereof for binding to human Abeta, or competing with the above-mentioned antibody or antigen-binding fragment thereof for binding to the same Abeta antigen epitope.

In some embodiments, the present disclosure also provides a nucleic acid molecule encoding any anti-Abeta antibody or antigen-binding fragment thereof as described above.

In some embodiments, the nucleic acid molecule is any nucleic acid molecule selected from the following U to Z:

U) a nucleic acid molecule, which comprises nucleotide sequence as shown in SEQ ID NO: 52 or nucleotide sequence having at least 85% sequence identity therewith, and/or comprises nucleotide sequence as shown in SEQ ID NO:53 or nucleotide sequence having at least 85% sequence identity therewith;

V) a nucleic acid molecule, which comprises nucleotide sequence as shown in SEQ ID NO: 54 or nucleotide sequence having at least 85% sequence identity therewith, and/or comprises nucleotide sequence as shown in SEQ ID NO:55 or nucleotide sequence having at least 85% sequence identity therewith;

W) a nucleic acid molecule, which comprises nucleotide sequence as shown in SEQ ID NO: 56 or nucleotide sequence having at least 85% sequence identity therewith, and/or comprises nucleotide sequence as shown in SEQ ID NO:57 or nucleotide sequence having at least 85% sequence identity therewith; and Z) a nucleic acid molecule, which comprises nucleotide sequence as shown in SEQ ID NO: 58 or nucleotide sequence having at least 85% sequence identity therewith, and/or comprises nucleotide sequence as shown in SEQ ID NO:59 or nucleotide sequence having at least 85% sequence identity therewith.

In one aspect, the present disclosure also provides a recombinant vector, which comprises the above-mentioned nucleic acid molecule.

In one aspect, the present disclosure also provides a host cell obtained by transforming the above-mentioned recombinant vector; the host cell is selected from the group consisting of prokaryotic cells and eukaryotic cells, preferably eukaryotic cells, more preferably mammalian cells, including CHO (Chinese Hamster ovary cell line) and NS0 cells.

In another aspect, the present disclosure provides a method for preparing the above-mentioned anti-Abeta antibody or antigen-binding fragment thereof, including the steps of cultivating the above-mentioned host cell in culture medium, and then purifying and recovering the antibody.

In another aspect, the present disclosure also provides a pharmaceutical composition, comprising the above-mentioned anti-Abeta antibody or antigen-binding fragment thereof, and one or more pharmaceutically acceptable carrier (s), excipient(s) or diluent(s).

In another aspect, the present disclosure also provides use of the above-mentioned anti-Abeta antibody or antigen-binding fragment thereof or the above-mentioned pharmaceutical composition in the preparation of a medicament for the treatment or prevention of a disease or disorder caused by Abeta.

In another aspect, the present disclosure also provides a method for treating or preventing a disease or disorder caused by Abeta, comprising administering a therapeutically effective amount of the above-mentioned anti-Abeta antibody or antigen-binding fragment thereof or the above-mentioned pharmaceutical composition, to a patient having the disease or disorder.

In another aspect, the present disclosure also provides the above-mentioned anti-Abeta antibody or antigen-binding fragment thereof or the above-mentioned pharmaceutical composition for use as a medicament for the treatment of Abeta-mediated diseases or disorders.

In some embodiments, the above-mentioned disease or disorder is a neurodegenerative disease selected from the group consisting of Alzheimer's disease, mild cognitive disorder, frontotemporal dementia, Lewy body disease, Parkinson's disease, Pick's disease, Bevac's disease, Congophilic amyloid angiopathy, cerebral amyloid angiopathy, Down syndrome, multiple infarct dementia, Huntington's disease, Creutzfeldt-Jakob Disease, AIDS dementia syndrome, depression, anxiety disorder, phobia, Bell's palsy, epilepsy, encephalitis, multiple sclerosis, neuromuscular disorder, neurotumor disorder, brain tumor, neurovascular disorder due to stroke, neuroimmunity disorder, neuropathic otology disease, neurotrauma due to spinal cord injury, pain due to neuropathic pain, pediatric neuro and neuropsychiatric disorder, sleep disorder, Tourette's syndrome, mild cognitive disorder, vascular dementia, multiple infarct dementia, cystic fibrosis, Gaucher's disease and other dyskinesia and diseases of the central nervous system. In some embodiments, the disease is Alzheimer's disease.

In some embodiments, the present disclosure also provides a method for treating or preventing Alzheimer's disease, comprising administering to a patient a therapeutically effective amount of the above-mentioned anti-Abeta antibody or antigen-binding fragment thereof or the above-mentioned pharmaceutical composition.

The anti-Abeta antibodies or antigen-binding fragments thereof of the present disclosure exhibit good efficiency both in biochemical tests and in vivo pharmacodynamic assays. For example, in an affinity detection assay, the anti-Abeta antibodies of the present disclosure (HAB-2401, HAB-5101, HAB-3601 and HAB-9001) exhibit an affinity for A$\beta$1-42 fibrils of less than $10^{-8}$M, even less than $10^{-10}$M, and an affinity for A$\beta$1-42 monomer of less than $10^{-7}$M to $10^{-8}$M. Especially, antibody HAB-9001 exhibits an affinity nearly 100 times stronger than Aducanumab, currently known as the most excellent anti-Abeta antibody.

In addition, in an assay of the effect of antibodies on blocking the aggregation of A$\beta$1-42 monomers into A$\beta$1-42 fibrils, the results show that the antibodies HAB-2401, HAB-5101 and HAB-9001 of the present disclosure can effectively inhibit the aggregation of A$\beta$1-42 monomer into A$\beta$1-42 fibrils, whereas Aducanumab can not.

In a biochemical test, the results show that the anti-Abeta antibodies HAB-2401 and HAB-3601 of the present disclosure have effects on protecting rat primary neurons and can promote the phagocytosis of A$\beta$ fibrils by primary microglial cells.

In addition, in a pharmacodynamic assay in animal, the results show that the antibodies HAB-2401, HAB-5101 and HAB-9001 of the present disclosure can significantly improve the spatial memory and cognitive competence of 5×FAD Alzheimer's mice. Further, the antibodies of the present disclosure have lower impact on the release of cytokines (such as TNF$\alpha$, IFN-$\gamma$, IL1$\beta$, IL2, IL6, IL12p70, IL4, IL10, MCP-1 and KC) in brain tissue, when compared to the positive antibody Aducanumab, indicating that the antibodies of the present disclosure are controllable in terms of security risks. The anti-Abeta antibodies of the present disclosure are expected to be useful in the future for the treatment or prevention of diseases or disorders caused by Abeta (such as Alzheimer's disease).

DESCRIPTION OF THE DRAWINGS

FIG. 3 displays BV2 phagocytosis assay, showing the experimental results of anti-Abeta antibodies which promote phagocytosis of A$\beta$ fibrils by BV2 cells by;

Two way ANOVA: WT vs. Vehicle: #$p<0.05$; ###: $P<0.001$;
Amab vs Vehicle: ▼:$p<0.05$; ▼▼:$p<0.01$; ▼▼▼:$P<0.001$;
HAB-5101-Ch vs. Vehicle: ^:$p<0.05$;
HAB-2401-Ch vs. Vehicle: ♦:$p<0.05$; ♦♦:$p<0.01$;
HAB-9001-Ch vs. Vehicle: *:$p<0.05$; :$p<0.01$; *:$P<0.001$.

Figure 10A:
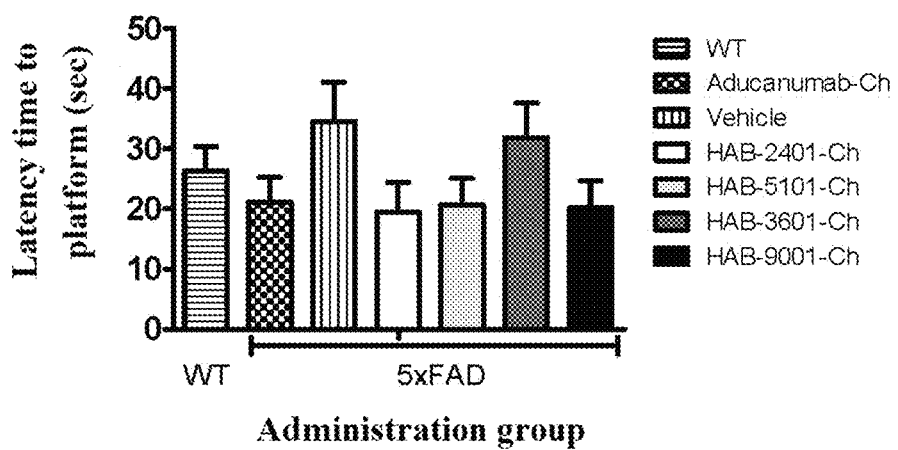
Figure 10B:
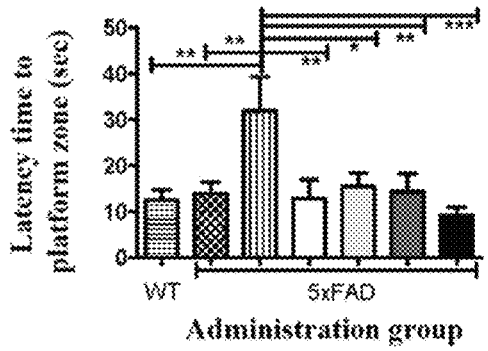
Figure 10C:
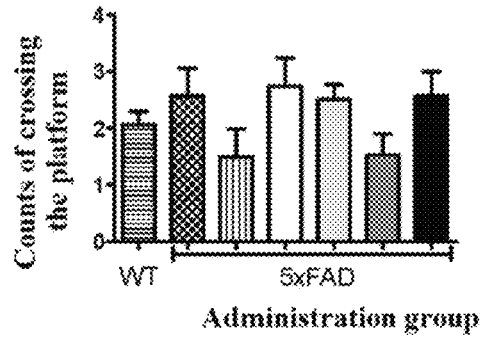
Figure 10D:
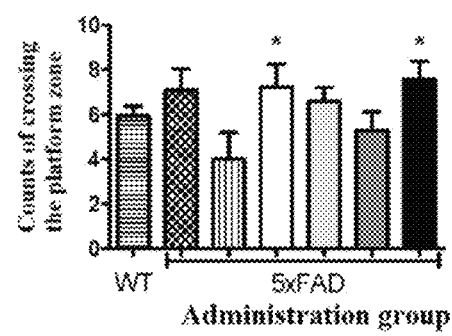
Figure 10E:
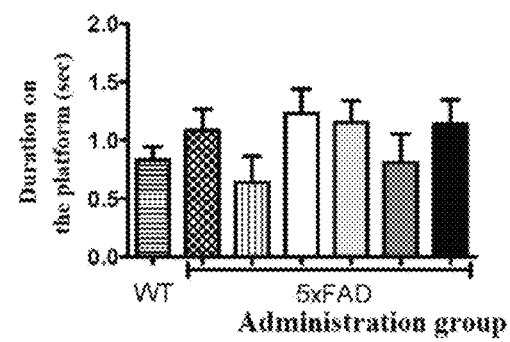
Figure 10F:
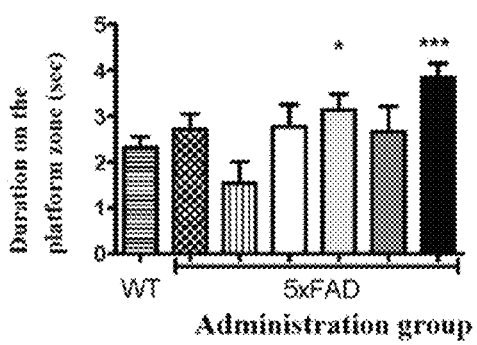
Figure 10G:
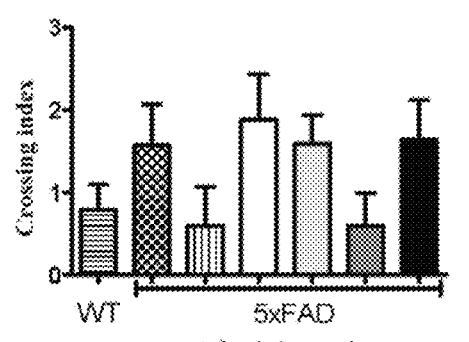
Figure 11A:
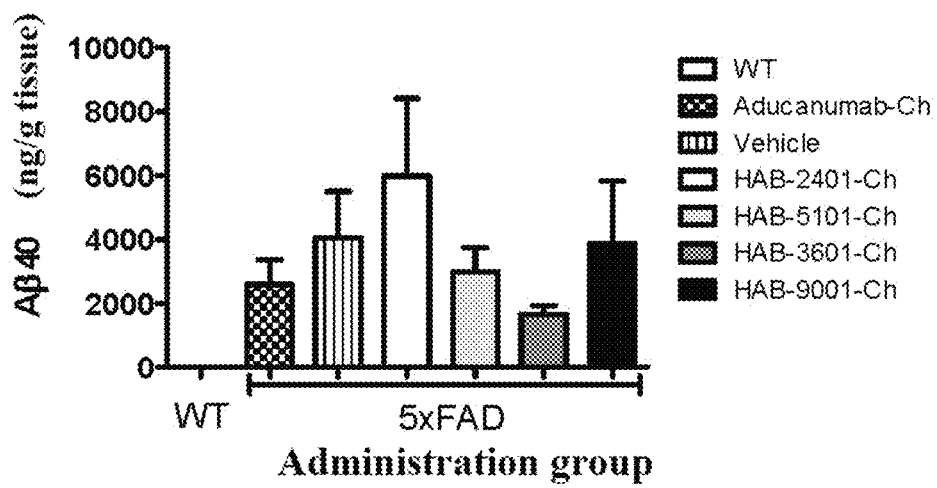
Figure 11B:
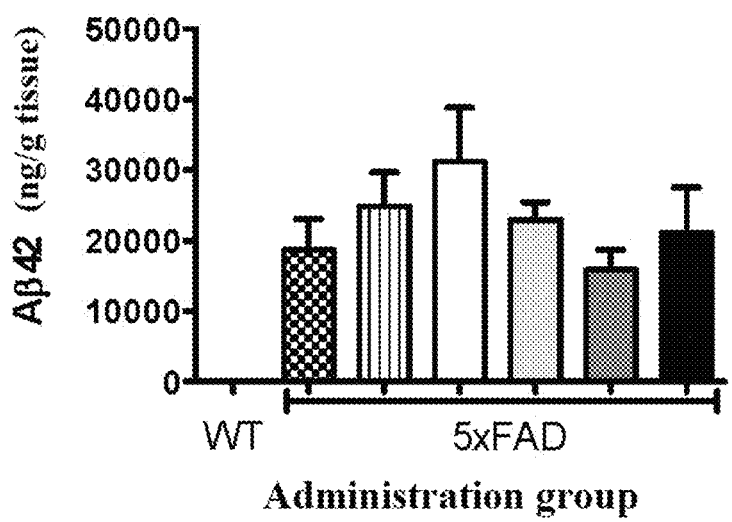
Figure 11C:
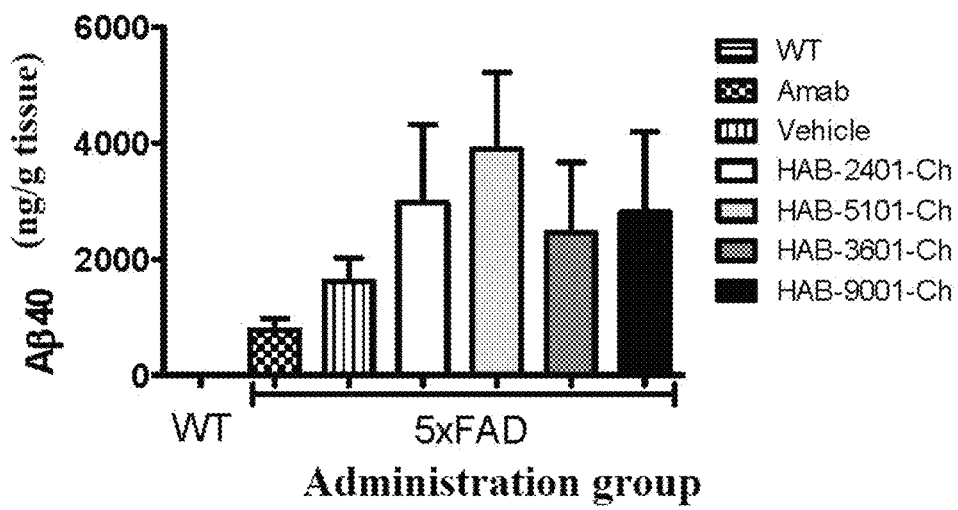
Figure 11D:
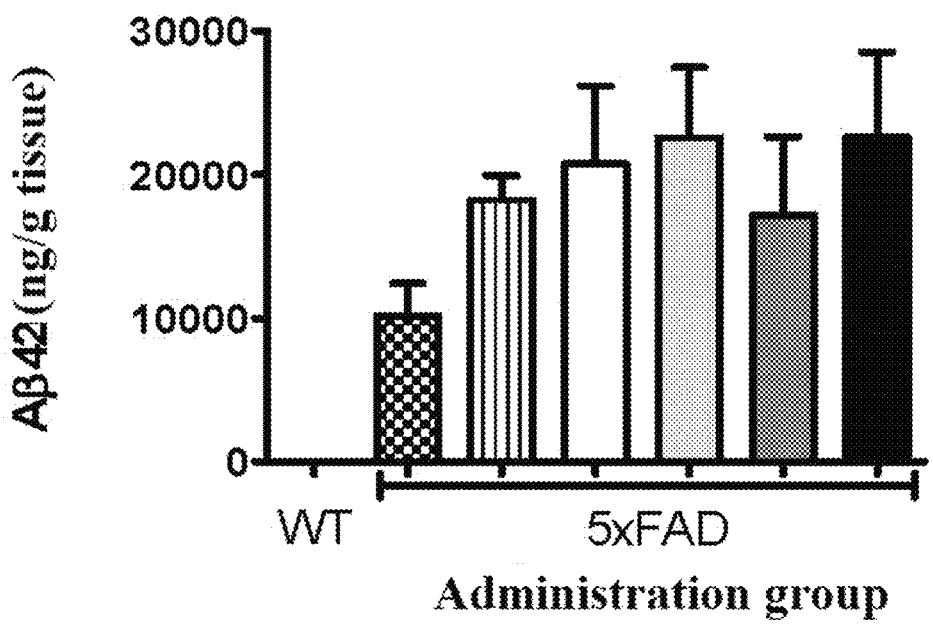
Figure 12:
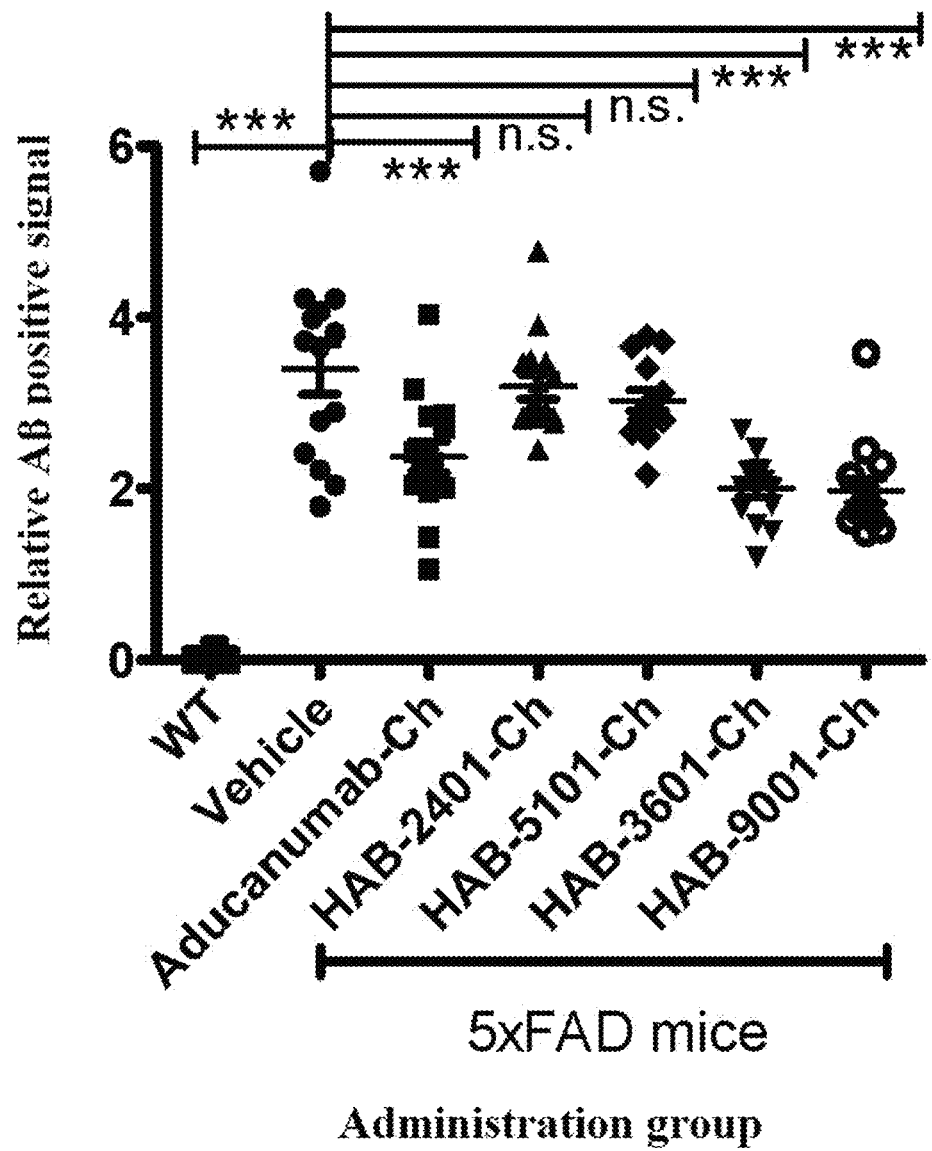
Figure 13:
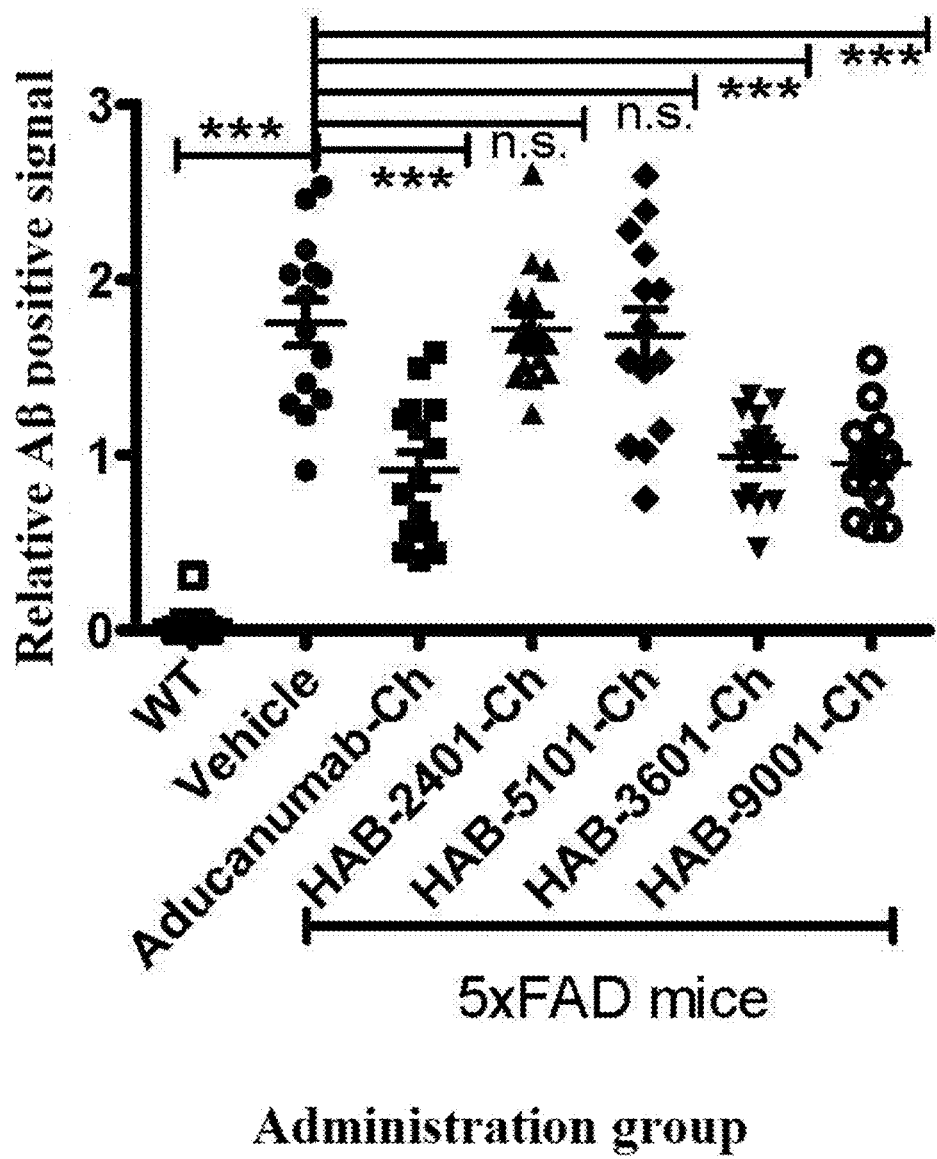
Figure 14A:
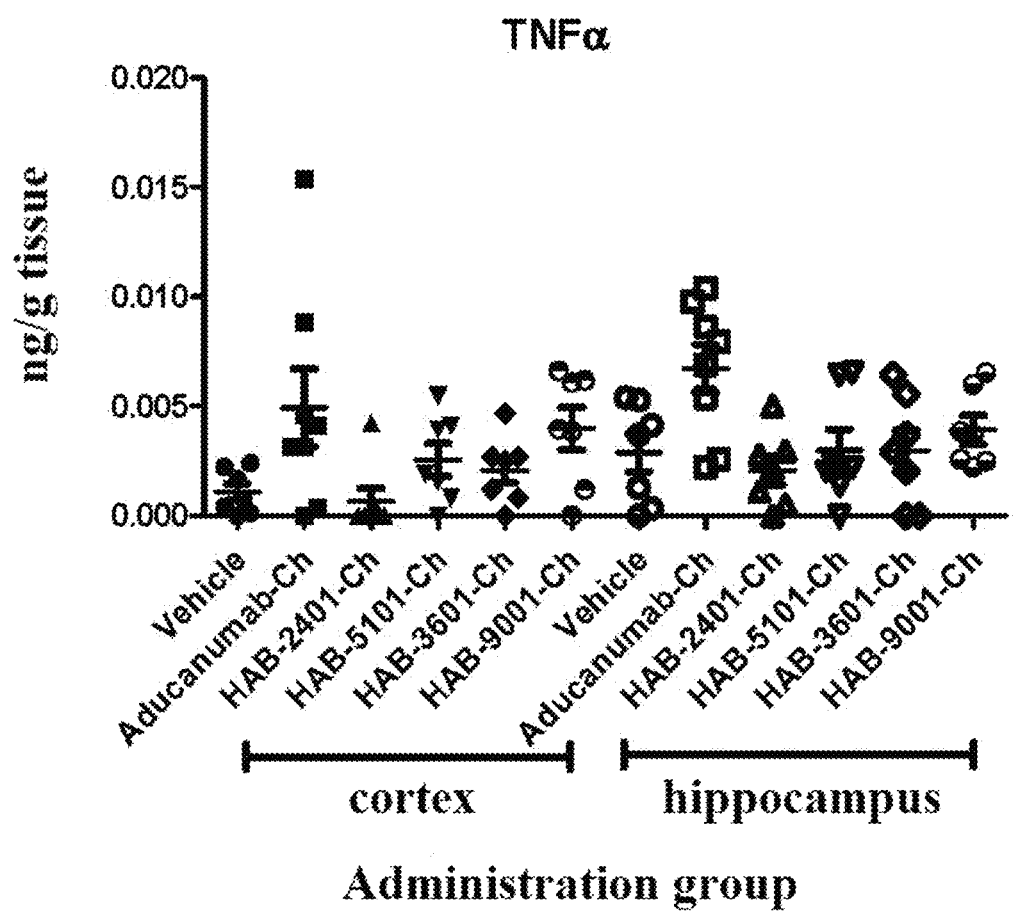
Figure 14B:
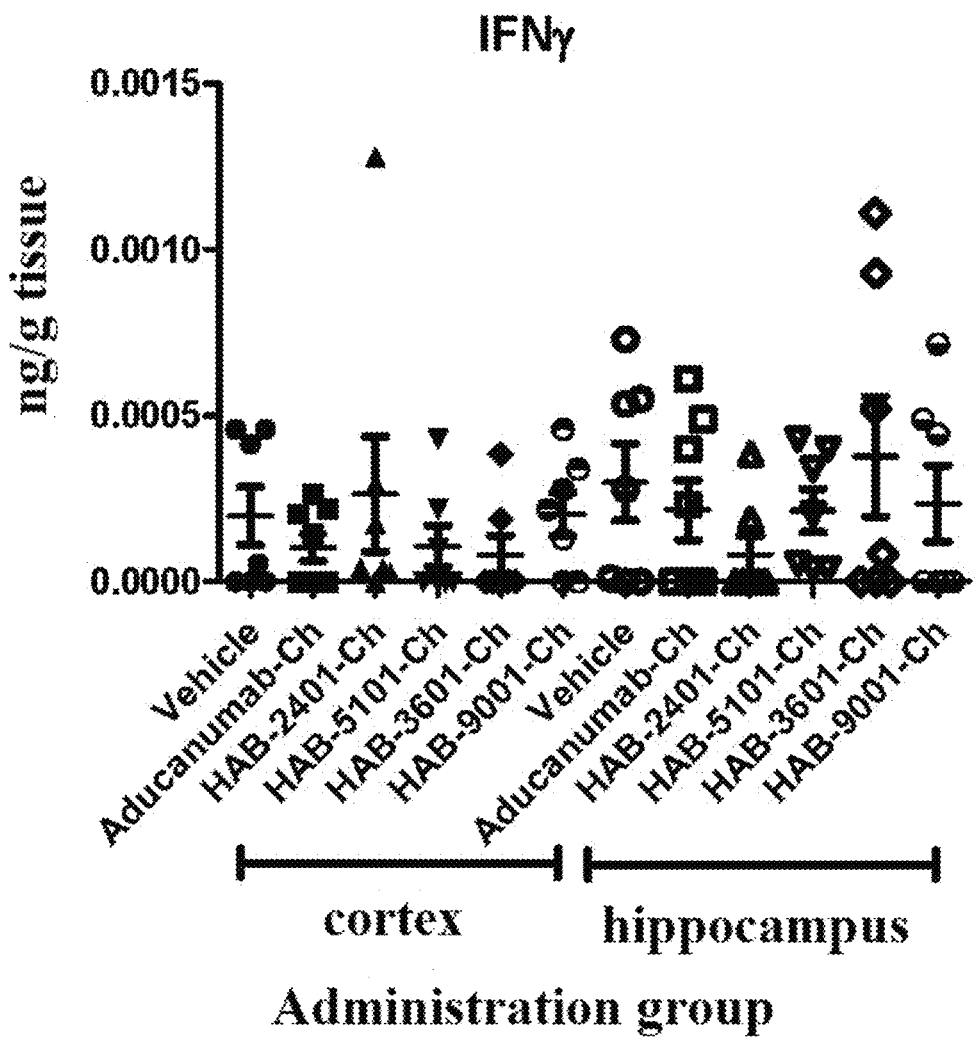
Figure 14C:
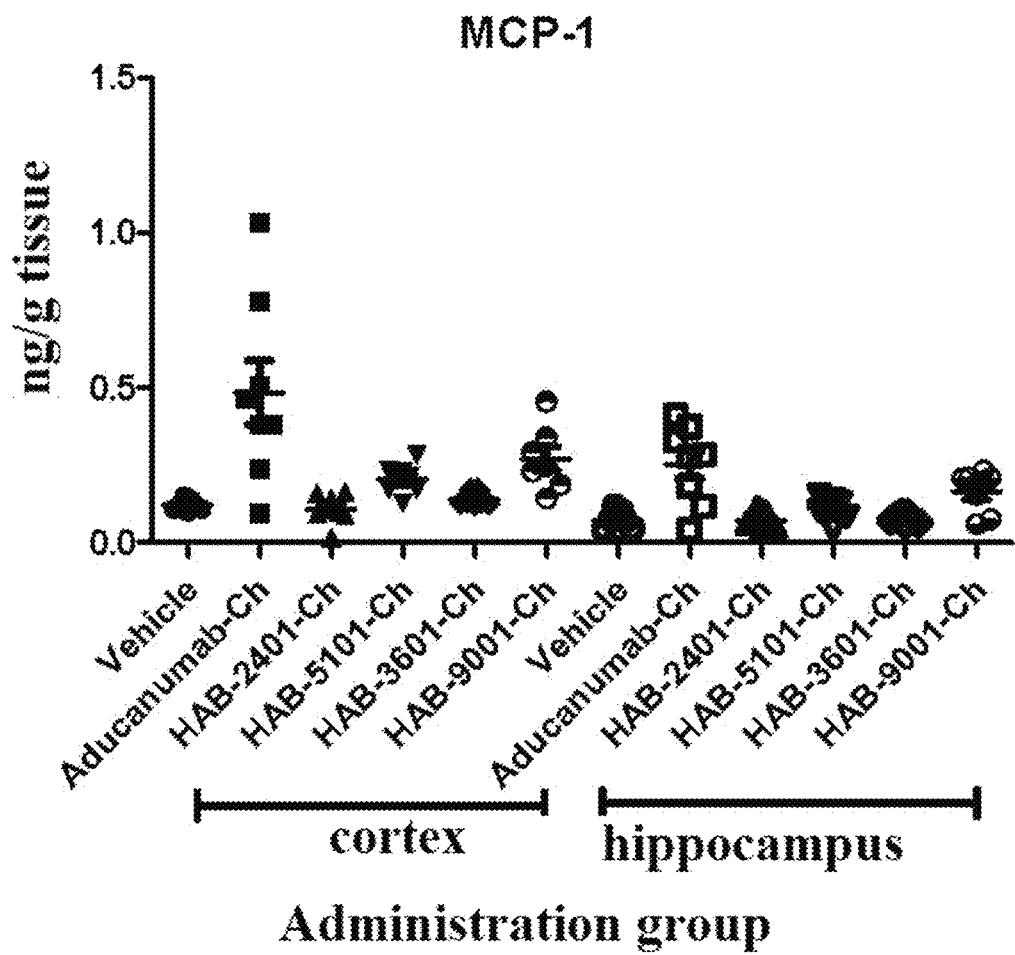
Figure 14D:
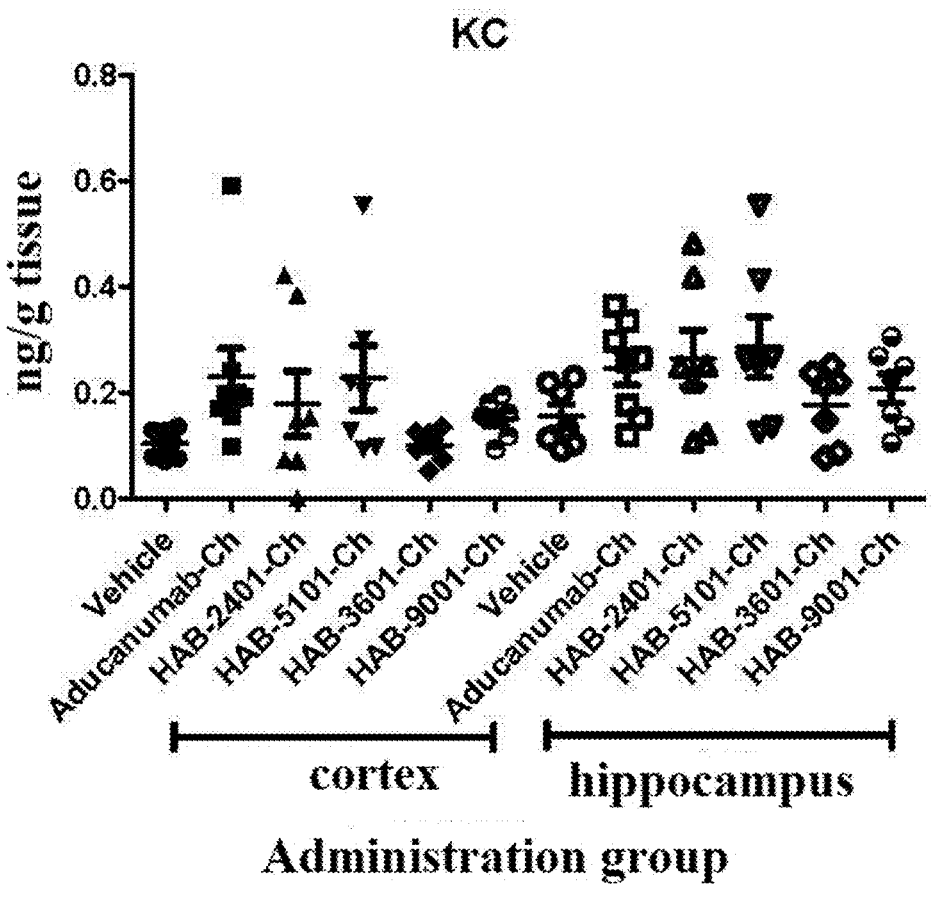
Figure 15A:
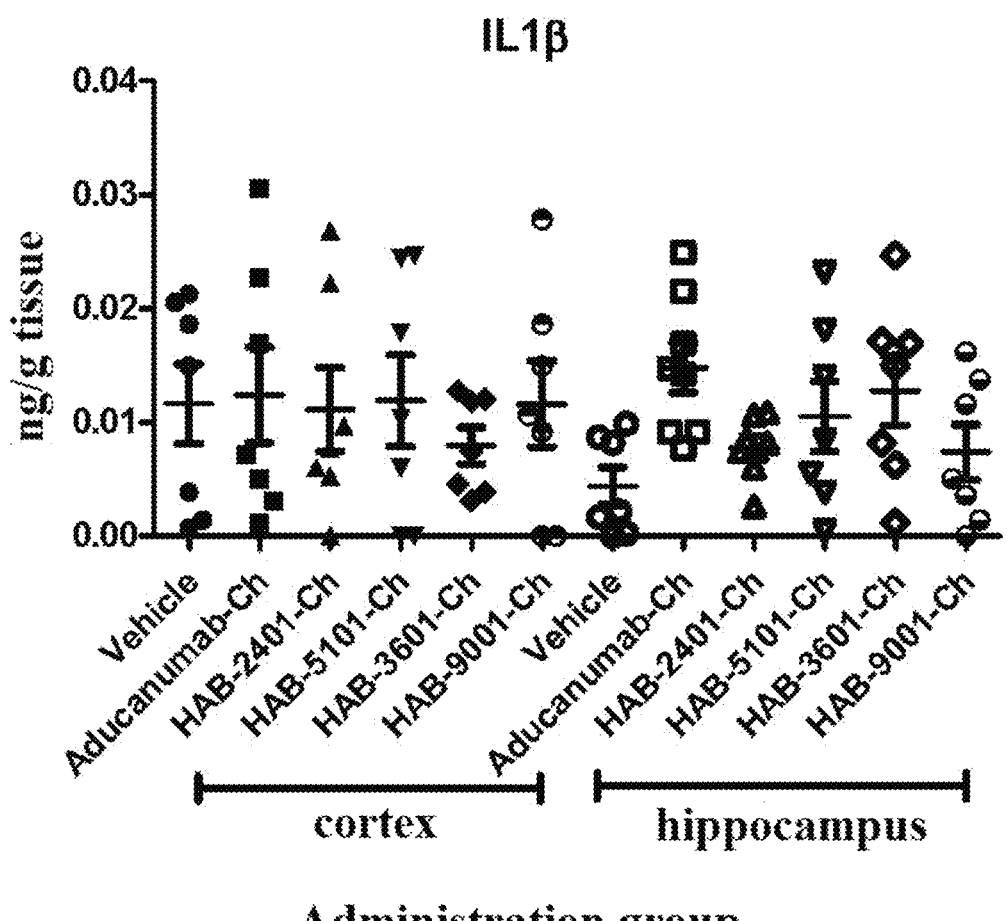
Figure 15B:
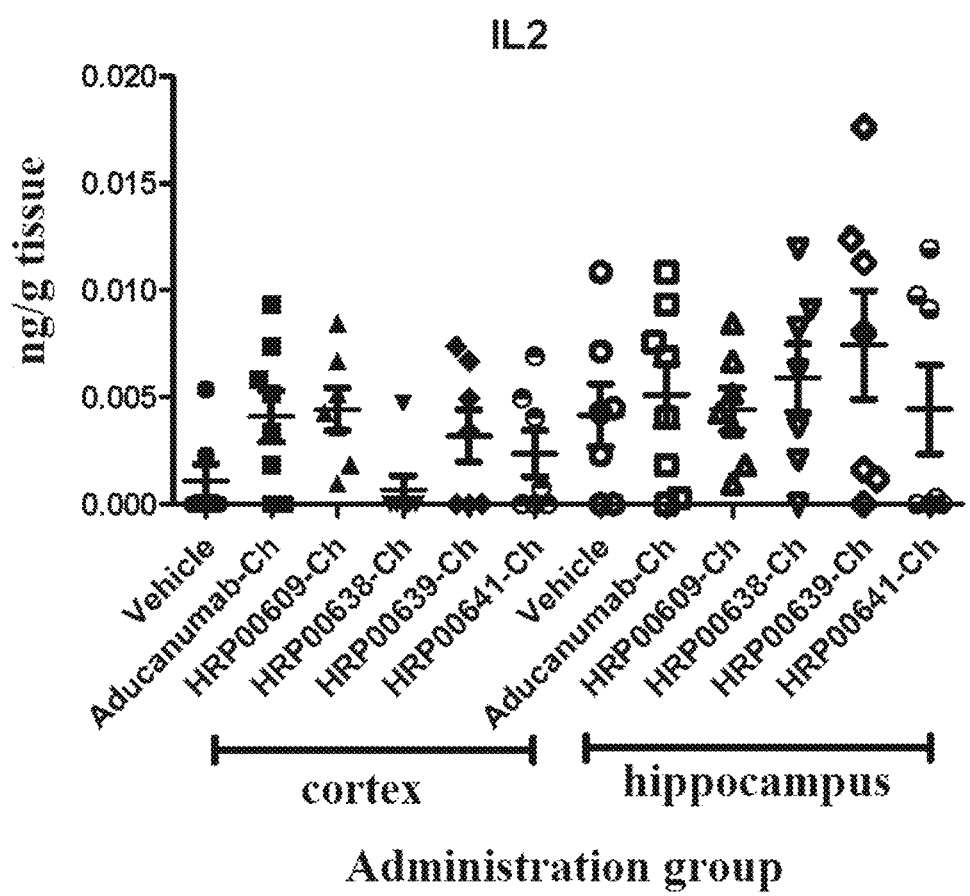
Figure 15C:
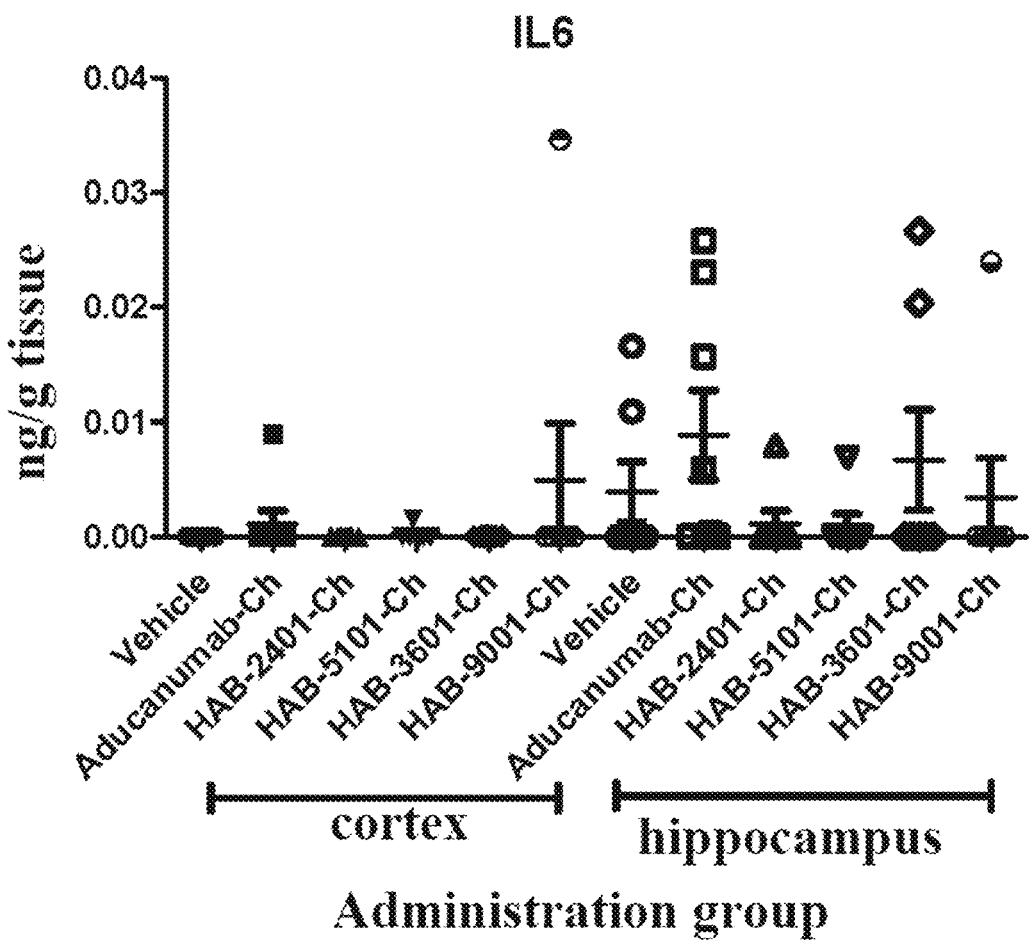
Figure 15D:
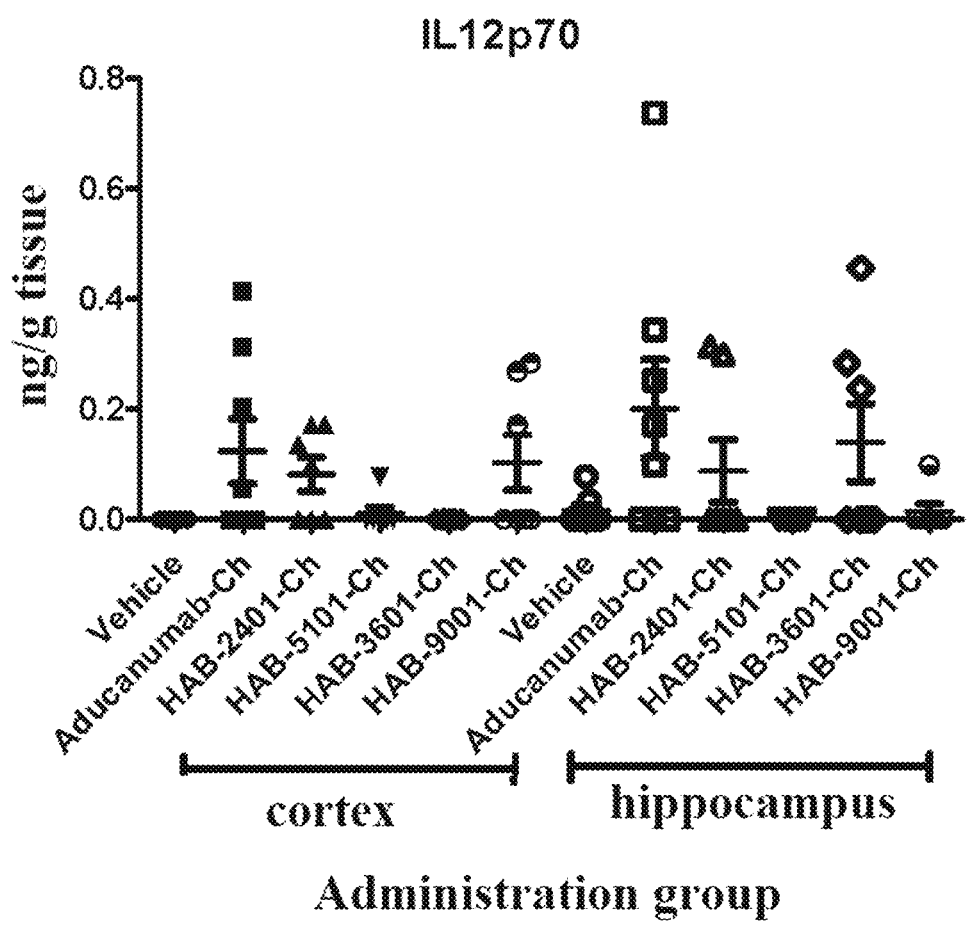
Figure 15E:
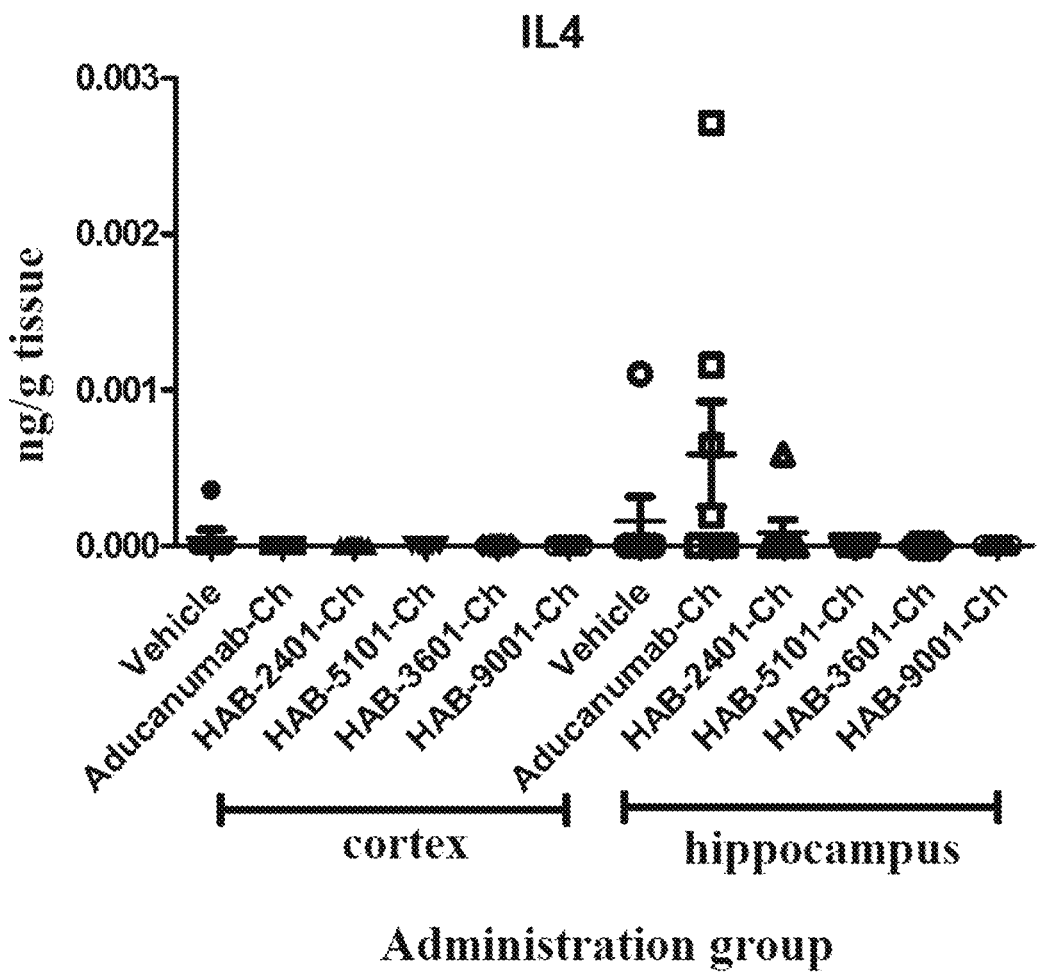
Figure 15F:
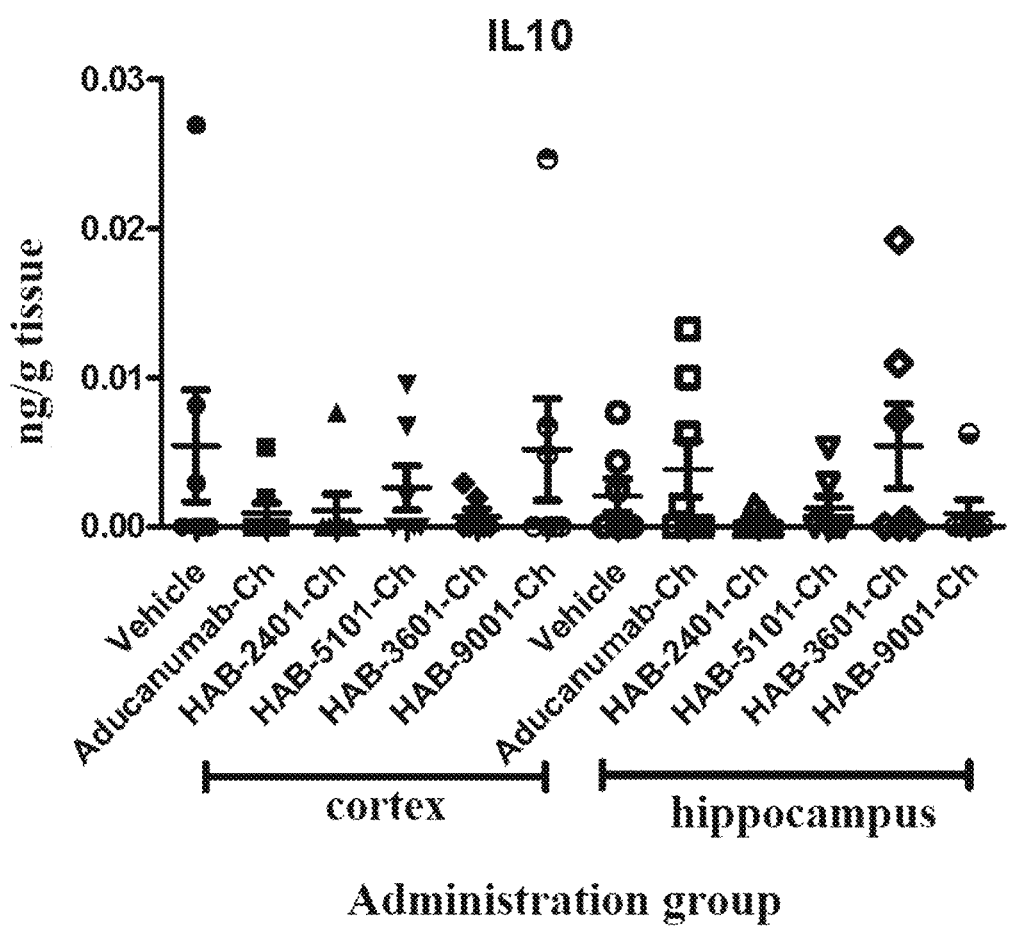

FIGS. 10A-10G display the results of the water maze experiment: the horizontal axis shows the drug administration groups; FIG. 10A shows the results of the latency time to arrive at the platform, FIG. 10B shows the results of the latency time to arrive at the platform zone, FIG. 10C shows the results of count of crossing the platform, FIG. 10D shows the results of count of crossing the platform zone, FIG. 10E shows the results of the duration on the platform, FIG. 10F shows the results of the duration at the platform zone, and FIG. 10G shows the results of the index crossing the platform (crossing index=the count for crossing the target region−(the sum of count for crossing the corresponding regions in the other three quadrants)/3), the legends of FIGS. 10B-10G are the same as those of FIG. 10A (see the legend in FIG. 10A for details). One way ANOVA refers to one-way analysis of variance (The same for FIGS. 12 and 13), v.s. vehicle, *$p<0.05$, $p<0.01$, *$p<0.001$; no significant differences were detected between the groups;

FIGS. 11A-11D display the results of Aβ deposition ELISA assay. FIG. 11A shows the content of insoluble Aβ1-40 present in the hippocampus, FIG. 11B shows the content of insoluble Aβ1-42 present in the hippocampus (the legend of FIG. 11B is the same as that of FIG. 11A, see FIG. 11A for details), FIG. 11C shows the content of insoluble Aβ31-40 present in the cortex, and FIG. 11D shows the content of insoluble Aβ31-42 present in the cortex (the legend of FIG. 11D is the same as that of FIG. 11C, see FIG. 11C for details);

FIG. 12 is a graph showing Aβ in the hippocampus, indicating the results of IHC detection of Aβ deposition (cortex). One way ANOVA, v.s. vehicle ***$p<0.001$;

FIG. 13 shows Aβ in the cortex, indicating the results of IHC detection of Aβ deposition (hippocampus);

FIG. 14A shows the effect of anti-Abeta antibodies on the release of cytokine, TNFα in brain tissue;

FIG. 14B shows the effect of anti-Abeta antibodies on the release of cytokine, IFN-γ in brain tissue;

FIG. 14C shows the effect of anti-Abeta antibodies on the release of MCP-1 in brain tissue;

FIG. 14D shows the effect of anti-Abeta antibodies on the release of KC in brain tissue;

FIG. 15A shows the effect of anti-Abeta antibodies on the release of cytokine, IL103 in brain tissue;

FIG. 15B shows the effect of anti-Abeta antibodies on the release of cytokine, IL2 in brain tissue;

FIG. 15C shows the effect of anti-Abeta antibodies on the release of cytokine, IL6 in brain tissue;

FIG. 15D shows the effect of anti-Abeta antibodies on the release of cytokine, IL12p70 in brain tissue;

FIG. 15E shows the effect of anti-Abeta antibodies on the release of cytokine, IL4 in brain tissue;

FIG. 15F shows the effect of anti-Abeta antibodies on the release of cytokine, IL10 in brain tissue.

TERMINOLOGY

In order to more easily understand the present disclosure, certain technical and scientific terms are specifically defined below. Unless otherwise defined explicitly herein, all other technical and scientific terms used herein have the meaning commonly understood by those skilled in the art to which this disclosure belongs.

Three-letter codes and one-letter codes for amino acids used in the present disclosure are as described in J. biol. chem, 243, p 3558 (1968).

In the present disclosure, "a XXX" refers to one or more of the substances; for example, "an anti-Abeta antibody" should be understood as one or more antibodies specifically binding to Abeta. Therefore, the terms "a", "one or more" and "at least one" may be used interchangeably herein.

The terms "amyloid β", "β-amyloid", "Aβ" and "Abeta" may be used interchangeably herein and refer to a segment generated by cleaving Amyloid Precursor Protein (APP) using β-secretase 1 (BACE1), or any modification or any functional equivalent thereof, including, but not limited to Aβ1-40 and Aβ1-42. It is known that Aβ is present in the form of monomers, which are combined to form oligomers and protofibril structure. The structure and sequences of such Aβ peptides are well-known to those skilled in the art, and methods for producing the peptides or for extracting the peptides from the brain and other tissues are also well-known (for example, Glenner and Wong, Biochem Biophys Res. Comm. 129:885-890 (1984)). Moreover, Aβ peptides are also commercially available. As examples of the amino acid sequence of human Aβ, SEQ ID NO:1 represents the amino acid sequence of Aβ1-40 and SEQ ID NO:2 represents the amino acid sequence of Aβ1-42.

As used herein, "antibody" refers to immunoglobulin, a four-peptide chain structure connected together by disulfide bond between two identical heavy chains and two identical light chains. Different immunoglobulin heavy chain constant region(s) exhibit different amino acid compositions and arrangement, hence present different antigenicity. Accordingly, immunoglobulins can be divided into five types, or named as immunoglobulin isotypes, namely IgM, IgD, IgQ IgA and IgE, corresponding to heavy chain μ, δ, γ, α and ε, respectively According to its amino acid composition of hinge region and the number and location of heavy chain disulfide bonds, the same type of Ig can further be divided into different sub-types, for example, IgG can be divided into IgG1, IgG2, IgG3 and IgG4. Light chain can be divided into κ or λ chain based on different constant region(s). Each of five types of Ig may has κ or λ chain.

In the present disclosure, the antibody light chain may further comprise light chain constant region, which comprises human or murine κ, λ chain or variant thereof; the antibody heavy chain may further comprise heavy chain constant region, which comprises human or murine IgG1, IgG 2, IgG 3, IgG 4 or variant thereof.

About 110 amino acid sequences adjacent to the N-terminus of the antibody heavy and light chains are highly variable, known as variable region (Fv region), including light chain variable region (VL) and heavy chain variable region (VH); the rest of amino acid sequences close to the C-terminus are relatively stable, known as constant region. The variable region includes three hypervariable regions (HVRs) and four relatively conserved framework regions (FRs). The three hypervariable regions which determine the specificity of the antibody are also known as complementarity determining regions (CDRs). Each light chain variable region (VL) and each heavy chain variable region (VH) consists of three CDR regions and four FR region(s), with sequential order from the amino terminus to carboxyl terminus in the following order: FR1, CDR1, FR2, CDR2, FR3, CDR3, and FR4. The three CDR regions of the light chain refer to LCDR1, LCDR2, and LCDR3, and the three CDR regions of the heavy chain refer to HCDR1, HCDR2, and HCDR3. The number and position of CDR amino acid residues of the antibody or antigen binding fragment described herein comply with known Kabat numbering criteria and/or Chothia numbering criteria ((1983) U.S. Dept. of Health and Human Services, "Sequence of Proteins of Immunological Interest).

Antibodies of the present disclosure include murine antibodies, chimeric antibodies, humanized antibodies, preferably humanized antibodies.

The term "murine antibody" described in the present disclosure refers to human Abeta-binding monoclonal antibody prepared according to the knowledge and skills of the field. During the preparation, test subject may be injected with Abeta antigen, and then a hybridoma expressing the antibody which possesses desired sequence or functional characteristics is isolated. In an embodiment of the present disclosure, the murine Abeta antibody or antigen binding fragment thereof further comprises light chain constant region of murine κ, λ chain or variant thereof, and/or further comprises heavy chain constant region of murine IgG1, IgG2, IgG3 or variant thereof.

The term "chimeric antibody" as described herein, is an antibody by fusing the variable region of murine antibody together with the constant region of human antibody, and the chimeric antibody can alleviate the murine antibody-induced immune response. To establish a chimeric antibody, first, a hybridoma secreting specific murine monoclonal antibody is established and variable region gene is cloned from the murine hybridoma. Then constant region gene is cloned from human antibody according to the need. The murine variable region gene is connected to the human constant region gene to form a chimeric gene, which can be subsequently inserted into an expression vector. Finally the chimeric antibody molecule will be expressed in eukaryotic or prokaryotic system. In an embodiment of the present disclosure, the light chain of the chimeric antibody further comprises a light chain constant region derived from human κ, λ chain or variant thereof. The heavy chain of the chimeric antibody further comprises a heavy chain constant region derived from human IgG1, IgG2, IgG3, IgG4 or variant thereof, preferably comprises a heavy chain constant region derived from human IgG1, IgG2 or IgG4, or IgG1, IgG2 or IgG4 variant with amino acid mutation(s), such as YTE mutation(s) or back-mutation(s).

The "humanized antibody" as used herein, also known as CDR-grafted antibody, refers to an antibody generated by grafting murine CDR sequences into human antibody variable region frameworks, i.e., an antibody produced in different types of human germline antibody framework sequences. Humanized antibody can conquer heterologous responses induced by chimeric antibody which carries a large number of murine protein components. Such framework sequences can be obtained from public DNA database covering germline antibody gene sequences or published references. For example, germline DNA sequences of human heavy and light chain variable region genes can be found in "VBase" human germline sequence database (www.mrccpe.com.ac.uk/vbase), as well as in Kabat, E A, et al. 1991 Sequences of Proteins of Immunological Interest, 5th Ed. To avoid a decrease in activity caused by the decreased immunogenicity, the framework sequences in human antibody variable region may be subjected to minimal reverse mutations or back mutation(s) to maintain the activity. The humanized antibody of the present disclosure also comprises humanized antibody on which CDR affinity maturation is performed by phage display. In one embodiment of the present disclosure, the CDR sequence of the Abeta humanized antibody is selected from SEQ ID NO: 11-27. For the human antibody variable region framework, after designing and selection, the antibody heavy chain FR region sequence is selected from FR1, FR2, FR3 and JH6 regions of human germline IGHV1-24*01 and hjh6.3, IGHV3-30*01 and hjh6.3 or IGHV2-70D*04 and hjh6.1, or mutant sequence thereof; the light chain FR region sequence is selected from FR1, FR2, FR3 and JK4, JK2 regions of the human germline IGKV1-27*01 and hjk4.1, IGKV1-39*01 and hjk4.1, IGKV2-40*01 and hjk4.1, IGKV2-40*01 and hjk2.1, or mutant sequence thereof.

The grafting of CDR can result in the decrease of the affinity of the resulting Abeta antibody or antigen binding fragment thereof to the antigen due to the framework residues contacted with the antigen. Such interactions may be resulted from highly somatic mutations. Therefore, it may still be necessary to graft the donor framework amino acids to the humanized antibody framework. The amino acid residues involved in antigen binding derived from non-human Abeta antibody or antigen binding fragment thereof can be identified by checking the sequence and structure of murine monoclonal antibody variable region. The amino acid residues which are different between the donor CDR framework and the germ lines may be considered to be related. If it is not possible to determine the most closely related germ line, the sequence may be compared to the common sequence shared by subtypes or the murine sequence with high similarity percentage. Rare framework residues are thought to be the result of a high mutation in somatic cells, and play an important role in binding.

As used herein, "antigen-binding fragment" or "functional fragment" refers to one or more fragments of antibody retaining the binding ability to the antigen. It has been shown that fragments of a full-length antibody can be used to achieve function of binding to a specific antigen. Examples of binding fragments included in the term "antigen binding fragment" include (i) Fab fragment, a monovalent fragment composed of VL, VH, CL and CH1 domain; (ii) F(ab')2 fragment, a bivalent fragment comprising two Fab fragments linked by a disulfide bond in hinge region; (iii) Fd fragment, consisting of VH and CH1 domains; (iv) Fv fragment, consisting of one-arm VH and VL domains; (v) single domain or dAb fragment (Ward et al. (1989) Nature 341: 544-546) composed of VH domain; and (vi) separate complementary determining region (CDR) or (vii) combination of two or more separate CDRs optionally linked by a synthetic linker. In addition, the VL domain and VH domain of the Fv fragment are encoded by two separate genes, however, they can be linked by a synthetic linker by using recombinant methods, to generate a single protein chain in which a monovalent molecular is formed by pairing the VL and VH domain (referred to as single chain Fv (scFv); see, e.g., Bird et al. (1988): 423-426; Science 242 and Huston et al (1988) Proc. Natl. Acad. Sci USA 85:5879-5883). Such single chain antibodies are also intended to be included in the term "antigen binding fragment". Such antibodies are obtained using conventional techniques known in the field, and screened for functional fragments by using the same method as that for an intact antibody. Antigen binding portions can be produced by recombinant DNA technology or by enzymatic or chemical disruption of an intact immunoglobulin. Antibodies can be in the form of different isotypes, e.g., IgG (e.g., IgG1, IgG2, IgG3 or IgG4 subtype), IgA1, IgA2, IgD, IgE or IgM antibody.

As used herein, Fab is an antibody fragment obtained by treating an IgG antibody molecule with a papain (which cleaves the amino acid residue at position 224 of the H chain). The Fab fragment has a molecular weight of about 50,000 and has antigen binding activity, in which about a half of the N-terminal side of H chain and the entire L chain are bound together through a disulfide bond. The Fab of the present disclosure can be produced by treating the monoclonal antibody of the present invention (which specifically recognizes human Abeta and binds to the extracellular region or three-dimensional structure thereof) with papain. Further, the Fab can be produced by inserting DNA encoding Fab of the antibody into a prokaryotic expression vector or eukaryotic expression vector and introducing the vector into a prokaryote or eukaryote to express the Fab.

As used herein, F(ab')2 is an antibody fragment having molecular weight of about 100,000 and having antigen binding activity and comprising two Fab regions which are bound at the hinge position, it may be produced by digesting the part downstream the two disulfide bonds in the hinge region of IgG with pepsin. The F(ab') 2 of the present disclosure can be produced by treating the monoclonal antibody of the present invention (which specifically recognizes Abeta and binds to the extracellular region or three-dimensional structure thereof) with pepsin. Also, the F(ab')2 can be produced by binding the Fab' described below via thioether bond or disulfide bond.

As used herein, Fab' is an antibody fragment having a molecular weight of about 50,000 and having antigen binding activity. Fab' is obtained by cleaving a disulfide bond at the hinge region of the above-mentioned F(ab')2 The Fab' of the present disclosure can be produced by treating the F(ab')2 of the present disclosure (which specifically recognizes Abeta and binds to the extracellular region or three-dimensional structure thereof) with a reducing agent, such as dithiothreitol. Further, the Fab' can be produced by inserting DNA encoding Fab' of the antibody into a prokaryotic expression vector or eukaryotic expression vector and introducing the vector into a prokaryote or eukaryote to express the Fab'.

As used herein, "single chain antibody", "single chain Fv" or "scFv" refers to a molecule comprising antibody heavy chain variable domain (or region; VH) connected to antibody light chain variable domain (or region; VL) by a linker. Such scFv molecules have general structure of NH2-VL-linker-VH-COOH or NH2-VH-linker-VL-COOH. A suitable linker in the prior art consists of repeated GGGGS amino acid sequence or variant thereof, for example, variant with 1-4 repeats (Holliger et al. (1993), Proc. Natl. Acad. Sci. USA 90: 6444-6448). Other linkers that can be used in the present disclosure are described by Alfthan et al. (1995), Protein Eng. 8:725-731, Choi et al. (2001), Eur. J. Immunol. 31:94-106, Hu et al. (1996), Cancer Res. 56:3055-3061, Kipriyanov et al. (1999), J. Mol. Biol. 293:41-56 and Roovers et al. (2001), Cancer Immunol. The scFv of the present disclosure can be produced by the following steps: obtaining cDNAs encoding VH and VL of the monoclonal antibody of the present disclosure which specifically recognizes human Abeta and binds to the extracellular region or three-dimensional structure thereof, constructing DNA encoding scFv, inserting the DNA into a prokaryotic expression vector or eukaryotic expression vector, and then introducing the expression vector into a prokaryote or eukaryote to express the scFv.

As used herein, diabody is an antibody fragment wherein the scFv is dimerized, and it is an antibody fragment having divalent antigen binding activity. In the divalent antigen binding activity, the two antigens may be the same or different. The diabody of the present disclosure can be produced by the following steps: obtaining cDNAs encoding VH and VL of the monoclonal antibody of the present disclosure which specifically recognizes human Abeta and binds to the extracellular region or three-dimensional structure thereof, constructing DNA encoding scFv so that the length of the linker peptide is 8 amino acid residues or less, inserting the DNA into a prokaryotic expression vector or eukaryotic expression vector, and then introducing the expression vector into a prokaryote or eukaryote to express the diabody.

As used herein, dsFv is obtained by replacing one amino acid residue in each of VH and VL with cysteine residue, and then connecting the substituted polypeptides via a disulfide bond between the two cysteine residues. The amino acid residues to be replaced with a cysteine residue can be selected based on three-dimensional structure prediction of the antibody in accordance with known methods (Protein Engineering, 7, 697 (1994)). The dsFv of the present disclosure can be produced by the following steps: obtaining cDNAs encoding VH and VL of the monoclonal antibody of the present disclosure which specifically recognizes human Abeta and binds to the extracellular region or three-dimensional structure thereof, constructing DNA encoding dsFv, inserting the DNA into a prokaryotic expression vector or eukaryotic expression vector, and then introducing the expression vector into a prokaryote or eukaryote to express the dsFv.

As used herein, CDR-containing peptide is constructed from one or more regions of VH or VL CDR. Peptides comprising several CDRs can be connected directly or via suitable peptide linker. The CDR-containing peptide of the present disclosure can be produced by the following steps: constructing DNA encoding VH and VL of the monoclonal antibody of the present disclosure which specifically recognizes human Abeta and binds to the extracellular region or three-dimensional structure thereof, inserting the DNA into a prokaryotic expression vector or eukaryotic expression vector, and then introducing the expression vector into a prokaryote or eukaryote to express the peptide. The CDR-containing peptide can also be produced by a chemical synthesis method such as Fmoc method or tBoc method.

As used herein, "CDR" refers to one of the six hypervariable regions present in the antibody variable domain that mainly contribute to antigen binding. One of the most commonly used definitions of the 6 CDRs is provided by Kabat E A et al. ((1991) Sequences of proteins of immunological interest. NIH Publication 91-3242). As used herein, Kabat definition for CDR is applied to CDR1, CDR2, and CDR3 of the light chain variable domain (CDR L1, CDR L2, CDR L3 or L1, L2, L3), and CDR2 and CDR3 of the heavy chain variable domain (CDR H2, CDR H3 or H2, H3).

As used herein, "antibody framework" refers to a part of the variable domain, either VL or VH, which serves as a scaffold for the antigen binding loops (CDRs) of this variable domain. Essentially, it is a variable domain without CDRs.

As used herein, "epitope" or "antigenic determinant" or "antigen epitope" refers to a site on an antigen to which an immunoglobulin or antibody specifically binds (e.g., a specific site on Abeta molecule). Epitopes typically include at least 3, 4, 5, 6, 7, 8, 9, 10, 11, 12, 13, 14 or 15 contiguous or non-contiguous amino acids in a unique tertiary conformation. (See, Epitope Mapping Protocols in Methods in Molecular Biology, Vol. 66, ed. G E. Morris (1996)).

As used herein, "specifically bind to", "selectively bind to", "selectively binds to" or "specifically binds to" refers to the binding of an antibody to a predetermined epitope on an antigen. Typically, the antibody binds with an affinity (KD) of less than about $10^{-7}$ M, for example, less than about $10^{-8}$ M, $10^{-9}$ M or $10^{-10}$ M or even less.

As used herein, "KD" or "Kd" refers to the dissociation equilibrium constant for particular antibody-antigen interaction. Typically, the antibody of the present disclosure binds to human Abeta with a dissociation equilibrium constant (KD) of less than about $10^{-7}$M, for example, less that about $10^{-8}$M, $10^{-9}$M or $10^{-10}$M or even less, for example, as determined by Surface Plasma Resonance (SPR) technology in Biacore T200 instrument.

As used herein, "competitive binding" and "competitively binds to" refers to an antibody recognizing and binding to the same epitope (also called an antigenic determinant) or a part of the same epitope on human Abeta as that of the monoclonal antibodies of the present disclosure. An antibody binding to the same epitope as the monoclonal antibodies of the present disclosure refers to an antibody that recognizes and binds to human Abeta amino acid sequence which is recognized by the monoclonal antibodies of the present disclosure.

When the term "competition" is used in the context of antigen binding proteins (e.g., neutralizing antigen binding proteins or neutralizing antibodies) that compete for the same epitope, it means that competition occurs between the antigen binding proteins, which is determined by the assays wherein an antigen binding protein to be tested (e.g., an antibody or immunologically functional fragment thereof) prevents or inhibits (e.g., reduces) the specific binding of a reference antigen binding protein (e.g., a ligand or reference antibody) to a common antigen (e.g., an PD-L1 antigen or fragment thereof). Numerous types of competitive binding assays are available to determine whether an antigen binding protein competes with another. These assays are, for example, solid phase direct or indirect radioimmunoassay (RIA), solid phase direct or indirect enzyme immunoassay (EIA), Sandwich competition assay (see, e.g., Stahli et al, 1983, Methods in Enzymology 9: 242-253); solid phase direct biotin-avidin EIA (see, e.g., Kirkland et al, 1986, J. Immunol. 137: 3614-3619), solid phase direct labeling assay, solid phase direct labeling sandwich assay (see, e.g., Harlow and Lane, 1988, Antibodies, A Laboratory Manual, Cold Spring Harbor Press); solid phase direct labeling RIA with I-125 label (see, e.g., Morel et al, 1988, Molec. Immunol. 25: 7-15); solid phase direct biotin-avidin EIA (see, e.g., Cheung, et al, 1990, Virology 176: 546-552); and direct labeling RIA (Moldenhauer et al, 1990, Scand. J. Immunol. 32: 77-82). Typically, the assay involves the use of a purified antigen capable of binding to a solid surface or cell loaded with both an unlabeled test antigen binding protein and a labeled reference antigen binding protein. Competitive inhibition is determined by measuring the amount of label bound to the solid surface or to the cell in the presence of the test antigen binding protein. Usually, the test antigen binding protein is present in excess. Antigen binding proteins identified by competitive assay (competing with the antigen binding protein) includes: antigen binding proteins that bind to the same epitope as the reference antigen binding protein; and antigen binding proteins that bind to an epitope that is sufficiently close to the epitope to which the reference antigen binding protein binds, where the two epitopes spatially interfere with each other to hinder the binding. Additional details regarding methods for determining competitive binding are provided in the Examples herein. Typically, when a competing antigen binding protein is present in excess, it will inhibit (e.g., reduce) at least 40-45%, 45-50%, 50-55%, 55-60%, 60-65%, 65-70%, 70-75% or 75% or even more of the specific binding of the reference antigen binding protein to the common antigen. In some cases, the binding is inhibited by at least 80-85%, 85-90%, 90-95%, 95-97%, or 97% or even more.

As used herein, "nucleic acid molecule" refers to DNA molecules and RNA molecules. A nucleic acid molecule may be single-stranded or double-stranded, but preferably is double-stranded DNA. A nucleic acid is "operably linked" when it is placed into a functional relationship with another nucleic acid sequence. For instance, a promoter or enhancer is operably linked to a coding sequence if it affects the transcription of the sequence.

As used herein, "vector" refers to a nucleic acid molecule capable of transporting another nucleic acid to which it has been linked. In one embodiment, the vector is a "plasmid," which refers to a circular double stranded DNA loop into which additional DNA segments may be ligated. In another embodiment, the vector is a viral vector, wherein additional DNA segments may be ligated into the viral genome. The vectors disclosed herein are capable of self-replicating in the host cell into which they are introduced (e.g., bacterial vectors having a bacterial replication origin and episomal mammalian vectors), or may be integrated into the genome of a host cell upon introduction into the host cell, and thereby are replicated along with the host genome (e.g., non-episomal mammalian vectors).

As used herein, "host cell" refers to a cell into which an expression vector has been introduced. Host cells may include bacterial, microbial, plant or animal cells. Bacteria that are susceptible to be transformed include members of enterobacteriaceae, such as *Escherichia coli* or *Salmonella* strains; Bacillaceae such as *Bacillus subtilis*; Pneumococcus; *Streptococcus* and *Haemophilus influenzae*. Suitable microorganisms include *Saccharomyces cerevisiae* and *Pichia pastoris*. Suitable animal host cell lines include CHO (Chinese hamster ovary cell line) and NS0 cells.

Methods for producing and purifying antibodies and antigen-binding fragments are well known in the art, for example, A Laboratory Manual for Antibodies, Cold Spring Harbor Laboratory Press, Cold Spring Harbor, N.Y., chapters 5-8 and 15. For example, mice can be immunized with human Abeta or fragments thereof, and the resulting antibodies can then be renatured, purified, and sequenced for amino acid sequences by using conventional methods well known in the art. Antigen-binding fragments can also be prepared by conventional methods. The antibodies or antigen binding fragments of the present disclosure are engineered to contain one or more human framework regions and CDRs derived from non-human antibody. Human FR germline sequences can be obtained from ImMunoGeneTics (IMGT) via their website http://imgt.cines.fr, or from The Immunoglobulin Facts Book, 2001, ISBN 012441351, by aligning against IMGT human antibody variable germline gene database and using MOE software.

The engineered antibodies or antigen binding fragments of the present disclosure may be prepared and purified using known methods. For example, cDNA sequences encoding a heavy chain and a light chain may be cloned and engineered into a GS expression vector. The vectors expressing recombinant immunoglobulin may then be stably transfected into CHO cells. As a more recommended method well known in the art, mammalian expression systems will result in glycosylation, typically at highly conserved N-terminal sites in the Fc region. Stable clones expressing an antibody specifically binding to human TIM-3 were obtained. Positive clones may be expanded in serum-free culture medium in bioreactors for antibody production. Culture medium, into which an antibody has been secreted, may be purified by conventional techniques. For example, purification may be performed on Protein A or G Sepharose FF column that has been modified with buffer. The nonspecific binding components are washed out. The bound antibody is eluted by pH gradient and antibody fragments are detected by SDS-PAGE, and then pooled. The antibodies may be filtered and concentrated using common techniques. Soluble aggregates and multimers may be effectively removed by common techniques, such as size exclusion or ion exchange. The resulting product is then immediately frozen, for example at −70° C., or may be lyophilized.

As used herein, "mutation" includes but not being limited to "back-mutation", "conservative modification" or "conservative substitution or replacement". As used herein, "conservative modification" or "conservative substitution or replacement" refers to substitutions of other amino acids having similar characteristics (e.g. charge, side-chain size, hydrophobicity/hydrophilicity, backbone conformation and rigidity, etc.) for the amino acids in a protein, such that the changes can frequently occur without altering the biological activity of the protein. Those skilled in the art recognize that, in general, single amino acid substitution in non-essential regions of a polypeptide does not substantially alter biological activity (see, e.g., Watson et al. (1987) Molecular Biology of the Gene, The Benjamin/Cummings Pub. Co., p. 224 (4th Ed.)). In addition, substitutions of structurally or functionally similar amino acids are less likely to disrupt biological activity.

The "mutated sequence" mentioned in the present disclosure refers to the nucleotide sequence and amino acid sequence having various percentage sequence identity to those of the present disclosure, after modifying the nucleotide sequence and amino acid sequence of the present disclosure by appropriate substitution, insertion or deletion. The sequence identity described in the present disclosure may be at least 85%, 90% or 95%, preferably at least 95%. Non-limiting examples include 85%, 86%, 87%, 88%, 89%, 90%, 91%, 92%, 93%, 94%, 95%, 96%, 97%, 98%, 99%, 100%. Sequence comparison and determination of percent identity between two sequences can be performed using BLASTN/BLASTP algorithm with default settings available on the National Center For Biotechnology Institute website.

As used herein, "homology" or "identity" or "consistency" refers to sequence similarity between two polynucleotide sequences or between two polypeptide sequences. When a position in both of the two sequences to be compared is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions to be compared and then multiplied by 100. For example, if 6 out of 10 positions in two sequences are matched or homologous when the sequences are optimally aligned, then the two sequences have 60% homology; if 95 out of 100 positions in two sequences are matched or homologous, then the two sequences have 95% homology. Generally, the comparison is performed when two sequences are aligned to give maximum percent homology.

The "exogenous" mentioned in the present disclosure refers to substances produced outside organisms, cells, or humans according to circumstances. "Endogenous" refers to substances produced in cells, organisms, or human bodies according to circumstances.

As used herein, "cell," "cell line," and "cell culture" are used interchangeably and all such designations include progeny. Thus, the words "transformant" and "transformed cell" include the primary subject cells and cultures derived therefrom regardless of the number of passages. It should be also understood that all progeny may not be precisely identical in DNA content, due to deliberate or random mutations. Mutant progeny that have the same function or biological activity as that in the originally transformed cells are included. Where distinct designations are intended to, it will be clearly understood from the context.

As used herein, "polymerase chain reaction" or "PCR" refers to a procedure or technique in which minute amounts of a specific portion of nucleic acid, RNA and/or DNA, are amplified as described in, e.g., U.S. Pat. No. 4,683,195. Generally, sequence information at the ends of or beyond the region of interest needs to be available, such that oligonucleotide primers can be designed; these primers will be identical or similar in sequence to opposite strands of the template to be amplified. The 5' terminal nucleotides of the two primers can coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al. (1987) Cold Spring Harbor Symp. Ouant. Biol. 51:263; Erlich, ed., (1989) PCR TECHNOLOGY (Stockton Press, N.Y.). The PCR test used in the present disclosure is considered to be one, but not the only, example of polymerase reaction method for amplifying a test nucleic acid sample. The method comprises the use of known nucleic acid sequences as primers and nucleic acid polymerase to amplify or generate a specific portion of nucleic acid.

As used herein, "pharmaceutical composition" refers to a mixture containing one or more compounds according to the present disclosure or a physiologically/pharmaceutically acceptable salt or produg thereof and other chemical components, such as physiologically/pharmaceutically acceptable carriers and excipients. The pharmaceutical composition aims at promoting the administration to an organism, facilitating the absorption of the active ingredient and thereby exerting a biological effect.

As used herein, "treat" means to internally or externally administer a therapeutic agent, such as a composition containing any of binding compounds of the present disclosure, to a patient having one or more disease symptoms for which the agent has known therapeutic activity. Typically, the agent is administered in an amount effectively to alleviate one or more disease symptoms in the patient or population to be treated, whether by inducing the regression of or inhibiting the progression of such symptom(s) by any clinically measurable degree. The amount of a therapeutic agent that is effective to alleviate any particular disease symptom (also referred to as the "therapeutically effective amount") may vary according to various factors such as the disease state, age, and body weight of the patient, and the ability of the drug to elicit a desired response in the patient Whether a disease symptom has been alleviated can be assessed by any clinical measurement typically used by physicians or other skilled healthcare providers to assess the severity or progression status of that symptom. While an embodiment of the present disclosure (e.g., a treatment method or article of manufacture) may not be effective in alleviating the target disease symptom(s) in every patient, it should alleviate the target disease symptom(s) in a statistically significant number of patients as determined by any statistical test known in the art such as Student's t-test, chi-square test, U-test according to Mann and Whitney, Kruskal-Wallis test (H-test), Jonckheere-Terpstra-test and Wilcoxon-test.

As used herein, "effective amount" encompasses an amount sufficient to ameliorate or prevent a symptom or sign of the medical condition. Effective amount also means an amount sufficient to allow or facilitate diagnosis. An effective amount for a particular patient or veterinary subject may vary depending on factors such as the condition being treated, the overall health condition of the patient, the route and dose of administration and the severity of side effects. An effective amount can be the maximal dose or dosing protocol that avoids significant side effects or toxic effects.

As used herein, "administration" or "treatment," as it applies to an animal, human, experimental subject, cell, tissue, organ, or biological fluid, refers to contacting an exogenous pharmaceutical, therapeutic, diagnostic agent, or composition with the animal, human, subject, cell, tissue, organ, or biological fluid. "Administration" or "treatment" can refer, e.g., to therapeutic, pharmacokinetic, diagnostic, research, and experimental methods. Treatment of a cell encompasses contacting a reagent with the cell, as well as contacting a reagent with a fluid, where the fluid is in contact with the cell. "Administration" or "treatment" also means in vitro or ex vivo treatments, e.g., of a cell, with a reagent, diagnostic, binding composition, or with another cell. "Treatment", as it applies to a human, veterinary, or research subject, refers to therapeutic treatment, prophylactic or preventative measures, research and diagnostic applications.

As used herein, "disease or disorder caused by Abeta" refers to a disease or disorder caused by or associated with β-amyloid, including but not limited to diseases and disorders caused by the presence or activity of β-amyloid consisting of Abeta monomers, or protofibrils, or polymers, or any combination thereof, for example, neurodegenerative disease (for example: Alzheimer's disease, mild cognitive disorder, frontotemporal dementia, Lewy body disease, Parkinson's disease, Pick's disease, Bevac's disease, etc.), various eye diseases caused by β-amyloid deposition (for example, macular degeneration, drusen-associated optic neuropathy, glaucoma, cataract, etc.).

As used herein, "neurodegenerative diseases" include but are not limited to: Alzheimer's disease, mild cognitive disorder, frontotemporal dementia, Lewy body disease, Parkinson's disease, Pick's disease, Bevac's disease, Congophilic amyloid angiopathy, cerebral amyloid angiopathy, Down syndrome, multiple infarct dementia, Huntington's disease, Creutzfeldt-Jakob Disease, AIDS dementia syndrome, depression, anxiety disorder, phobia, Bell's palsy, epilepsy, encephalitis, multiple sclerosis, neuromuscular disorder, neurotumor disorder, brain tumor, neurovascular disorder including stroke, neuroimmunity disorder, neuropathic otology disease, neurotrauma including spinal cord injury, pain including neuropathic pain, pediatric neuro and neuropsychiatric disorder, sleep disorder, Tourette's syndrome, mild cognitive disorder, vascular dementia, multiple infarct dementia, cystic fibrosis, Gaucher's disease and other dyskinesia and diseases of the central nervous system.

DETAILED DESCRIPTION OF THE INVENTION

The following examples are provided to further describe the present disclosure, but are not intended to limit the scope of the disclosure. Experimental methods for which the specific conditions are not indicated in the examples of the present disclosure are generally carried out according to conventional conditions, such as Sambrook et al., Antibodies, Molecular Cloning, Laboratory Manual, Cold Spring Harbor Laboratory; or according to the conditions recommended by the manufacturer. Reagents for which the sources are not specifically indicated are commercially available reagents.

Example 1. Preparation of Abeta Antigen

The Abeta antigens used in the examples and test examples of the present disclosure were synthesized by GL Biochem, GenScript or Sigma, and then prepared in vitro (see Table 1 for details). The Abeta antigens for use in immunization were Aβ 1-42 protofibrils and Aβ1-40 KLH; The Abeta antigens for use in screening were Aβ1-40-BSA fibrils, Aβ1-40 DMSO suspension, Aβ1-42-biotin DMSO suspension, Aβ1-42 protofibrils and Aβ1-42 fibrils; Abeta antigens for use in detection were Aβ1-42 monomer and Aβ1-42 fibrils.

The amino acid sequence of Aβ1-40 is shown in (SEQ ID NO:1):

DAEFRHDSGYEVHHQKLVFFAEDVGSNKGAIIGLMVGGVV;

The amino acid sequence of Aβ1-42 is shown in (SEQ ID NO: 2):

DAEFRHDSGYEVHRQKLVFFAEDVGSNKGAIIGLMVGGVVIA.

Aβ1-40 KLH and Aβ1-40-BSA refer to synthesized Aβ1-40 polypeptide coupled with KLH (Keyhole Limpet Hemocyanin) and BSA (Bovine Serum Albumin), respectively, wherein the used Aβ1-40 was incorporated with amino acid Cys at the N-terminus for the convenience of coupling and detection;

Aβ1-42 protofibrils refers to Aβ1-42 polypeptide prepared in the form of protofibrils in vitro.

Aβ1-40-BSA fibrils refers to Aβ1-42 polypeptide coupled with BSA prepared in the form of fibrils in vitro.

Aβ1-40 DMSO suspension refers to a clear solution prepared by directly dissolving Aβ1-42 polypeptide in DMSO (dimethyl sulfoxide).

Aβ1-42-biotin DMSO suspension refers to a clear solution prepared by directly dissolving biotin tagged Aβ1-42 polypeptide in DMSO (dimethyl sulfoxide).

Aβ1-42 fibrils refers to Aβ1-42 polypeptide prepared in the form of fibrils in vitro.

Aβ1-42 monomer refers to Aβ1-42 monomer.

TABLE 1

A beta antigens for use in immunization, screening and detection, and their corresponding preparation method

| Use | Polypeptide | Supplier and Catalog number | Preparation method |
|---|---|---|---|
| immunization | Aβ1-42 protofibrils | GL Biochem 180231 | Aβ peptide powder was dissolved in 10 mM NaOH (pH > 10), shaken for 2 min, added with 10 × PBS at the volume of one-tenth of that of NaOH to make a final concentration of 443 μM. |

TABLE 1-continued

A beta antigens for use in immunization, screening and detection, and their corresponding preparation method

| Use | Polypeptide | Supplier and Catalog number | Preparation method |
|---|---|---|---|
| | Aβ 1-40 KLH | GL Biochem KLH-SH-CV-41 479311 | Such solution was incubated at 37° C. overnight, and then diluted with PBS to 50 μM to result in Aβ1-42 protofibrils. The polypeptide was directly dissolved in PBS to result in 1 mg/ml turbid solution. |
| Screening Hybridoma | Aβ1-40-BSA fibrils | GL Biochem BSA-SH-CV-41 479311 | The synthesized Aβ1-40-BSA powder was dissolved in DMSO at 0.5 mg/10 μl, and then was diluted with 434 μl deionized water. The resulting Aβ was placed at 37° C. for 10 days to result in Aβ1-40-BSA fibrils. |
| | Aβ1-40 DMSO suspension | GL Biochem DV-40 82357 | Polypeptide was directly dissolved in DMSO at 1 mg/ml. |
| | Aβ1-42-biot in DMSO suspension | GL Biochem Bio-DA-42 212574 | Polypeptide was directly dissolved in DMSO at 1 mg/ml. |
| | Aβ1-42 fibrils | GL Biochem P160217-SY180231 | The synthesized Aβ1-42 powder was dissolved in DMSO at 0.5 mg/10 μl, and then was diluted with 434 μl deionized water. The resulting Aβ was placed at 37° C. for 10 days to result in Aβ1-42 fibrils. |
| | Aβ1-42 protofibrils | GL Biochem 180231 | The preparation method was the same as that for Aβ1-42 protofibrils for use in immunization. |
| ThT assay | Aβ1-42 monomer | GenScript RP10017 | The synthesized Aβ1-42 polypeptide powder was dissolved in pre-cooled buffer (2 × PBS and 10 mM NaOH, pH > 10, mixed at ratio of 1:1(v/v)) at a final concentration of 1 mg/ml. |
| Neuronal protection assay BV2 phagocytosis assay Microglia phagocytosis assay | Aβ1-42 fibrils | GL Biochem P160427-SY507408 P160802-SY180231 P160802-SY180231 | The synthesized Aβ1-42 powder was dissolved in DMSO at 0.5 mg/10 μl, and then was diluted with 434 μl deionized water. The resulting Aβ was placed at 37° C. for 10 days to result in Aβ1-42 fibrils. |
| Biacore | Aβ1-42 monomer | Sigma A 9810 | Aβ1-42 polypeptide powder was dissolved in DMSO at a final concentration of 2 mg/ml. |
| | Aβ1-42 fibrils | GL Biochem, P160217-SY180231 and P160802-SY180231 | The synthesized Aβ1-42 powder was dissolved in DMSO at 0.5 mg/10 μl, and then was diluted with 434 μl deionized water. The resulting Aβ was placed at 37° C. for 10 days to result in Aβ1-42 fibrils. |

Example 2. Preparation of Anti-Human Abeta Hybridoma Monoclonal Antibody

1. Immunization

Anti-human Abeta monoclonal antibodies were produced by immunizing mice. SJL white mice, female, 6-8 weeks old were used for experiment (Beijing Vital River Experimental Animal Technology Co., Ltd., animal production license number: SCXK (Beijing) 2012-0001). Feeding environment: SPF level. After the mice were purchased, they were kept in the laboratory environment for 1 week, 12/12 hours light/dark cycle, at temperature of 20-25° C.; humidity of 40-60%. Then, mice were immunized according to the following schemes. The antigens for immunization were Aβ1-40-K LH and Aβ1-42 protofibrils.

Immunization Scheme 1: Adjuvant used for immunization was QuickAntib ody-Mouse3W (Beijing Kangbiquan Biotechnology Co., Ltd. Cat No. KX0210042. The ratio of antigen to adjuvant (QuickAntibody-Mouse3W) was 1:1, 10 μg/mouse/time. The antigen and the adjuvant were mixed thoroughly and used for inoculation at day 0, 7, 14, 21, 28, 35 and 42. On day 0, the mice were injected intramuscularly (IM) at hind leg with 10 μg/mouse of the mixed antigen. The first immunization was repeated on day 7, 14, 21, 28, 35 and 42, and the mice were similarly injected intramuscularly (IM) at hind leg with 10 μg/mouse of the mixed antigen. Blood samples were collected on day 19, 40 and 55, and the antibody titer in mouse serum was determined by ELISA method. After the seventh to eighth immunization, mice with a high serum antibody titer tending to the plateau were selected for splenocyte fusion. Three days before the splenocyte fusion, antigen solution prepared with saline was intraperitoneally injected (IP), 20 μg/mouse, for booster immunization.

Immunization Scheme 2: Adjuvant used for immunization was QuickAntib ody-Mouse5W (Beijing Kangbiquan Biotechnology Co., Ltd. Cat No. KX021004). The ratio of antigen to adjuvant (QuickAntibody-Mouse5W) was 1:1, 25 μg/mouse/time (for first immunization) and 25 μg/mouse/time (for booster immunization). The antigen and the adjuvant were mixed thoroughly and used for inoculation at day 0, 14, 28, 42 and 56. On day 0, the mice were injected intramuscularly (IM) at hind leg with 25 μg/mouse of the mixed antigen. The first immunization was repeated on day 14, 28, 42 and 56, and the mice were similarly injected intramuscularly (IM) at hind leg with 25 μg/mouse of the mixed antigen. Blood samples were collected on day 20 and 49, and the antibody titer in mouse serum was determined by ELISA method. After the fifth immunization, mice with a high serum antibody titer tending to the plateau were selected for splenocyte fusion. Three days before the splenocyte fusion, antigen solution prepared with saline was intraperitoneally injected (IP), 50 μg/mouse, for booster immunization.

2. Splenocyte Fusion

Hybridoma cells were obtained by fusing splenic lymphocytes with myeloma Sp2/0 cells (ATCC® CRL-8287™) by using an optimized PEG-mediated fusion procedure. The fused hybridoma cells were resuspended in complete medium (DMEM medium comprising 20% FBS, 1×HAT, 1×OPI) at a density of 0.5-1×10$^6$/ml, seeded in a 96-well plate with 100 μl/well, incubated at 37° C. and 5% $CO_2$ for 3-4 days, supplemented with 100p/well of HAT complete medium, and cultured for 3-4 days until forming pin-like clones. The supernatant was removed, added with 200 μl/well of HT complete medium (RPMI-1640 medium comprising 20% FBS, 1×HT and 1×OPI), incubated at 37° C., 5% $CO_2$ for 3 days and then subjected for ELISA detection.

3. Screening of Hybridoma Cells 10-11 days after fusion, according to the cell growth density, ELISA binding assay (also known as enzyme-linked immunosorbent assay) was performed on clone culture supernatant with various forms of Aβ polypeptide for preliminary screening, to classify the subtypes of the resulting hybridoma clones. Aβ1-40-BSA fibrils, Aβ1-42 biotin DMSO suspension and Aβ1-40 DMSO suspension were used for screening hybridoma cells with Aβ1-40-KLH as an immunogen; and Aβ1-42 protofibrils, Aβ1-42 fibrils and Aβ1-42-biotin DMSO suspension were used for screening hybridoma cells with Aβ1-42 protofibrils as an immunogen.

For positive wells, medium was changed and expanded to 24-well plate according to the cell density. The cell lines transferred into a 24-well plate were tested again and then sub-cloned for the first time. Some of the positive cells screened in the first sub-cloning were preserved, and used for the second sub-cloning. Some of the positive cells screened in the second sub-cloning were preserved, and used for protein expression. Hybridoma cells capable of specifically binding to Aβ polypeptide were resulted from multiple fusions. After thioflavin (also referred to as ThT) fluorescence assay, neuronal protection assay and macrophage phagocytosis assay, hybridoma clone mAb-2401, mAb-3601, mAb-5101 and mAb-9001 were obtained and were used for preparation of antibodies with serum-free cell culture. The resulting antibodies were purified according to the example of purification and the purified antibodies were used in the test examples.

4. Purification of Hybridoma Antibodies and Recombinant Antibodies

The supernatant samples expressed by cells were centrifuged at high speed to remove impurities, and the supernatant expressed by hybridoma was purified by Protein G column and the supernatant expressed by recombinant antibodies was purified by Protein A column. The column was washed with PBS (pH 7.4) until the A280 reading dropped to the baseline. The target proteins were eluted with 100 mM acetic acid, pH3.0, and neutralized with 1M Tris-HCl, pH8.0. The eluted samples were properly concentrated and then further purified with gel chromatography Superdex200 (GE) pre-equilibrated with PBS to remove aggregates. The monomer peaks were collected and aliquoted for use.

5. Sequencing of the Positive Hybridoma Clones

The procedures of cloning the sequences from the positive hybridoma were as follows. Hybridoma cells in logarithmic growth phase were collected. RNAs were extracted with Trizol (Invitrogen, Cat No. 15596-018) according to the kit's instructions and were reversely transcribed with PrimeScript™ Reverse Transcription kit (Takara, Cat No. 2680A). The resulting cDNAs were amplified by PCR using mouse Ig-Primer Set (Novagen, TB326 Rev. B 0503), and sequenced by a company. The amino acid sequences of the mouse antibody heavy chain variable region (VH) and light chain variable region (VL) of hybridoma clones mAb-2401, mAb-3601, mAb-5101 and mAb-9001 were determined as follows:

```
> mAb-2401 VH
                                                              (SEQ ID NO: 3)
EVQLQQSVAELVRPGASVKLSCTASGFNIKNTYMHWVKQRPEQGLEWIGRIDPTNGNTKYAPK

FKDKATIIADTSSNTGYLQLSSLTSEDTAIYYCARRVYYYDSTYNYWGQGTTLTVSS

> mAb-2401VL
                                                              (SEQ ID NO: 4)
DIVMTQSPSSLTVTAGEKVTMSCKSSQSLLNSGNQKNYLTWYQQKPGQPPKLLIYWASTRESG

VPDRPTGSGSRTDFTLTISNVQAEDLAVYYCQNDYNYPLTFGAGTKLELK

> mAb-3601 VH
                                                              (SEQ ID NO: 5)
QATLKESGPGILQSSQTLSLTCSFSGFSLSTFGMGVGWIRQPSGKGLEWLAHIWWDDDKYYNP

ALKSRLTISKDTSKNQVFLKIANVDTADTATYYCARRPLGSYDYFDYWGQGTTLTVSS

> mAb-3601 VL
                                                              (SEQ ID NO: 6)
DVLMTQTPLSLPVSLGDQASISCRSSQSIVHSNGNTYLEWYLQKPGQSPKLLIYKVSNRPSGVPD

RFSGSGSGTDFTLKISRVEAEDLGVYYCFQGSRVPLTFGAGTKLELK
```

-continued

> mAb-5101 VH (SEQ ID NO: 7)

QVTLKESGPGILQSSQTLSLTCSFSGFSLTTSGMGVSWIRQPSGKGLEWLAHIYWDDVSLYNPSL
KSRLTISKDASRNQVFLKITSVDTADSATYYCVRRRIITVVDAMDYWGQGTSVTVSS

> mAb-5101 VL (SEQ ID NO: 8)

DVLMTQTPLSLPVSLGDQASISCRSSQSIVHSNGNTYLEWYLQKSGQSPKLLIYKVSNRFSGVPD
RFSGSGSGTDFTLKISRVEAEDLGIYYCCQGSRVPPTFGGGTKLEIK

> mAb-9001 VH (SEQ ID NO: 9)

QVTLKESGPGILQPSQTLSLTCSFSGFSLSTFGMGVGWIRQPSGKGLEWLAHIWWDDDKYYNP
ALKSRLTISKDTSKNQVFLKIAIVDTADIATYYCVRRGFHLGSRGDYFDHWGQGTTLTVSS

> mAb-9001 VL (SEQ ID NO: 10)

DVLMTQTPLSLPVSLGDQASISCRSSQSIVHSNGNTYLEWYLQKPGQSPKLLIYKVSNRFSGVPD
RFSGSGSGTDFTLKISRVEAEDLGVYYCFQGSRVPLTFGAGTKLELK

Note: The variable region amino acid sequences of the above antibodies are represented as FR1-CDR1-FR2-CDR2-FR3-CDR3-FR4. The characters in italics indicate FR sequences and the underlined characters indicate CDR sequences.

The amino acid sequences of the CDR regions of antibodies mAb-2401, mAb-3601, mAb-5101 and mAb-9001 were shown in Table 2.

TABLE 2

Heavy chain and light chain CDR region amino acid sequences of Anti-Abeta antibodies

| Antibody | Heavy chain | | Light chain | |
|---|---|---|---|---|
| mAb-2401 | HCDR1 | NTYMH SEQ ID NO: 11 | LCDR1 | KSSQSLLNSGNQKNYLT SEQ ID NO: 14 |
|  | HCDR2 | RIDPTNGNTKYAPKFKD SEQ ID NO: 12 | LCDR2 | WASTRES SEQ ID NO: 15 |
|  | HCDR3 | RVYYYDSTYNY SEQ ID NO: 13 | LCDR3 | QNDYNYPLT SEQ ID NO: 16 |
| mAb-3601 | HCDR1 | TFGMGVG SEQ ID NO: 17 | LCDR1 | RSSQSIVHSNGNTYLE SEQ ID NO: 20 |
|  | HCDR2 | HIWWDDDKYYNPALKS SEQ ID NO: 18 | LCDR2 | KVSNRFS SEQ ID NO: 21 |
|  | HCDR3 | RPLGSYDYFDY SEQ ID NO: 19 | LCDR3 | FQGSRVPLT SEQ ID NO: 22 |
| mAb-5101 | HCDR1 | TSGMGVS SEQ ID NO: 23 | LCDR1 | RSSQSIVHSNGNTYLE SEQ ID NO: 20 |
|  | HCDR2 | HIYWDDVSLYNPSLKS SEQ ID NO: 24 | LCDR2 | KVSNRFS SEQ ID NO: 21 |
|  | HCDR3 | RRIITVVDAMDY SEQ ID NO: 25 | LCDR3 | CQGSRVPPT SEQ ID NO: 26 |
| mAb-9001 | HCDR1 | TFGMGVG SEQ ID NO: 17 | LCDR1 | RSSQSIVHSNGNTYLE SEQ ID NO: 20 |
|  | HCDR2 | HIWWDDDKYYNPALKS SEQ ID NO: 18 | LCDR2 | KVSNRFS SEQ ID NO: 21 |
|  | HCDR3 | RGFHLGSRGDYFDH SEQ ID NO: 27 | LCDR3 | FQGSRVPLT SEQ ID NO: 22 |

Example 3. Humanization of Anti-Human Abeta Hybridoma Monoclonal Antibodies

The canonical structure was determined according to light chain variable region sequence and heavy chain variable region sequence of mouse antibody. Among human germline sequences with the same structure, those sequences most similar to mouse non-CDR regions (framework regions) were selected as templates for humanization. Then, the murine antibody CDR regions were grafted onto the selected templates for humanization to replace the human CDR regions. Back-mutations or point mutations were made on some FR region sequences as required. The variable regions were then combined with human constant region(s) (such as human IgG1 constant region) to result in humanized anti-Abeta antibodies.

1. Humanization of mAb-2401

The templates for humanization of mAb-2401 antibody heavy chain were IGHV1-24*01 and hjh6.3. That is, FR1, FR2 and FR3 regions from human germline heavy chain IGHV1-24 were selected, and JH6 region of hjh6.3 was selected as FR4 region. The templates for light chain were IGKV1-27*01 and hjk4.1. That is, FR1, FR2, and FR3 from human germline light chain IGKV1-27 were selected, and JK4 region of hjk4.1 was selected as FR4 region.

The amino acid sequence of the human germline (IGHV1-24*01) heavy chain template was shown in (SEQ ID NO:28):

QVQLVQSGAEVKKPGASVKVSCKVSGYTLTELSMHWVRQAPGKGLEWMGG

FDPEDGETIYAQKFQGRVTMTEDTSTDTAYMELSSLRSEDTAVYYCAT

The amino acid sequence of the human germline (IGKV1-27*01) light chain template was shown in (SEQ ID NO: 29):

DIQMTQSPSSLSASVGDRVTITCRASQGISNYLAWYQQKPGKVPKLLI

YAASTLQSGVPSRFSGSGSGTDFTLTISSLQPEDVATYYCQKYNSAP

The humanized heavy and light chain variable regions were as follows:

```
HAB-2401 grafted VL (SEQ ID NO: 66):
QVQLVQSGAEVKKPGASVKVSCKVSGYTLTNTYMHW

VRQAPGKGLEWMGRIDPTNGNTKYAPKFKDRVTMTE

DTSTDTAYMELSSLRSEDTAVYYCATRVYYYDSTYN

YWGKGTTVTSS

HAB-2401 grafted VL (SEQ ID NO: 67):
DIQMTQSPSSLSASVGDRVTITCKSSQSLLNSGNQK

NYLTWYQQKPGKVPKLLIYWASTRESGVPSRFSGSG

SGTDFTLTISSLQPEDVATTYCQNDYNYPLTFGGGT

KVEIK
```

The murine antibody CDR regions were grafted onto the selected humanization template to replace the human template CDR regions, and back-mutations were made on heavy chain at position 1, 72 and 98 (natural sequence numbering, corresponding to position 1, 71 and 94 respectively according to Kabat Numbering) (Q1E, E72A and T98R; Q1E, E71A, T94R according to Kabat numbering), and then combined with the constant region of human IgG1 to result in the humanized antibody HAB-2401.

The heavy chain amino acid sequence of HAB-2401 was shown in (SEQ ID NO: 30):

```
EVQLVQSGAEVKKPGASVKVSCKVSGY

TLTNTYMHWVRQAPGKGLEWMGRIDPT

NGNTKYAPKFKDRVTMTADTSTDTAYM

ELSSLRSEDTAVYYCARRVYYYDSTYN

YWGKGTTVTVSSASTKGPSVFPLAPSS

KSTSGGTAALGCLVKDYFPEPVTVSWN

SGALTSGVHTFPEVLQSSGLYSLSSVV

TVPSSSLGTQTYICNVNHKPSNTKVDK

KVEPKSCDKTHTCPPCPEPELLGGPSV

FLFPPKPKDTLMISRTPEVTCVVVDVS

HEDPEVKFNWYVDGVEVHNAKTKPREE

QYNSTYRVVSVLTVLHQDWLNGKEYKC

KVSNKALPAPIEKTISKAKGQPREPQV

YTLPPSRDELTKNQVSLTCLVKGFYPS

DIAVEWESNGQPENNYKTTPPVLDSDG

SFFLYSKLTVDKSRWQQGNVFSCSVMH

EALHNHYTQKSLSLSPGK
```

The light chain amino acid sequence of HAB-2401 was shown in (SEQ ID NO: 31):

```
DIQMTQSPSSLSASVGDRVTITCKSSQSLLN

SGNQKNYLTWYQQKPGKVPKLLIYWASTRES

GVPSRFSGSGSGTDFTLTISSLQPEDVATYY

CQNDYNYPLTFGGGTKVEIKRTVAAPSVFIF

PPSDEQLKSGTESVVCLLNNFYPREAKVQWK

VDNALQSGNSQESVTEQDSKDSTYSLSSTLT

LSKADYEKHKVYACEVTHQGLSSPVTKSFNR

GEC
```

Note: In the above HAB-2401 light and heavy chain amino acid sequences, characters in italics indicate FR sequence, underlined characters indicate CDR sequence, double underlined characters indicate constant region sequence.

2. Humanization of mAb-3601

The templates for humanization of mAb-3601 antibody heavy chain were IGHV3-30*01 and hjh6.3. That is, FR1, FR2 and FR3 regions from human germline heavy chain IGHV3-30 were selected, and JH6 region of hjh6.3 was selected as FR4 region. The templates for light chain were IGKV1-39*01/hjk4.1. That is, FR1, FR2, and FR3 from human germline light chain IGKV1-39 were selected, and JK4 region of hjk4.1 was selected as FR4 region.

The amino acid sequence of the human germline (IGHV3-30*01) heavy chain template was shown in (SEQ ID NO:32):

```
QVQLVESGGGVVQPGRSLRLSCAASGFTFSSYAMHWVRQAPGKGLEWVAV

ISYDGSNKYYADSVKGRFTISRDNSKNTLYLQMNSLRAEDTAVYYCAR
```

The amino acid sequence of the human germline (IGKV1-39*01) light chain template was shown in (SEQ ID NO: 33):

```
DIQMTQSPSSLSASVGDRVTITCRASQSISSYLNWYQQKPGKAPKLLIYA

ASSLQSGVPSRFSGSGSGTDFTLTISSLQPEDFATYYCQQSYSTP
```

The humanized heavy and light chain variable regions were as follows:

```
HAB-3601 grafted VH (SEQ ID NO: 68):
QVQLVESGGGVVQPGRSLRLSCAASGFTFSTF

GMGVGWVRQAPGKGLEWVAHIWWDDDKYYNPA

LKSRFTISRDNSKNTLYLQMNSLRAEDTAVYY

CARRPLGSYDYFDYWGKGTTVTVSSS

HAB-3601 grafted VL (SEQ ID NO: 69):
DIQMTQSPSSLSASVGDRVTITCRSSQSIVHSN

GNTYLEWYQQKPGKAPKLLIYKVSNRFSGVPSR

FSGSGSGTDFTLTISSLQPEDFATYYCFQGSRV

PLTFGGGTKVEIK
```

The murine antibody CDR regions were grafted onto the selected humanization template to replace the human CDR regions from the template, back-mutations were made on heavy chain at position 28 and 86 (natural sequence numbering, corresponding to position 28 and 82B respectively according to Kabat Numbering) (T28A and S86T; T28A and S82B T according to Kabat numbering), point mutation was made on heavy chain at position 58 (natural sequence numbering) (D58N) to eliminate potential aspartic acid isomerization, and then combined with the constant region of human IgG1 to result in the humanized antibody HAB-3601.

The heavy chain amino acid sequence of HAB-3601 was shown in (SEQ ID NO: 34):

```
QVQLVESGGGVVQPGRSLRLSCAASGFAFSTFGMGVGWVR

QAPGKGLEWVAHIWWDDNKYYNPALKSRFTISRDNSKNTL

YLQMNSLRAEDTAVYYCARRPLGSYDYFDYWGKGTTVTVS

SASTKGPSVFPLAPSSKSTSGGTAALGCLVKDYFPEPVTV

SWNSGALTSGVHTFPAVLQSSGLYSLSSVVTVPSSSLGTQ

TYICNVNHKPSNTKVDKKVEPKSCDKTHTCPPCPAPELLG

GPSVFLFPPKPKDTLMISRTPEVTCVVVDVSHEDPEVKFNW

YVDGVEVHNAKTKPREEQYNSTYRVVSVLTVLHQDWLNGK

EYKCKVSNKALPAPIEKTISKAKGQPREPQVYTLPPSRD

ELTKNQVSLTCLVKGFYPSDIAVEWESNGQPENNYKTTPPV

LDSDGSFFLYSKLTVDKSRWQQGNVFSCSVMHEALHNHYT
QKSLSLSPGK
```

The light chain amino acid sequence of HAB-3601 was shown in (SEQ ID NO: 35):

```
DIQMTQSPSSLSASVGDRVTITCRSSQSIVHSNGNTYLE

WYQQKPGKAPKLLIYKVSNRFSGVPSRFSGSGSGTDFTL

TISSLQPEDFATYYCFQGSRVPLTFGGGTKVEIKRTVAAP
```

-continued

```
SVFIFPPSDEQLKSGTASVVCLLNNFYPREAKVQWKVD

NALQSGNSQESVTEQDSKDSTYSLSSTLTLSKADYEKH

KVYACEVTHQGLSSPVTKSFNRGEC
```

Note: In the above HAB-3601 light and heavy chain amino acid sequences, characters in italics indicate FR sequence, underlined characters indicate CDR sequence, and double underlined characters indicate constant region sequence.

3. Humanization of mAb-5101

The templates for humanization of mAb-5101 antibody heavy chain were IGHV2-70D*04 and hjh6.1. That is, FR1, FR2 and FR3 from human germline heavy chain IgHV2-70D were selected, and JH6 region of hjh6.1 was selected as FR4 region. The templates for light chain were IGKV2-40*01 and hjk4.1. That is, FR1, FR2, and FR3 from human germline light chain IGKV2-40 were selected, and JK4 region of hjk4.1 was selected as FR4 region.

The amino acid sequence of the human germline (IGHV2-70D*04) heavy chain template was shown in (SEQ ID NO:36):

```
QVTLKESGPALVKPTQTLTLTCTFSGFSLSTSGMRVSWIRQPPGKALEWL

ARIDWDDDKFYSTSLKTRLTISKDTSKNQVVLTMTNMDPVDTATVYCARI
```

The amino acid sequence of the human germline (IGKV2-40*01) light chain template was shown in (SEQ ID NO: 37):

```
DIVMTQTPLSLPVTPGEPASISCRSSQSLLDSDDGNTYLDWYLQKPGQSP

QLLIYTLSYRASGVPDRFSGSGSGTDFTLKISRVEAEDVGVYYCMQRIEF

P
```

The humanized variable regions were as follows:

```
HAB-5101 grafted VH
                                               (SEQ ID NO: 70)
QVTLKESGPALVKPTQTLTLTCTFSGFSLSTSGMGVSWIRQPPGKALEWLAHIY

WDDVSLYNPSLKSRLTISKDTSKNQVVLTMTNMDPVDTATYYCARRRIITVVDAMD

YWGQGTTVTVSS

HAB-5101 grafted VL
                                               (SEQ ID NO: 71)
DIVMTQTPLSLPVTPGEPASISCRSSQSIVHSNGNTYLEWYLQKPGQSPQLLIYK

VSNRFSGVPDRFSGSGSGTDFTLKISRVEAEDVGVYYCCQGSRVPPTFGGGTKVEIK
```

The murine antibody CDR regions were grafted onto the selected humanization template to replace the human CDR regions from the template, back-mutations were made on light chain at position 2 and 50 (natural sequence numbering, corresponding to position 2 and 45 respectively according to Kabat Numbering) (12V and Q50K; 12V and Q45K according to Kabat numbering), point mutation was made on light chain at position 94 (natural sequence numbering) (C94S) to eliminate potential disulfide bond mismatch, and then combined with the constant region of human IgG1 to result in the humanized antibody HAB-5101.

Heavy chain amino acid sequence of HAB-5101 was shown in (SEQ ID NO: 38):

```
QVTLKESGPALVKPTQTLTLTCTFSGFSLSTSGMGVSWIRQPPGKALEWLAHIYWD

DVSLYNPSLKSRLTISKDTSKNQVVLTMTNMDPVDTATYYCARRRIITVVDAMDYW
```

-continued

GQGTTVTVSS*ASTKGPSVFPLAPSSKSTSGGTAALGCLVKDYFPEPVTVSWNSGA*

*LTSGVHTFPAVLQSSGLYSLSSVVTVPSSSLGTQTYICNVNHKPSNTKVDKKVEP*

*KSCDKTHTCPPCPAPELLGGPSVFLFPPKPKDTLMISRTPEVTCVVVDVSHEDPE*

*VKFNWYVDGVEVHNAKTKPREEQYNSTYRVVSVLTVLHQDWLNGKEYKCKV*

*SNKALPAPIEKTISKAKGQPREPQVYTLPPSRDELTKNQVSLTCLVKGFYPSDIAV*

*EWESNGQPENNYKTTPPVLDSDGSFFLYSKLTVDKSRWQQGNVFSCSVMHEAL*

*HNHYTQKSLSLSPGK*

The light chain amino acid sequence of HAB-5101 was shown in (SEQ ID NO: 39):

*DVVMTQTPLSLPVTPGEPASISC*RSSQSIVHSNGNTYLE*WYLQKPGQSPKLLIY*KVS

NRFS*GVPSRFSGSGSGTDFTLTISSLQPEDFATYYC*FQGSRVPLTF*GGGTKVEI*KRT

*VAAPSVFIFPPSDEQLKSGTASVVCLLNNFYPREAKVQWKVDNALQSGNSQES*

*VTEQDSKDSTYSLSSTLTLSKADYEKHKVYACEVTHQGLSSPVTKSFNRGEC*

Note: In the above HAB-5101 light and heavy chain amino acid sequences, characters in italics indicate FR sequence, underlined characters indicate CDR sequence, and double underlined characters indicate constant region sequence.

4. Humanization of mAb-9001

The templates for humanization of mAb-9001 antibody heavy chain were IGHV2-70D*04 and hjh6.1. That is, FR1, FR2 and FR3 from human germline heavy chain IGHV2-70 were selected, and JH6 region of hjh6.1 was selected as FR4 region. The templates for light chain were IGKV2-40*01 and hjk2.1. That is, FR1, FR2, and FR3 from human germline light chain IGKV2-40 were selected, and JK2 region of hjk2.1 was selected as FR4 region.

The amino acid sequence of the human germline (IGHV2-70D*04) heavy chain template was shown in (SEQ ID NO:36):

QVTLKESGPALVKPTQTLITTCTFSGFSLSTSGMRVSWIRQPPGKALEWL

ARIDWDDDKFYSTSLKTRLTISKDTSKNQVVLTMTNMDPVDTATYYCARI

The amino acid sequence of the human germline (IGKV2-40*01) light chain template was shown in (SEQ ID NO: 37):

DIVMTQTPLSLPVTPGEPASISCRSSQSLLDSDDGNTYLDWYLQKPGQSP

QLLIYTLSYRASGVPDRFSGSGSGTDFTLKISRVEAEDVGVYYCMQRIEF

P

The humanized variable regions were as follows:

```
HAB-9001 grafted VH
                                              (SEQ ID NO: 72)
```
*QVTLKESGPALVKPTQTLTLTCTFSGFSLS*TFGMGVGW*IRQPPGKALEWLA*HI

WWDDDKYYNPALKS*RLTISKDTSKNQVVLTMTNMDPVDTATYYCAR*RGFHLGSR

GDYFDH*WGQGTTVTVSS*

```
HAB-9001 grafted VL
                                              (SEQ ID NO: 73)
```
*DIVMTQTPLSLPVTPGEPASISC*RSSQSIVHSNGNTYLE*WYLQKPGQSPQLLIY*K

VSNRFS*GVPDRFSGSGSGTDFTLKISRVEAEDVGVYYC*FQGSRVPLTF*GQGTKLEIK*

The murine antibody CDR regions were grafted onto the selected humanization template to replace the human CDR regions from the template, back-mutation was made on light chain at position 2 (natural sequence numbering, corresponding to position 2 according to Kabat Numbering) (I2V), point mutation was made on heavy chain at position 58 (natural sequence numbering) (D58N) to eliminate potential aspartic acid isomerization, and then combined with the constant region of human IgG1 to result in the humanized antibody HAB-9001.

Heavy chain amino acid sequence of HAB-9001 was shown in (SEQ ID NO: 40):

*QVTLKESGPALVKPTQTLTLTCTFSGFSLS*TFGMGVGWIRQPPGKALEWLAHIWWD
DNKYYNPALKS*RLTISKDTSKNQVVLTMTNMDPVDTATYYCAR*RGFHLGSRGDYF
DH*WGQGTTVTVSS*ASTKGPSVFPLAPSSKSTSGGTAALGCLVKDYFPEPVTVSW
NSGALTSGVHTFPAVLQSSGLYSLSSVVTVPSSSLGTQTYICNVNHKPSNTKVDK
KVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEY
KCKVSNKALPAPIEKTISKAKGQPREPQVYTLPPSRDELTKNQVSLTCLVKGFYP
SDIAVEWESNGQPENNYKTTPPVLDSDGSFFLYSKLTVDKSRWQQGNVFSCSVM
HEALHNHYTQKSLSLSPGK

The light chain amino acid sequence of HAB-9001 was shown in (SEQ ID NO: 41):

*DVVMTQTPLSLPVTPGEPASISC*RSSQSIVHSNGNTYLEWYLQKPGQSPQLLIYKVS
NRFS*GVPDRFSGSGSGTDFTLKISRVEAEDVGVYYC*FQGSRVPLTFGQGTKLEIK*RT
VAAPSVFIFPPSDEQLKSGTASVVCLLNNFYPREAKVQWKVDNALQSGNSQESV
TEQDSKDSTYSLSSTLTLSKADYEKHKVYACEVTHQGLSSPVTKSFNRGEC

Note: In the above HAB-9001 light and heavy chain amino acid sequences, characters in italics indicate FR sequence, underlined characters indicate CDR sequence, and double underlined characters indicate constant region sequence.

In addition, with respect to the constant region sequences of antibody HAB-2401, HAB-3601, HAB-5101 and HAB-9001, the amino acid sequence of the heavy chain constant region was shown in SEQ ID NO: 42, the amino acid sequence of the light chain constant region was shown in SEQ ID NO: 43, the variable region amino acid sequences and full-length amino acid sequences were shown in the following table:

TABLE 3

Heavy chain and light chain amino acid sequences of humanized Anti-Abeta antibodies

| Antibody | Heavy chain | | Light chain | |
| --- | --- | --- | --- | --- |
| HAB-2401 | Variable region sequence (VH) | SEQ ID NO: 44 | Variable region sequence (VL) | SEQ ID NO: 45 |
| | Full-length sequence (H) | SEQ ID NO: 30 | Full-length sequence (L) | SEQ ID NO: 31 |
| HAB-3601 | Variable region sequence (VH) | SEQ ID NO: 46 | Variable region sequence (VL) | SEQ ID NO: 47 |
| | Full-length sequence (H) | SEQ ID NO: 34 | Full-length sequence (L) | SEQ ID NO: 35 |
| HAB-5101 | Variable region sequence (VH) | SEQ ID NO: 48 | Variable region sequence (VL) | SEQ ID NO: 49 |
| | Full-length sequence (H) | SEQ ID NO: 38 | Full-length sequence (L) | SEQ ID NO: 39 |
| HAB-9001 | Variable region sequence (VH) | SEQ ID NO: 50 | Variable region sequence (VL) | SEQ ID NO: 51 |
| | Full-length sequence (H) | SEQ ID NO: 40 | Full-length sequence (L) | SEQ ID NO: 41 |
| HAB-2401 | HCDR1 | SEQ ID NO: 11 | LCDR1 | SEQ ID NO: 14 |
| | HCDR2 | SEQ ID NO: 12 | LCDR2 | SEQ ID NO: 15 |
| | HCDR3 | SEQ ID NO: 13 | LCDR3 | SEQ ID NO: 16 |
| HAB-3601 | HCDR1 | SEQ ID NO: 17 | LCDR1 | SEQ ID NO: 20 |
| | HCDR2 | SEQ ID NO: 52 | LCDR2 | SEQ ID NO: 21 |
| | HCDR3 | SEQ ID NO: 19 | LCDR3 | SEQ ID NO: 22 |

TABLE 3-continued

Heavy chain and light chain amino acid sequences of humanized Anti-Abeta antibodies

| Antibody | Heavy chain | | Light chain | |
|---|---|---|---|---|
| HAB-5101 | HCDR1 | SEQ ID NO: 23 | LCDR1 | SEQ ID NO: 20 |
|  | HCDR2 | SEQ ID NO: 24 | LCDR2 | SEQ ID NO: 21 |
|  | HCDR3 | SEQ ID NO: 25 | LCDR3 | SEQ ID NO: 53 |
| HAB-9001 | HCDR1 | SEQ ID NO: 17 | LCDR1 | SEQ ID NO: 20 |
|  | HCDR2 | SEQ ID NO: 52 | LCDR2 | SEQ ID NO: 21 |
|  | HCDR3 | SEQ ID NO: 27 | LCDR3 | SEQ ID NO: 22 |

Example 4. Preparation of Humanized Antibodies

1. Molecular Cloning of Humanized Antibodies

Codon optimization was performed against the designed humanized antibody sequences to result in the human codon-preferred coding gene sequences. VH/VK gene fragment of each antibody was constructed with the designed PCR primers, and then was introduced into the expression vector pHr (harboring a signal peptide and constant region gene (CH1-FC/CL) fragment) by homologous recombination to construct a plasmid expressing full length of humanized antibody VH-CH1-FC-pHr/NK-CL-pHr. The correct clones were verified by sequencing, wherein, for HAB-2401, the nucleotide sequence encoding the heavy chain was shown in SEQ ID NO: 54, the nucleotide sequence encoding the light chain was shown in SEQ ID NO: 55; for HAB-3601, the nucleotide sequence encoding the heavy chain was shown in SEQ ID NO: 56, the nucleotide sequence encoding the light chain was shown in SEQ ID NO: 57; for HAB-5101, the nucleotide sequence encoding the heavy chain was shown in SEQ ID NO: 58, the nucleotide sequence encoding the light chain was shown in SEQ ID NO: 59; and for HAB-9001, the nucleotide sequence encoding the heavy chain was shown in SEQ ID NO: 60, the nucleotide sequence encoding the light chain was shown in SEQ ID NO: 61.

2. Expression and Purification of Humanized Antibodies

HEK293E cells were transfected with the plasmids expressing antibody heavy and light chains respectively at a ratio of 1:1.5. 6 days after transfection, the expression supernatant was collected, centrifuged at high speed to remove impurities, and purified with Protein A column. The column was washed with PBS until the A280 reading dropped to the baseline. The target proteins were eluted with 100 mM acetic acid, pH3.0, and neutralized with 1M Tris-HCl, pH8.0. The eluted samples were properly concentrated and then further purified with gel chromatography Superdex200 (GE) pre-equilibrated with PBS to remove aggregates. The monomer peaks were collected and aliquoted for use.

The performance and effect of the present disclosure were verified by the following biochemical tests or in vivo pharmacological test:

Test Example 1. Affinity of Abeta Antibodies Detected by BIAcom Assay

The affinity of an antibody to Aβ1-42 fibrils was detected by the method of amino coupling. Aβ1-42 fibrils was coupled to CM5 biosensing chip (200 RU), and then the antibody molecules were allowed to flow through the surface of the chip. The reaction signals were detected in real time with Biacore T200 instrument to generate a binding and dissociation curve. At the end of each experimental cycle, after the dissociation was completed, the biosensor chip was washed and regenerated with 10 mM Glycine-HCl (pH 1.5). The positive antibody, Aducanumab, was prepared according to the sequence information about Aducanumab released by WHO (see WHO Drug Information, Vol. 28, No. 3, 2014), and the preparation method was described in Example 4 of the present disclosure.

The affinity of an antibody to Aβ1-42 monomer was detected by capturing antibody on the chip. IgG was affinity-captured onto Protein A biosensing chip, and then the antigen Aβ31-42 monomer was allowed to flow through the surface of the chip. The reaction signals were detected in real time with Biacore T200 instrument to generate a binding and dissociation curve. At the end of each experimental cycle, after the dissociation was completed, the biosensor chip was washed and regenerated with 10 mM Glycine-HCl (pH1.5).

The experimental results were shown in Table 4. HAB-2401, HAB-5101, HAB-3601 and HAB-9001 have affinity to Aβ1-42 fibrils ranging from $10^{-8}$ to $10^{-10}$M, of which HAB-9001 has the strongest affinity, which is 2 orders of magnitude stronger than that of Aducanumab. HAB-2401, HAB-5101, HAB-3601 and HAB-9001 have affinity to Aβ1-42 monomer ranging from $10^{-7}$ to $10^{-8}$M, of which HAB-9001 has the strongest affinity, which is 2 orders of magnitude stronger than that of Aducanumab. All of the four test antibodies have affinity stronger than that of the positive antibody, Aducanumab.

TABLE 4

Affinity of antibodies to Aβ1-42 fibrils and Aβ1-42 monomer

| | Affinity (M) | |
|---|---|---|
| Antibody | Aβ1-42 fibrils | Aβ1-42 monomer |
| Aducanumab | 7.52E−08 | 3.20E−06 |
| HAB-2401 | 1.17E−08 | 2.29E−07 |
| HAB-5101 | 1.22E−09 | 3.33E−07 |
| HAB-3601 | 5.45E−08 | 2.62E−07 |
| HAB-9001 | 2.13E−10 | 2.79E−08 |

Test Example 2 Effect of Anti-Abeta Antibodies on Blocking the Aggregation of Aβ1-42 Monomer into Aβ1-42 Fibrils Effect of Anti-Abeta antibodies on inhibiting the aggregation of Aβ1-42 monomer into Aβ1-42 fibrils was detected by ThT assay. ThT (Thioflavin T, thioflavin) is a type of fluorescent dye and is typically used for in vitro identification of Aβ fibrils, as the fluorescence signals at the excitation wavelength of 450 nm and emission wavelength of 482 nm will be significantly enhanced once it combines with β-sheet rich protein (such as Aβ amyloid deposit). The specific experimental procedures of the ThT assay were indicated as follows. 0.5 mg human Aβ1-42 (GenScript, CAT #RP10017) was added into 250 μl 10 mM NaOH, completely dissolved and then added into an equal volume of pre-cooled 2×PBS for neutralization. Aβ1-42 monomer solution with a concentration of 1 mg/ml was prepared and the diluted with ddH$_2$O to 0.25 mg/ml. Aβ1-42 monomer (10 μl/well, 0.25 mg/ml) was mixed with 20 μM ThT (sigma, CAT #T3516) and added into a black 384-well plate (Corning, CAT #4514), and a well without adding Aβ1-42 monomer was served as negative control. Then gradiently diluted antibodies (starting from 1 mg/ml, 2-fold gradient dilution, 10 μl/well) were added into the above mixture, incubated at 37° C. for 24h. Fluorescence signals were read at excitation wavelength of 440 nm and emission wavelength of 485 nm by using FlexStation3 microplate reader (Molecular devices).

Figure 1:
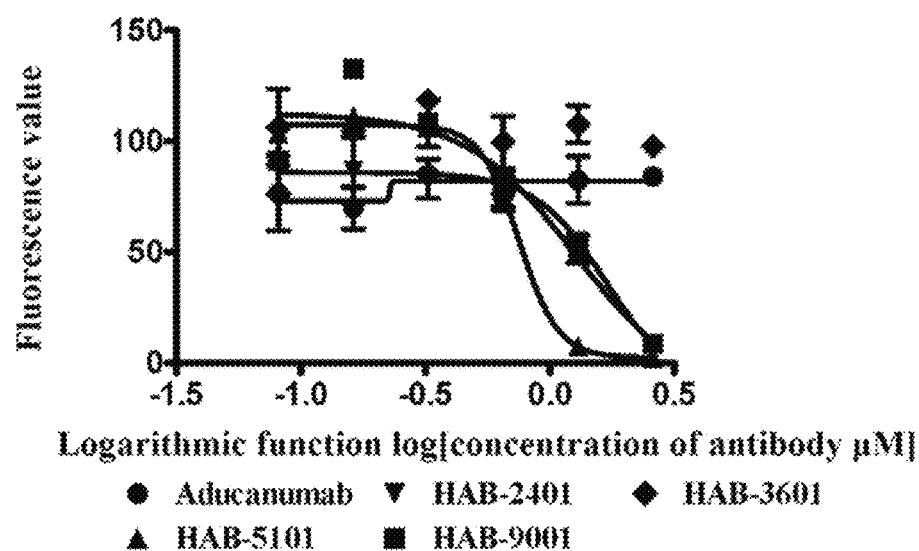
FIG. 1 displays a thioflavin (ThT) fluorescence assay, showing the experimental results of the blocking effect of anti-Abeta antibodies on the aggregation of A$\beta$1-42 monomers into A$\beta$1-42 fibrils.

The experimental results were shown in FIG. 1. All of HAB-2401, HAB-5101 and HAB-9001 can effectively inhibit the aggregation of Aβ1-42 monomers into Aβ1-42 fibrils. Whereas HAB-3601 and Aducanumab do not have such function.

Test Example 3. Protection of Anti-Abeta Antibodies on Rat Primary Neurons

The cerebral cortex was dissected from SD fetal rats with gestational age of 16-18 days, digested with trypsin (Gibco, CAT #25200-072), pipetted and filtered into a single cell suspension, centrifuged, and counted. The cells were diluted with DMEM (Gibco, CAT #10564-029) containing 10% FBS (Gibco, CAT #10099-141) to 1E4 per well (1×10$^4$/well), and plated into 96-well plate (Corning, CAT #3903) coated with PDL (Poly-D-lysine, polylysine) (Sigma, CAT #P0899). After incubating overnight in an incubator (37° C., 5% CO$_2$), the medium was exchanged with Neurobasal (Gibco, CAT #21103049)+2% B27 (Gibco, CAT #17504044), and half of the medium was exchanged every 3-4 days. On day 8, 10 μM Aβ1-42 fibrils (GL biochem, CAT #53819) and various concentrations of test antibodies were added. After incubating for 3 days, 30 μl/well of Cell Titer-Glo (Promega, CAT #G7571) was added, and the plate was read with a microplate reader (PerkinElmer, Vector3) with a chemiluminescence method.

Figure 2:
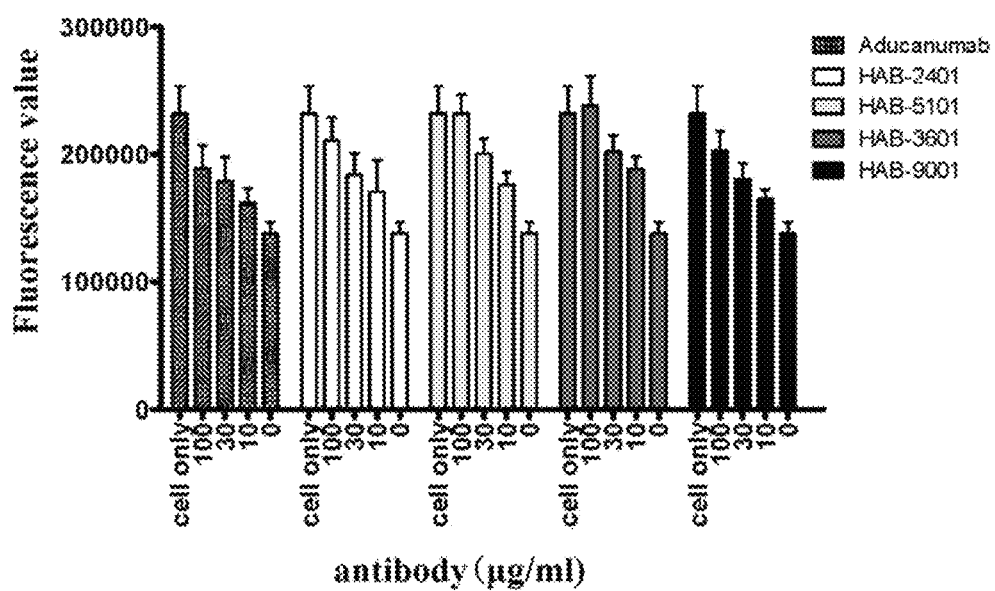
FIG. 2 displays an assay of protection on primary cortical neurons, showing the experimental results of the protection effect of anti-Abeta antibodies on rat primary neurons.

The experimental results were shown in FIG. 2. HAB-2401, HAB-5101, HAB-3601, HAB-9001 and the positive antibody Aducanumab can protect primary neuronal cells from the toxicity of Aβ fibrils, and a dose-dependent effect was observed in the concentration range of 10 to 100 μg/ml.

Test Example 4. Anti-Abeta Antibodies Promote the Phagocytosis of Aβ Fibrils by BV2 Cells BV2 cells in the logarithmic growth phase (FuDan IBS Cell Center, FH0366) were taken and digested with trypsin, centrifuged at 800 rpm for 5 min. The cell density in 24-well plate was adjusted with RPMI 1640 (containing 10% FBS) to 1.2×10$^5$ cells/well/500 μl, shaken thoroughly until forming a single layer of cells, and placed in an incubator at 37° C., 5% CO$_2$ overnight. 16 hours later, 100 μl of gradiently diluted Abeta antibody or negative control (an anti-thrombin antibody against irrelevant target was used as negative control, and the anti-thrombin antibody was produced in accordance with the Preparation Method for H1601-008 as described in WO2017133673A1) was mixed thoroughly with 10 μM fluorescence labeled Abeta fibrils (diluted with 100 μl F-12K basic medium), incubated at 37° C. for one hour, added into a 24-well plate with 500 μl medium removed, and incubated at 37° C., 5% CO$_2$ for 1 hour. The supernatant was removed, and the cells were gently washed three times with PBS pre-cooled at 4° C. And then 0.25% pre-cooled Trypsin-EDTA (1×) was added at 200 μl/well and placed at 4° C. for 20 minutes. The trypsin was neutralized with F-12K medium containing 10% FBS and centrifuged, and then the cells were washed three times with pre-cooled PBS, 100 μl of cells were collected and applied onto Flow Cytometer to read out the FITC fluorescence intensity.

Figure 3:
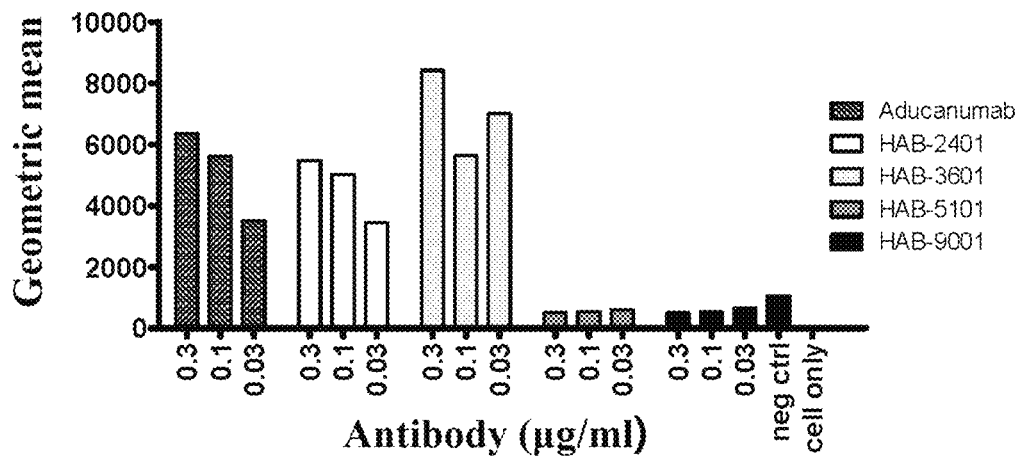

The experimental results were shown in FIG. 3. Both HAB-2401 and HAB-3601 can promote the phagocytosis of Aβ fibrils by BV2 cells, just like the positive antibody Aducanumab. A dose-dependent effect was observed in the concentration range of 0.03 to 0.3 μg/ml.

Test Example 5. Effect of Anti-Abeta Antibodies on Phagocytosis of Aβ Fibrils by Rat Primary Microglia The cerebral cortex was dissected from the neonatal SD rat, ground and filtered to result in a cell suspension. The cells were resuspended in DMEM containing 20% FBS (Gibco, CAT #10099-141), transferred into a T75 culture flask (Corning, CAT #3473) pre-coated with PDL (Sigma, CAT #P0899) and placed in an incubator (37° C., 5% CO$_2$). The medium was exchanged once every 3 days. On day 8, the culture flask was placed on a shaker and shaked at 200 rpm for 1 hour. The supernatant was collected, centrifuged, counted, diluted to 5E4/well (5×10$^4$/well) with DMEM/F12 (GE, CAT #SH30023.01) medium containing 10% FBS, and plated into a 24-well plate. 6 hours later, the medium was exchanged to serum-free DMEM/F12 medium and incubated overnight. On day 9, various concentrations of antibodies or negative control (an anti-thrombin antibody against irrelevant target was used as negative control, and the anti-thrombin antibody was produced in accordance with the Preparation Method for H1601-008 as described in WO2017133673A1) was mixed with 10 μM FITC labeled (Thermo, CAT #A30006) Abeta 1-42 (GL biochem, CAT #53819) respectively, incubated at 37° C. for 30 minutes, and centrifuged to wash off excess antibodies. The mixture of antibody and Abeta was added to the cells and incubated at 37° C. for 30 minutes. The cells were washed twice with PBS (Hyclone, CAT #SH30256.01), and added with trypsin (Gibco, CAT #25200-072), placed in refrigerator at 4° C. for 10 minutes to digest the cells. And then serum was added to terminate the reaction, the cells were collected after removing the supernatant by centrifugation, pre-cold PBS was added and the supernatant was removed by centrifugation, and the cells were washed twice with PBS. The FITC fluorescence intensity was read out by flow cytometer (BD, Verse).

Figure 4:
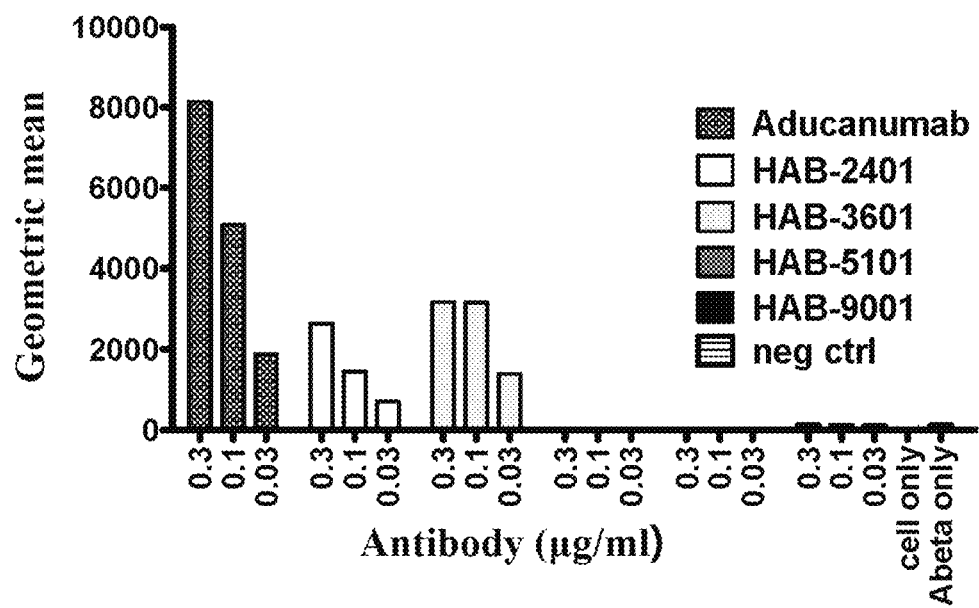
FIG. 4 shows the experimental results of the effect of anti-Abeta antibodies on the phagocytosis of A$\beta$ fibrils by rat primary microglial cells.

The experimental results were shown in FIG. 4. In the experiment of phagocytosis by the rat primary microglia, HAB-2401 and HAB-3601 can promote the phagocytosis of Aβ fibrils by primary microglia, just like the positive antibody Aducanumab. A dose-dependent effect was observed in the concentration range of 0.03 to 0.3 μg/ml.

Test Example 6. In Vivo Pharmacological Test of Anti-Aβ Antibodies

5×FAD (Five Familial AD mutations) Alzheimer's mouse model was used to evaluate the in vivo efficacy of anti-Aβ antibodies. Five familial gene mutations of APP and PS1 genes, including three mutations on APP gene (namely Swedish mutation (K670N, M671L), Florida mutation (I716V) and London mutation (V717I)) and two mutations on the PS1 gene (namely M146L and L286V) were overexpressed in 5×FAD mice. Therefore, compared to wild-type mice (WT), 5×FAD mice displayed obvious impairments in cognitive function and memory and had significant Aβ plaque deposit in brain tissue. This test example was designed to evaluate the efficiency of the test antibodies in improving the mouse's cognitive competence and reducing Aβ plaque deposition by testing the improvement of mouse's behavior, including the ability of nest building, and spatial memory (spatial memory in morris water maze), as well as by testing the changes in the content of Aβ plaques in the brain tissue.

5×FAD mice were provided by Shanghai ChemPartner Co., Ltd. Three-month-old mice were selected and kept at a room temperature of 23±2° C., with 12/12 hours of light/dark cycle, food and water ad libitum. The test antibodies were all in the human-mouse chimeric form, that is, the constant region(s) of the heavy and light chains were replaced with mouse constant region(s) to avoid ADA (anti-drug antibody) caused by long-term administration of antibodies. Six groups (n=15 each group) were included in the experiment, 4 groups of antibodies to be tested, one group of Aducanumab as positive control and one group of PBS as negative control. HAB-2401 and HAB-3601 were in mIgG1 chimeric form, whereas HAB-5101, HAB-9001 and Aducanumab were in mIgG2a chimeric form, and they were referred to as HAB-2401-Ch, HAB-3601-Ch, HAB-5101-Ch, HAB-9001-Ch and Aducanumab-Ch, respectively. HAB-2401-Ch and HAB-3601-Ch were produced by fusing the heavy chain variable region and light chain variable region of HAB-2401 and HAB-3601 to the heavy chain constant region of mIgG1 (the amino acid of the heavy chain constant region of mIgG1 was shown in SEQ ID NO: 62) and the light chain constant region of mIgG1 (the amino acid sequence of the light chain constant region of mIgG1 was shown in SEQ ID NO: 63), respectively; HAB-5101-Ch, HAB-9001-Ch and Aducanumab-Ch were produced by fusing the heavy chain variable region and light chain variable region of HAB-5101, HAB-9001 and Aducanumab to the heavy chain constant region of mIgG2a (the amino acid sequence of the heavy chain constant region of mIgG2a was shown in SEQ ID NO: 64) and the light chain constant region of mIgG2a (the amino acid sequence of the light chain constant region of mIgG2a was shown in SEQ ID NO: 65), respectively. The method for preparation of the antibody was described in Example 4 of this disclosure. The antibody was i.p. administered with 15 mpk (mg/kg, milligram per kilogram of body weight) once a week, and the administration was performed at 13:00 to 16:00, for 12 weeks in total.

All 5×FAD mice were given an additional injection of the corresponding antibody after the behavioral test (Test Example 8). Mice were divided into three batches, 5 mice in each group. Samples were taken at 24 h, 72 h and 7 day after the additional dose, in order to quantitatively detect the content of antibodies penetrating the BBB at different time points after antibody treatment. While with respect to the detection of Aβ deposit (Test Example 9) and cytokines (Test Example 10), for the groups of the same antibody, all of the samples taken at various time points after additional dose were pooled together for data processing.

Test Example 7. Testing Mouse's Ability of Nest Building

Nest building is mouse's instinct, and it is typically used as an experimental method to measure the social behavior of mouse. It has been reported that transgenic mice overexpressing APP, such as Tg2576, APPswe/PS1, 3×Tg-AD, 5×FAD (Transl Psychiatry. 2015 May 5; 5:e562), showed impairment in the ability of nest building to varying degrees. This test example is to evaluate the effect of the test antibodies on improving the social behavior of 5×FAD transgenic mice by scoring the nest building ability of mice with multiple parameters.

The specific procedures of mouse's nest building was described below. At about 16:00 on the first day of the experiment, a piece of compressed cotton was placed in each cage, and each mouse was kept in a separate cage. The compressed cotton was weighed before placing in the cage (Weight 1), and the breeding environment remained unchanged. At 10 o'clock the next morning, the mice were taken out and returned to the original cages. The shape of the nest and the position of cotton pieces were kept unchanged. First, a digital camera was used to take pictures of the nests made by the mice (a front view and a side view to reflect the true shape and height of the nest). The cotton which has not been torn into pieces was picked up and weighed (Weight 2). The percentage of cotton left was calculated. Based on the pictures, according to the shape, height of the nest and the degree to which the cotton has been torn, average score for each animal was obtained from three independent scores provided at parallel, in accordance with the scoring criteria, the scores can be adjusted appropriately based on specific situation. The scoring criteria was shown in Table 5:

TABLE 5

Scoring criteria for the nest building ability of mice

Figure 5:
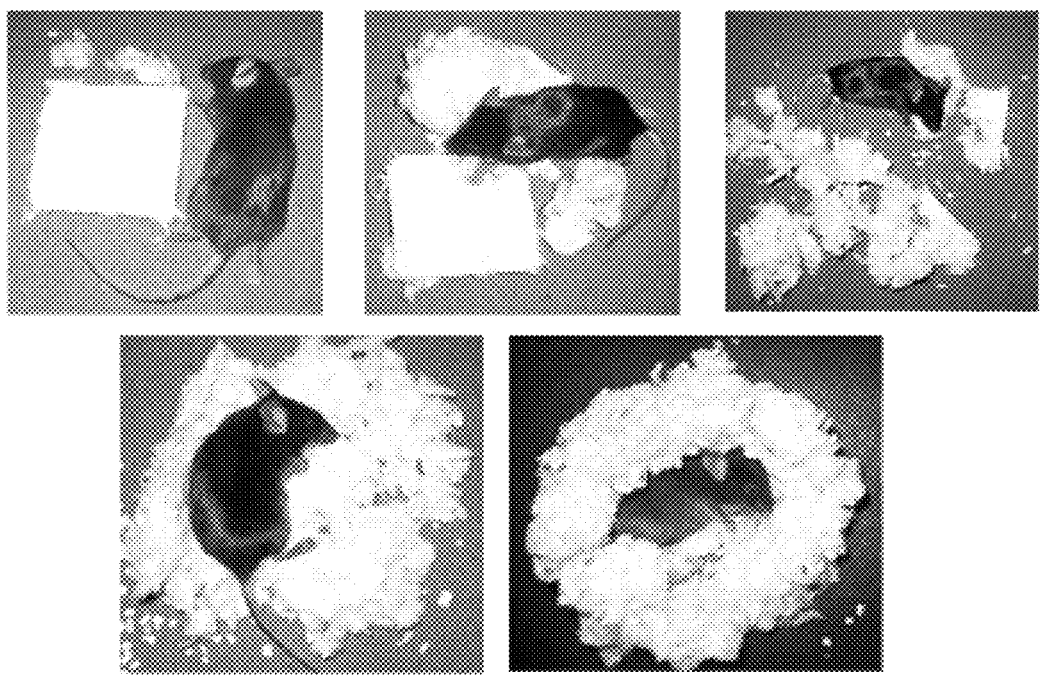
FIG. 5 is representative picture for scoring the ability of mice to make a nest.

| The shape, height of the nest and the degree to which the cotton has been torn | Score |
|---|---|
| The cotton piece remained almost intact (the cotton left over 90%), as shown in FIG. 5; | 1 |
| A small part of the cotton piece has been torn into pieces, most of the cotton piece remained intact, and the amount of the cotton left was between 50% to 90%, as shown in FIG. 5; | 2 |
| Most of the cotton piece has been torn into pieces (50%-90%), however the pieces of the cotton were not gathered at the corner of the cage to form a preliminary shape of the nest; instead, the pieces of cotton were scattered on the bottom of the cage, as shown in FIG. 5; | 3 |
| Most of the torn cotton pieces (more than 90%) were gathered at the corner of the cage and basically form the shape of a nest, but the height of the nest did not exceed 50% of the height of the mouse body, as shown in FIG. 5; | 4 |
| The cotton was almost completely torn (more than 90% have been torn), in a shape of a crater-like pit, and the height of the nest exceeded 50% of the height of the mouse body, as shown in FIG. 5. | 5 |

Figure 6:
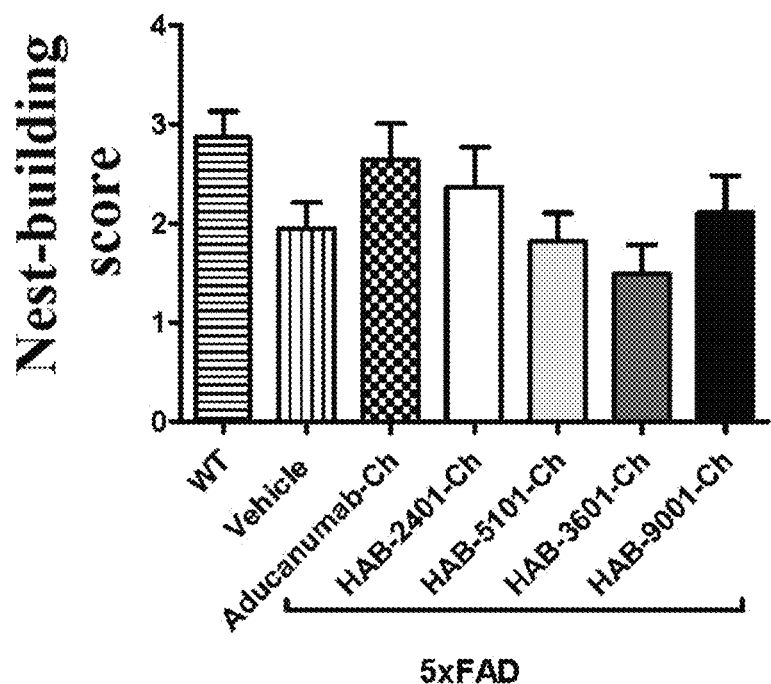
FIG. 6 displays a nesting experiment, the bar graph showing the effect of anti-Abeta antibodies on improving the social behavior of 5×FAD transgenic mice.
Figure 7:
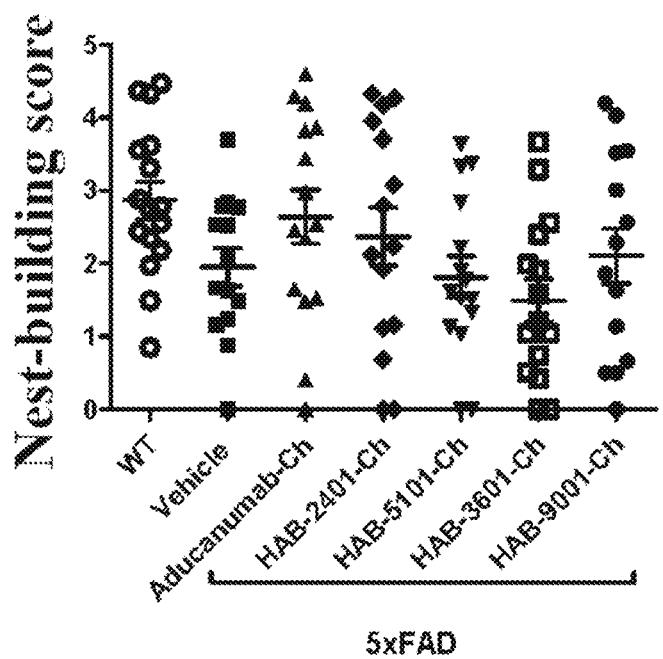
FIG. 7 displays a nesting experiment, the scatter diagram showing the effect of anti-Abeta antibodies on improving the social behavior of 5×FAD transgenic mice.

Pictures of each animal were analyzed by using Lasso tool in Photoshop CS4 software package to calculate the nest area ratio (percentage of the nest area to the total area of the scattered cotton pieces). The comprehensive score of the three parameters (cubic score) was calculated according to the formula below:

Comprehensive score of the three parameters=Percentage of cotton left×Percentage of nest area×Average score The test results were shown in FIG. 6 and FIG. 7. There was some difference between Vehicle (solvent blank control) and WT (wild-type), which reflects the experimental window of the test. While Aducanumab-Ch, HAB-2401-Ch and HAB-9001-Ch groups showed some improvement tendency compared to the vehicle group.

Test Example 8 Water Maze Behavioral Test
(Morris Water Maze)

The water maze experiment is a behavioral test commonly used in the field of neurobiology to evaluate the spatial learning and memory ability of rodents. In such experiment, spacial cues around the swimming pool were used to guide rodents to find and remember the escape platform hidden under the water in the swimming pool by trainings.

Figure 8:
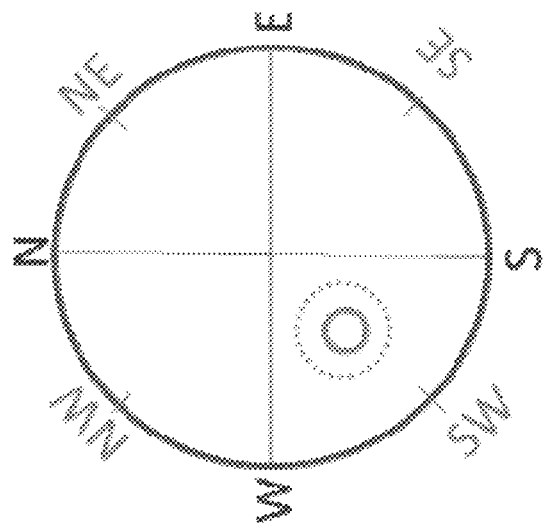
FIG. 8 shows a schematic diagram of the water maze. The solid circle and the dotted circle represent the location of the platform and the platform zone, respectively.

The Morris water maze consisted of a white, non-toxic and odorless plastic circular pool with a diameter of 120 cm and a height of 50 cm and a transparent perspex platform. The platform was 31 cm high, and the top surface of the platform had a diameter of 8.5 cm. The pool was filled with water until the water surface was 1cm above the platform. The pool was equally divided into four quadrants, NE, SE, SW and NW, and N, NE, E, SE, S, SW, W and NW were marked at eight points equally divided the outer circle of the round pool. The platform was located in the center of the SW quadrant, with 30 cm distance to the center of the circle and 30 cm distance to the pool wall (a schematic diagram of the water maze was shown in FIG. 8). The installed camera device was connected to the computer and monitor. The round pool was placed in a well-lit laboratory. Obvious visual cues were decorated at NE, SE, SW and NW markers. Before the experiment, an appropriate amount of white plastic particles were sprinkled in the water to make it evenly cover the water surface, and the water temperature was maintained at 23.0±2.0° C. The water was changed every 5 days.

The following modules were included in water maze experiment: flag training, hidden platform and probe test.

8.1. Flag Training

A flag above the water was placed on the platform to guide animals. Each experimental animal was put into the water (facing the wall of the pool) at the N point, and video tracking and recording were started at the same time, for 60 seconds. If the animal failed to board the platform within 60s, it would be manually guided to the platform and allowed to stay for 20s before being removed from the maze; if the animal found the platform within 60s but stayed on the platform for less than 20s, after 60s-training was ended, it would be forced to stay on the platform for 20s before being removed from the maze; if the animal found the platform within 60s and stayed on the platform for 20s, it would be removed from the maze. After training, each animal was dried with a towel and returned to the cage. After all the animals had been trained, a new round of the same training was re-started. In this way, each animal was trained 4 times within one day.

8.2. Hidden Platform

The platform was hidden about 1cm below the water surface. The animals were trained 4 times a day for a total of 12 days. The location at which the mice were put into water was shown in FIG. 8. During each training, the animals were placed facing the pool wall, and video tracking and recording were started at the same time. Each training lasted for 60s. If the animal failed to found the platform within 60s, it would be manually guided to the platform and allowed to stay for 15s before being removed from the maze; if the animal found the platform within 60s but stayed on the platform for less than 15s, after 60s-training was ended, it would be forced to stay on the platform for 15s before being removed from the maze; if the animal found the platform within 60s and stayed on the platform for 15s, it would be removed from the maze. After training, each animal was dried with a towel and returned to the cage. After all the animals had been trained, a new round of training was re-started, with different location at which the animal was put into the water.

8.3 Probe Test 24 hours after the last training on day 12, the platform under water was removed for probe test. The animal was put into the water (facing the wall of the pool) at the NE point, and video tracking and recording were started at the same time. 60s later, the tracking was ended. The animal was removed from the pool, dried with a towel and returned to the cage. The animal's track was analyzed with Noldus Ethovision software.

8.4. Results of Water Maze Experiment

Figure 9:
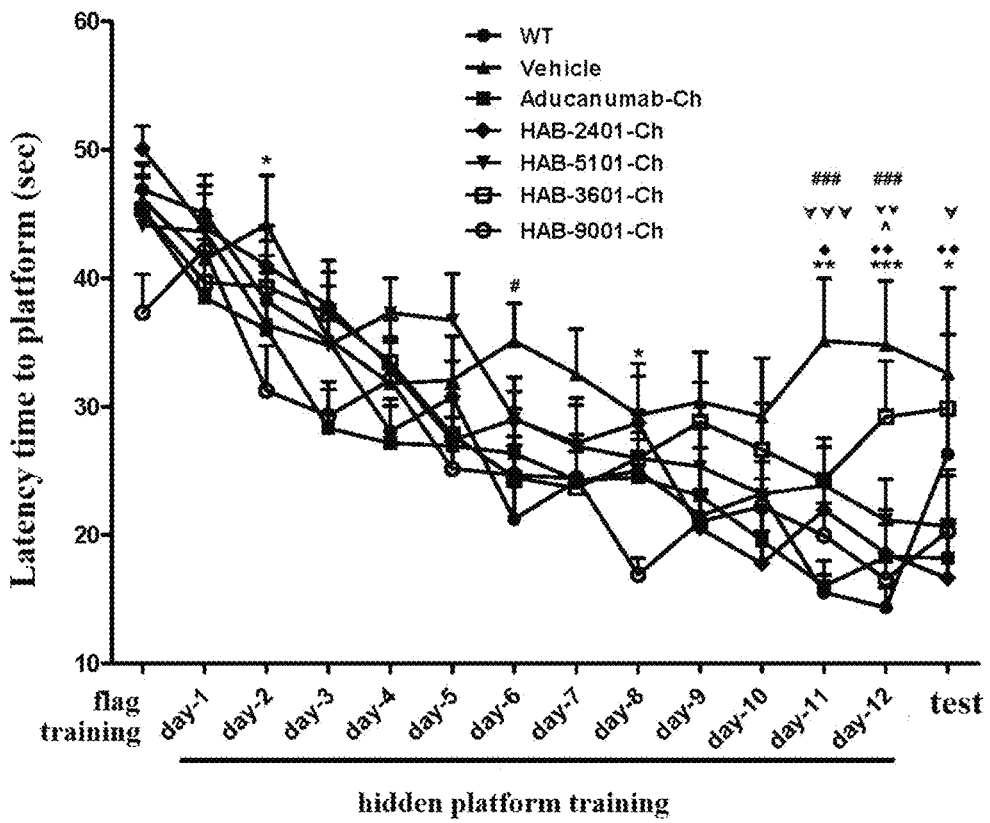
FIG. 9 displays learning curves for the water maze experiment; showing the curve results of the hidden platform training and learning. Two way ANOVA refers to two-way analysis of variance; The analysis results are as follows.

The learning curve of the hidden platform training was shown in FIG. 9. The results showed that between the 5×FAD Tg mouse vehicle (solvent blank control) group and the WT group, a significant difference was observed on day 6, and very significant differences were observed on day 10 and day 11 of the hidden platform training, and such difference tended to be stable, indicating that there is difference in the spatial memory ability between 5×FAD transgenic mice and wild-type mice in the behavioral test. Such difference is the basis of testing the test drugs; from day 1, the group of positive control drug Aducanumab-Ch always displayed shorter latency time to the platform than the vehicle group, on day 11, a significant difference was observed, indicating that Aducanumab-Ch showed excellent efficacy in this experiment; Similarly to Aducanumab-Ch group, HAB-2401-Ch, HAB-5101-Ch and HAB-9001-Ch showed significant difference on day 11 and 12, indicating that like Aducanumab-Ch, the three drugs can significantly improve the spatial memory and cognitive competence of mice.

In the Probe test, we evaluated several experimental parameters, including latency to platform, latency to platform zone, count of crossing the platform or the platform zone, duration on platform & duration on platform zone and ACI index.

The results of latency to the platform were shown in FIG. 10A There was a certain difference between the WT and the vehicle group, which is an experimental window. (For WT group, the latency to platform in probe test was longer than that in the flag training, which might be caused by experimental variation, because only one test was performed in the probe test, whereas four tests have been performed in the flag training). The results of HAB-2401-Ch, HAB-5101-Ch and HAB-9001-ch were comparable to that of Aducanumab-Ch group, and showed a shorter duration than the vehicle group.

The results of the latency to platform zone were shown in FIG. 10B. WT group displayed about three times significant difference when compared to vehicle group. Aducanumab-Ch group showed a significant difference when compared to the vehicle group, while the result of Aducanumab-Ch group was close to that of the WT group, indicating that the positive molecules can significantly improve the memory of 5×FAD mice. All of the four test antibodies displayed significant differences when compared to Vehicle group, among which HAB-9001-Ch showed even better efficacy than Aducanumab-Ch.

The experimental results of the count of crossing the platform or the platform zone were shown in FIG. 10C and FIG. 10D, the experimental results of the duration on platform & duration on platform zone were shown in FIG. 10E and FIG. 10F, and the experimental results of ACI index were shown in FIG. 10G. In the probe test, the platform has been removed, and the mice's memory of the platform is theoretically positively correlated with these parameters. As for these five parameters, there was a certain difference between the WT group and vehicle group, indicating the experimental window of the experimental results. Compared to the vehicle group, Aducanumab-Ch showed tendency of improvement. Compared to the vehicle group, HAB-2401-Ch, HAB-5101-Ch and HAB-9001-Ch all showed different degrees of improvement, and HAB-9001-Ch showed the best performance.

In summary, in the probe test, compared to the vehicle group, HAB-2401-Ch, HAB-5101-Ch and HAB-9001-Ch displayed different degrees of improvement in latency to platform, latency to platform zone, duration on platform, duration on platform zone, count of crossing the platform, count of crossing the platform zone and the ACI index, suggesting that these three test antibodies can significantly improve the spatial memory and cognitive competence of the 5×FAD Alzheimer mouse model.

Test Example 9. Detection of Aβ Deposit

All samples were taken from the mice used for the behavioral test (Test Example 8). Each mouse was perfused with PBS (pH 7.4) and the brain was collected. The left hemisphere was immersed into 4% PFA immediately and fixed for 72 hours, and the right hemisphere was dissected on ice to collect the frontal cortex and hippocampus, weighed separately, then quickly frozen in liquid nitrogen, and stored in a refrigerator at −80° C. for subsequent sample processing.

The specific procedures of homogenizing the right hemisphere were as follows: the test tissue was weighted and transferred into a homogenization tube, and added with 10 times-volume of diethylamine lysate (50 mM NaCl, 0.2% DEA containing protease inhibitors). That is, 10 mg of tissue was added to 100 μl of lysis solution, homogenized with a homogenizer, and ultrasonicated in ice water for 15-20 seconds. The homogenate was transferred into a centrifuge tube, centrifuged at 100,000×g at 4° C. for 30 min. The resulting supernatant containing soluble Aβ was collected and stored at −80° C. 10 times-volume of guanidine hydrochloride lysis solution (5M GuHCl in PBS) was added into the centrifuge tube, the pellet was resuspended and sonicated in ice water for 15-20 seconds. The sample was centrifuged at 100,000×g at 4° C. for 30 min. The resulting supernatant containing insoluble Aβ was collected and stored at −80° C.

Aβ deposit in brain tissue homogenate was detected by ELISA method (Human Amyloid beta (aa1-40) Quantikine ELISA Kit: R&D systems, DAB140B; Human Amyloid beta (aa1-42) Quantikine ELISA Kit: R&D systems, DAB142). First, the insoluble components in the brain homogenate (that is, the sample to be tested) and standard were diluted with diluent; the pre-coated plate was washed with washing buffer; the diluted standard and samples were added; the plate was sealed and incubated at 4° C. for 2 hours; the plate was washed with washing buffer for 3-4 times; pre-cold secondary antibody was added; the plate was sealed and incubated at 4° C. for 2 hours; the plate was washed 3-4 times with washing buffer; substrate chromogenic solution was added and incubated at room temperature for 30 minutes; stop solution was added and OD450 was read on microplate reader.

The results of ELISA test were shown in FIG. 11A-11D, Vehicle (solvent blank control) group displayed significant Aβ1-40 and Aβ1-42 deposit compared to WT group, indicating that Aβ deposit was over-expressed in 5×FAD mouse brain tissue. Compared to the vehicle group, a tendency of reduced Aβ1-40 and Aβ1-42 was observed in Aducanumab-Ch. Among the four tested antibodies, HAB-3601-Ch had the best performance and had a tendency of reduced insoluble Aβ1-40 (hippocampus insoluble Aβ1-40) and insoluble Aβ1-42 (hippocampus insoluble Aβ1-42) compared to the vehicle.

The procedures for immunohistochemical staining of the left hemisphere tissue were as follows. Dehydration of the isolated brain: the brain was fixed with 4% PFA for 72 hours, then put into 30% sucrose solution for dehydration, placed in a refrigerator at 4° C. overnight, and the dehydration procedure was repeated once; the tissues were embedded: isopentane was placed in dry ice for a few minutes to make the liquid in isopentane to reach −70° C.; the brain tissue was dried with blotting paper and put into isopentane to be frozen for a few seconds after the redundant portion was removed, and then the brain tissue was taken out from isopentane, dried and embedded in the embedding box with OTC (Embedding agent), and then the embedding box was placed on dry ice to make the OTC solidified. The embedded brain tissue was stored in the refrigerator at −80° C.; Sectioning: the brain tissue was cut in a sagittal section in a cryostat, 20 μm per slice; inactivation of endogenous peroxidase: the brain slice was rinsed 3 times in PBS, 5 minutes each time, incubated with 0.3% $H_2O_2$ (prepared with PBS) for 10 minutes; permeabilization: the brain slice was rinsed 3 times in PBS, 5 minutes each time, incubated with TBST (TBS containing 0.25% Triton X-100) 3 times, 5 min each time; blocking: incubated with 0.3% Triton X-100 and 5% BSA in PBS for 1 h; incubation with the primary antibody: the primary antibody 3D6 was diluted with 2% BSA in TBST to the working concentration of 10 μg/ml, and the brain slice was put into the working solution of the primary antibody and incubated overnight at 4° C.; incubation with the secondary antibody: the brain slice was rinsed in TBST three times, 5 minutes each time, the secondary antibody was diluted with TBST containing 2% BSA to obtain working concentration of 5 μg/ml, the brain slice was incubated in the working solution of the secondary antibody for 1 h; color was developed: the brain slice was rinsed in TBST 3 times, 5 minutes each time, and put into the color development solution in dark for 5 minutes, and then immersed into pure water twice to stop the development reaction; mounting: the brain slice was put into and out of PBS, dried, immersed in pure water to remove the salt, dried, and fixed with gradient concentrations of ethanol (75%, 95%, absolute ethanol), mounted with resin, and dried; scanning and quantitative analysis: the slice wad scanned with digital slice scanner (Hamamatsu Nanozoomer S210) to generate the scanning images of the slice. For each brain slice picture, cortex and hippocampus regions were firstly indicated in accordance with mouse cerebral coordinate, and then Aβ positive signal areas were indicated by BIOTOPIX™ Analysis system software. Finally, the ratio of positive signals was calculated for the cortex and hippocampus, respectively. That is, the ratio of Aβ positive signals in the cortex=the area of Aβ positive signals in the cortex/total area of the cortex; the ratio of Aβ positive signals in the hippocampus=the area of Aβ positive signals in the hippocampus/total area of the hippocampus.

The experimental results of IHC detection were shown in FIG. 12 and FIG. 13. Compared to the WT group, the vehicle group displayed obvious deposit of Aβ1-40 and Aβ1-42, which is consistent with the ELISA assay. Compared to the vehicle group, HAB-3601-Ch, HAB-9001-Ch and Aducanumab-Ch can significantly reduce Aβ deposit, suggesting that HAB-3601-Ch and HAB-9001-Ch can significantly reduce Aβ deposit, just like Aducanumab-Ch.

Test Example 10. Effect of Antibodies on the Release of Cytokines in Brain Tissue Samples used in this test example were the soluble component from the brain homogenate in Test Example 9, and the detection method to be used was a highly sensitive electrochemiluminescence analyzer MSD (Meso Scale Discovery). Specific experimental procedures were described in the product manual (U-PLEX Biomarker Group (mouse) Multiplex assays kit: MSD, N05235A-1). Briefly, biotinylated capture antibody for each cytokine was linked to each linker of U-PLEX, reacted at room temperature for 30 minutes, and then the reaction was terminated; the prepared U-PLEX-linked antibody solutions were mixed and coated onto U-PLEX plate, incubated at room temperature with shaking for one hour or 4° C. overnight; the standard and test samples (i.e., the soluble components in the brain tissue homogenate) were diluted according to the manual; the coated plate was washed with PBST or 1×MSD washing buffer (1×MSD washing reagent) for 3 times, added with 25 µl sample diluent, and 25p0 diluted standard and samples to be tested, and the plate was sealed and incubated at room temperature with shaking for 1 hour. The coated plate was washed with PBST or 1×MSD washing buffer 3 times, added with 50 µl of the diluted detection antibody mixture, and the plate was sealed and incubated with shaking at room temperature for 1 hour. The coated plate was washed 3 times with PBST or 1×MSD washing buffer, and then added with 2×Read buffer reagent. Finally, the place was read on the MSD instrument.

The experimental results were shown in FIG. 14A to FIG. 14D and FIG. 15A to FIG. 15F. The levels of all the cytokines such as TNFα, IFN-γ, IL1 β, IL2, IL6, IL12p70, IL4, IL10, MCP-1 and KC were very low and almost reached the lower limit of the detection method. There were obvious differences between individual mice, so there was no significant difference between the groups. In summary, the four test antibody groups did not show higher level of cytokines when compared to positive control Aducanumab, indicating that test antibodies are safe.

The invention claimed is:

1. An anti-Abeta antibody or antigen-binding fragment thereof, wherein the anti-Abeta antibody specifically binds to human Abeta and comprises a heavy chain variable region comprising antibody heavy chain HCDR1, HCDR2 and HCDR3 regions and a light chain variable region comprising antibody light chain LCDR1, LCDR2 and LCDR3 regions, wherein the HCDR1 in comprises the amino acid sequence of SEQ ID NO: 17, the HCDR2 comprises the amino acid sequence of SEQ ID NO: 18 or 52, and the HCDR3 comprises the amino acid sequence of SEQ ID NO: 27, and the LCDR1 comprises the amino acid sequence of SEQ ID NO: 20, the LCDR2 comprises the amino acid sequence of SEQ ID NO: 21, and the LCDR3 comprises the amino acid sequence of SEQ IDNO: 22.

2. The anti-Abeta antibody or antigen-binding fragment thereof according to claim 1, wherein the antibody is a murine, chimeric or humanized antibody.

3. The anti-Abeta antibody or antigen-binding fragment thereof according to claim 2, wherein the antibody is a murine antibody, and comprises a heavy chain variable region comprising the amino acid sequence of SEQ ID NO: 9, or having at least 95% sequence identity to the amino acid sequence SEQ ID NO: 9 and comprising HCDRs 1-3 of SEQ ID NOs: 17, 18 and 27 respectively; and a light chain variable region comprising the amino acid sequence of SEQ ID NO: 10, or having at least 95% sequence identity to the amino acid sequence of SEQ ID NO: 10 and comprising LCDRs 1-3 of SEQ ID NOs: 20-22 respectively.

4. The anti-Abeta antibody or antigen binding fragment thereof according to claim 3, wherein the heavy chain variable region comprises the amino acid sequence of SEQ ID NO: 9 and the light chain variable region comprises the amino acid sequence of SEQ ID NO: 10.

5. The anti-Abeta antibody or antigen-binding fragment thereof according to claim 2, wherein the antibody comprises a heavy chain variable region comprising the amino acid sequence of SEQ ID NO: 50, or having at least 90% sequence identity to the amino acid sequence of SEQ ID NO: 50 and comprising HCDRs 1-3 of SEQ ID NOs: 17, 18 and 27 respectively, or HCDRs1-3 of SEQ ID NOs: 17, 52 and 27 respectively; and a light chain variable region comprising the amino acid sequence of SEQ ID NO: 51, or having at least 90% sequence identity to the amino acid sequence of SEQ ID NO: 51 and comprising LCDRs 1-3 of SEQ ID NOs: 20-22 respectively.

6. The anti-Abeta antibody or antigen-binding fragment thereof according to claim 2, wherein the antibody is a humanized antibody and comprises an antibody heavy chain variable region comprising HCDR1 having the amino acid sequence of SEQ ID NO: 17, HCDR2 having the amino acid sequence of SEQ ID NO: 18 or 52 and HCDR3having the amino acid sequence of SEQ ID NO: 27; and an antibody light chain variable region comprising LCDR1 having the amino acid sequence of SEQ ID NO: 20, LCDR2 having the amino acid sequence of SEQ ID NO: 21 and LCDR3 having the amino acid sequence of SEQ ID NO: 22.

7. The anti-Abeta antibody or antigen-binding fragment thereof according to claim 1, wherein the antibody comprises constant region(s); and wherein the antibody heavy chain constant region is the amino acid sequence of SEQ ID NO: 42, and the antibody light chain constant region is the amino acid sequence of SEQ ID NO: 43.

8. The anti-Abeta antibody or antigen-binding fragment thereof according to claim 7, wherein the antibody comprises a heavy chain having the amino acid sequence of SEQ ID NO: 40, and a light chain having the amino acid sequence of SEQ ID NO: 41.

9. The anti-Abeta antibody or antigen-binding fragment thereof according to claim 1, wherein the antigen-binding fragment is selected from the group consisting of Fab, Fab', F(ab')2, scFv, and dsFv.

10. A pharmaceutical composition comprising:
the anti-Abeta antibody or antigen-binding fragment thereof according to claim 1, and one or more pharmaceutically acceptable carrier(s), excipient(s) or diluent(s).

* * * * *

```
                          SEQUENCE LISTING

<160> NUMBER OF SEQ ID NOS: 73

<210> SEQ ID NO 1
   <211> LENGTH: 40
   <212> TYPE: PRT
   <213> ORGANISM: Artificial Sequence
   <220> FEATURE:
   <221> NAME/KEY: domain
   <223> OTHER INFORMATION: Abeta 1-40 amino acid sequence

<400> SEQUENCE: 1

Asp Ala Glu Phe Arg His Asp Ser Gly Tyr Glu Val His His Gln Lys
   1               5                   10                  15

Leu Val Phe Phe Ala Glu Asp Val Gly Ser Asn Lys Gly Ala Ile Ile
               20                  25                  30

Gly Leu Met Val Gly Gly Val Val
               35                  40

<210> SEQ ID NO 2
   <211> LENGTH: 42
   <212> TYPE: PRT
   <213> ORGANISM: Artificial Sequence
   <220> FEATURE:
   <221> NAME/KEY: domain
   <223> OTHER INFORMATION: Abeta 1-42 amino acid sequence

<400> SEQUENCE: 2

Asp Ala Glu Phe Arg His Asp Ser Gly Tyr Glu Val His His Gln Lys
   1               5                   10                  15

Leu Val Phe Phe Ala Glu Asp Val Gly Ser Asn Lys Gly Ala Ile Ile
               20                  25                  30

Gly Leu Met Val Gly Gly Val Val Ile Ala
               35                  40

<210> SEQ ID NO 3
   <211> LENGTH: 120
   <212> TYPE: PRT
   <213> ORGANISM: Artificial Sequence
   <220> FEATURE:
   <221> NAME/KEY: domain
   <223> OTHER INFORMATION: mAb-2401 VH amino acid sequence
```

-continued

```
<400> SEQUENCE: 3

Glu Val Gln Leu Gln Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Tyr Met His Trp Val Lys Gln Arg Pro Glu Gln Gly Leu Glu Trp Ile
        35                  40                  45

Gly Arg Ile Asp Pro Thr Asn Gly Asn Thr Lys Tyr Ala Pro Lys Phe
    50                  55                  60

Lys Asp Lys Ala Thr Ile Ile Ala Asp Thr Ser Ser Asn Thr Gly Tyr
65                  70                  75                  80

Leu Gln Leu Ser Ser Leu Thr Ser Glu Asp Thr Ala Ile Tyr Tyr Cys
                85                  90                  95

Ala Arg Arg Val Tyr Tyr Tyr Asp Ser Thr Tyr Asn Tyr Trp Gly Gln
            100                 105                 110

Gly Thr Thr Leu Thr Val Ser Ser
        115                 120

<210> SEQ ID NO 4
<211> LENGTH: 113
<212> TYPE: PRT
<213> ORGANISM: Artificial Sequence
<220> FEATURE:
<221> NAME/KEY: domain
<223> OTHER INFORMATION: mAb-2401 VL amino acid sequence

<400> SEQUENCE: 4

Asp Ile Val Met Thr Gln Ser Pro Ser Ser Leu Thr Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Arg Thr Asp Phe Thr Leu Thr
65                  70                  75                  80

Ile Ser Asn Val Gln Ala Glu Asp Leu Ala Val Tyr Tyr Cys Gln Asn
                85                  90                  95

Asp Tyr Asn Tyr Pro Leu Thr Phe Gly Ala Gly Thr Lys Leu Glu Leu
            100                 105                 110

Lys

<210> SEQ ID NO 5
<211> LENGTH: 121
<212> TYPE: PRT
<213> ORGANISM: Artificial Sequence
<220> FEATURE:
<221> NAME/KEY: domain
<223> OTHER INFORMATION: mAb-3601 VH amino acid sequence

<400> SEQUENCE: 5

Gln Ala Thr Leu Lys Glu Ser Gly Pro Gly Ile Leu Gln Ser Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45
```

```
Trp Leu Ala His Ile Trp Trp Asp Asp Asp Lys Tyr Tyr Asn Pro Ala
        50                  55                  60

Leu Lys Ser Arg Leu Thr Ile Ser Lys Asp Thr Ser Lys Asn Gln Val
 65                  70                  75                  80

Phe Leu Lys Ile Ala Asn Val Asp Thr Ala Asp Thr Ala Thr Tyr Tyr
                     85                  90                  95

Cys Ala Arg Arg Pro Leu Gly Ser Tyr Asp Tyr Phe Asp Tyr Trp Gly
                100                 105                 110

Gln Gly Thr Thr Leu Thr Val Ser Ser
            115                 120

<210> SEQ ID NO 6
<211> LENGTH: 112
<212> TYPE: PRT
<213> ORGANISM: Artificial Sequence
<220> FEATURE:
<221> NAME/KEY: domain
<223> OTHER INFORMATION: mAb-3601 VL amino acid sequence

<400> SEQUENCE: 6

Asp Val Leu Met Thr Gln Thr Pro Leu Ser Leu Pro Val Ser Leu Gly
 1               5                  10                  15

Asp Gln Ala Ser Ile Ser Cys Arg Ser Gln Ser Ile Val His Ser
                20                  25                  30

Asn Gly Asn Thr Tyr Leu Glu Trp Tyr Leu Gln Lys Pro Gly Gln Ser
                 35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
                 85                  90                  95

Ser Arg Val Pro Leu Thr Phe Gly Ala Gly Thr Lys Leu Glu Leu Lys
                100                 105                 110

<210> SEQ ID NO 7
<211> LENGTH: 122
<212> TYPE: PRT
<213> ORGANISM: Artificial Sequence
<220> FEATURE:
<221> NAME/KEY: domain
<223> OTHER INFORMATION: mAb-5101 VH amino acid sequence

<400> SEQUENCE: 7

Gln Val Thr Leu Lys Glu Ser Gly Pro Gly Ile Leu Gln Ser Ser Gln
 1               5                  10                  15

Thr Leu Ser Leu Thr Cys Ser Phe Ser Gly Phe Ser Leu Thr Thr Ser
                20                  25                  30

Gly Met Gly Val Ser Trp Ile Arg Gln Pro Ser Gly Lys Gly Leu Glu
                 35                  40                  45

Trp Leu Ala His Ile Tyr Trp Asp Val Ser Leu Tyr Asn Pro Ser
 50                  55                  60

Leu Lys Ser Arg Leu Thr Ile Ser Lys Asp Ala Ser Arg Asn Gln Val
 65                  70                  75                  80

Phe Leu Lys Ile Thr Ser Val Asp Thr Ala Asp Ser Ala Thr Tyr Tyr
                 85                  90                  95

Cys Val Arg Arg Ile Ile Thr Val Val Asp Ala Met Asp Tyr Trp
                100                 105                 110
```

Gly Gln Gly Thr Ser Val Thr Val Ser Ser
        115                 120

<210> SEQ ID NO 8
<211> LENGTH: 112
<212> TYPE: PRT
<213> ORGANISM: Artificial Sequence
<220> FEATURE:
<221> NAME/KEY: domain
<223> OTHER INFORMATION: mAb-5101 VL amino acid sequence

<400> SEQUENCE: 8

Asp Val Leu Met Thr Gln Thr Pro Leu Ser Leu Pro Val Ser Leu Gly
1               5                   10                  15

Asp Gln Ala Ser Ile Ser Cys Arg Ser Gln Ser Ile Val His Ser
            20                  25                  30

Asn Gly Asn Thr Tyr Leu Glu Trp Tyr Leu Gln Lys Ser Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Ile Tyr Tyr Cys Cys Gln Gly
                85                  90                  95

Ser Arg Val Pro Pro Thr Phe Gly Gly Gly Thr Lys Leu Glu Ile Lys
            100                 105                 110

<210> SEQ ID NO 9
<211> LENGTH: 124
<212> TYPE: PRT
<213> ORGANISM: Artificial Sequence
<220> FEATURE:
<221> NAME/KEY: domain
<223> OTHER INFORMATION: mAb-9001 VH amino acid sequence

<400> SEQUENCE: 9

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Phe
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Phe Leu Lys Ile Ala Ile Val Asp Thr Ala Asp Ile Ala Thr Tyr Tyr
                85                  90                  95

Cys Val Arg Arg Gly Phe His Leu Gly Ser Arg Gly Asp Tyr Phe Asp
            100                 105                 110

His Trp Gly Gln Gly Thr Thr Leu Thr Val Ser Ser
        115                 120

<210> SEQ ID NO 10
<211> LENGTH: 112
<212> TYPE: PRT
<213> ORGANISM: Artificial Sequence
<220> FEATURE:
<221> NAME/KEY: domain
<223> OTHER INFORMATION: mAb-9001 VL amino acid sequence

```
<400> SEQUENCE: 10

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Leu Gly Val Tyr Tyr Cys Phe Gln Gly
                85                  90                  95

Ser Arg Val Pro Leu Thr Phe Gly Ala Gly Thr Lys Leu Glu Leu Lys
            100                 105                 110

<210> SEQ ID NO 11
<211> LENGTH: 5
<212> TYPE: PRT
<213> ORGANISM: Artificial Sequence
<220> FEATURE:
<221> NAME/KEY: domain
<223> OTHER INFORMATION: mAb-2401, HAB-2401 HCDR1 amino acid sequence

<400> SEQUENCE: 11

Asn Thr Tyr Met His
1               5

<210> SEQ ID NO 12
<211> LENGTH: 17
<212> TYPE: PRT
<213> ORGANISM: Artificial Sequence
<220> FEATURE:
<221> NAME/KEY: domain
<223> OTHER INFORMATION: mAb-2401, HAB-2401 HCDR2 amino acid sequence

<400> SEQUENCE: 12

Arg Ile Asp Pro Thr Asn Gly Asn Thr Lys Tyr Ala Pro Lys Phe Lys
1               5                   10                  15

Asp

<210> SEQ ID NO 13
<211> LENGTH: 11
<212> TYPE: PRT
<213> ORGANISM: Artificial Sequence
<220> FEATURE:
<221> NAME/KEY: domain
<223> OTHER INFORMATION: mAb-2401, HAB-2401 HCDR3

<400> SEQUENCE: 13

Arg Val Tyr Tyr Tyr Asp Ser Thr Tyr Asn Tyr
1               5                   10

<210> SEQ ID NO 14
<211> LENGTH: 17
<212> TYPE: PRT
<213> ORGANISM: Artificial Sequence
<220> FEATURE:
<221> NAME/KEY: domain
<223> OTHER INFORMATION: mAb-2401, HAB-2401 LCDR1 amino acid sequence

<400> SEQUENCE: 14
```

```
Lys Ser Ser Gln Ser Leu Leu Asn Ser Gly Asn Gln Lys Asn Tyr Leu
1               5                   10                  15
Thr

<210> SEQ ID NO 15
<211> LENGTH: 7
<212> TYPE: PRT
<213> ORGANISM: Artificial Sequence
<220> FEATURE:
<221> NAME/KEY: domain
<223> OTHER INFORMATION: mAb-2401, HAB-2401 LCDR2 amino acid sequence

<400> SEQUENCE: 15

Trp Ala Ser Thr Arg Glu Ser
1               5

<210> SEQ ID NO 16
<211> LENGTH: 9
<212> TYPE: PRT
<213> ORGANISM: Artificial Sequence
<220> FEATURE:
<221> NAME/KEY: domain
<223> OTHER INFORMATION: mAb-2401, HAB-2401 LCDR3 amino acid sequence

<400> SEQUENCE: 16

Gln Asn Asp Tyr Asn Tyr Pro Leu Thr
1               5

<210> SEQ ID NO 17
<211> LENGTH: 7
<212> TYPE: PRT
<213> ORGANISM: Artificial Sequence
<220> FEATURE:
<221> NAME/KEY: domain
<223> OTHER INFORMATION: mAb-3601, mAb-9001, HAB-3601, HAB-9001 HCDR1
      amino acid sequence

<400> SEQUENCE: 17

Thr Phe Gly Met Gly Val Gly
1               5

<210> SEQ ID NO 18
<211> LENGTH: 16
<212> TYPE: PRT
<213> ORGANISM: Artificial Sequence
<220> FEATURE:
<221> NAME/KEY: domain
<223> OTHER INFORMATION: mAb-3601, mAb-9001 HCDR2 amino acid sequence

<400> SEQUENCE: 18

His Ile Trp Trp Asp Asp Asp Lys Tyr Tyr Asn Pro Ala Leu Lys Ser
1               5                   10                  15

<210> SEQ ID NO 19
<211> LENGTH: 11
<212> TYPE: PRT
<213> ORGANISM: Artificial Sequence
<220> FEATURE:
<221> NAME/KEY: domain
<223> OTHER INFORMATION: mAb-3601, HAB-3601 HCDR3 amino acid sequence

<400> SEQUENCE: 19

Arg Pro Leu Gly Ser Tyr Asp Tyr Phe Asp Tyr
1               5                   10

<210> SEQ ID NO 20
<211> LENGTH: 16
```

```
<212> TYPE: PRT
<213> ORGANISM: Artificial Sequence
<220> FEATURE:
<221> NAME/KEY: domain
<223> OTHER INFORMATION: mAb-3601, mAb-5101, mAb-9001, HAB-3601,
      HAB-5101, HAB-9001 LCDR1 amino acid sequence

<400> SEQUENCE: 20

Arg Ser Ser Gln Ser Ile Val His Ser Asn Gly Asn Thr Tyr Leu Glu
1               5                   10                  15

<210> SEQ ID NO 21
<211> LENGTH: 7
<212> TYPE: PRT
<213> ORGANISM: Artificial Sequence
<220> FEATURE:
<221> NAME/KEY: domain
<223> OTHER INFORMATION: mAb-3601, mAb-5101, mAb-9001, HAB-3601,
      HAB-5101, HAB-9001 LCDR2 amino acid sequence

<400> SEQUENCE: 21

Lys Val Ser Asn Arg Phe Ser
1               5

<210> SEQ ID NO 22
<211> LENGTH: 9
<212> TYPE: PRT
<213> ORGANISM: Artificial Sequence
<220> FEATURE:
<221> NAME/KEY: domain
<223> OTHER INFORMATION: mAb-3601, mAb-9001, HAB-3601, HAB-9001 LCDR3
      amino acid sequence

<400> SEQUENCE: 22

Phe Gln Gly Ser Arg Val Pro Leu Thr
1               5

<210> SEQ ID NO 23
<211> LENGTH: 7
<212> TYPE: PRT
<213> ORGANISM: Artificial Sequence
<220> FEATURE:
<221> NAME/KEY: domain
<223> OTHER INFORMATION: mAb-5101, HAB-5101 HCDR1 amino acid sequence

<400> SEQUENCE: 23

Thr Ser Gly Met Gly Val Ser
1               5

<210> SEQ ID NO 24
<211> LENGTH: 16
<212> TYPE: PRT
<213> ORGANISM: Artificial Sequence
<220> FEATURE:
<221> NAME/KEY: domain
<223> OTHER INFORMATION: mAb-5101, HAB-5101 HCDR2 amino acid sequence

<400> SEQUENCE: 24

His Ile Tyr Trp Asp Asp Val Ser Leu Tyr Asn Pro Ser Leu Lys Ser
1               5                   10                  15

<210> SEQ ID NO 25
<211> LENGTH: 12
<212> TYPE: PRT
<213> ORGANISM: Artificial Sequence
<220> FEATURE:
<221> NAME/KEY: domain
<223> OTHER INFORMATION: mAb-5101, HAB-5101 HCDR3 amino acid sequence
```

```
<400> SEQUENCE: 25

Arg Arg Ile Ile Thr Val Val Asp Ala Met Asp Tyr
1               5                   10

<210> SEQ ID NO 26
<211> LENGTH: 9
<212> TYPE: PRT
<213> ORGANISM: Artificial Sequence
<220> FEATURE:
<221> NAME/KEY: domain
<223> OTHER INFORMATION: mAb-5101 LCDR3 amino acid sequence

<400> SEQUENCE: 26

Cys Gln Gly Ser Arg Val Pro Pro Thr
1               5

<210> SEQ ID NO 27
<211> LENGTH: 14
<212> TYPE: PRT
<213> ORGANISM: Artificial Sequence
<220> FEATURE:
<221> NAME/KEY: domain
<223> OTHER INFORMATION: mAb-9001, HAB-9001 HCDR3 amino acid sequence

<400> SEQUENCE: 27

Arg Gly Phe His Leu Gly Ser Arg Gly Asp Tyr Phe Asp His
1               5                   10

<210> SEQ ID NO 28
<211> LENGTH: 98
<212> TYPE: PRT
<213> ORGANISM: Artificial Sequence
<220> FEATURE:
<221> NAME/KEY: domain
<223> OTHER INFORMATION: human germline (IGHV1-24*01) heavy chain
      template amino acid sequence

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr

<210> SEQ ID NO 29
<211> LENGTH: 95
<212> TYPE: PRT
<213> ORGANISM: Artificial Sequence
<220> FEATURE:
<221> NAME/KEY: domain
<223> OTHER INFORMATION: human germline (IGKV1-27*01) light chain
      template amino acid sequence

<400> SEQUENCE: 29

Asp Ile Gln Met Thr Gln Ser Pro Ser Ser Leu Ser Ala Ser Val Gly
1               5                   10                  15
```

```
Asp Arg Val Thr Ile Thr Cys Arg Ala Ser Gln Gly Ile Ser Asn Tyr
        20                  25                  30

Leu Ala Trp Tyr Gln Gln Lys Pro Gly Lys Val Pro Lys Leu Leu Ile
            35                  40                  45

Tyr Ala Ala Ser Thr Leu Gln Ser Gly Val Pro Ser Arg Phe Ser Gly
50                      55                  60

Ser Gly Ser Gly Thr Asp Phe Thr Leu Thr Ile Ser Ser Leu Gln Pro
65                      70                  75                  80

Glu Asp Val Ala Thr Tyr Tyr Cys Gln Lys Tyr Asn Ser Ala Pro
                85                  90                  95

<210> SEQ ID NO 30
<211> LENGTH: 450
<212> TYPE: PRT
<213> ORGANISM: Artificial Sequence
<220> FEATURE:
<221> NAME/KEY: domain
<223> OTHER INFORMATION: HAB-2401 heavy chain amino acid sequence

<400> SEQUENCE: 30

Glu Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asn Thr
            20                  25                  30

Tyr Met His Trp Val Arg Gln Ala Pro Gly Lys Gly Leu Glu Trp Met
        35                  40                  45

Gly Arg Ile Asp Pro Thr Asn Gly Asn Thr Lys Tyr Ala Pro Lys Phe
    50                  55                  60

Lys Asp Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Val Tyr Tyr Tyr Asp Ser Thr Tyr Asn Tyr Trp Gly Lys
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
        130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
            275                 280                 285
Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
                340                 345                 350

Thr Leu Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
                435                 440                 445

Gly Lys
    450

<210> SEQ ID NO 31
<211> LENGTH: 220
<212> TYPE: PRT
<213> ORGANISM: Artificial Sequence
<220> FEATURE:
<221> NAME/KEY: domain
<223> OTHER INFORMATION: HAB-2401 light chain amino acid sequence

<400> SEQUENCE: 31

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
                20                  25                  30

Gly Asn Gln Lys Asn Tyr Leu Thr Trp Tyr Gln Gln Lys Pro Gly Lys
            35                  40                  45

Val Pro Lys Leu Leu Ile Tyr Trp Ala Ser Thr Arg Glu Ser Gly Val
        50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp Tyr Asn Tyr Pro Leu Thr Phe Gly Gly Gly Thr Lys Val Glu Ile
                100                 105                 110

Lys Arg Thr Val Ala Ala Pro Ser Val Phe Ile Phe Pro Pro Ser Asp
                115                 120                 125

Glu Gln Leu Lys Ser Gly Thr Ala Ser Val Val Cys Leu Leu Asn Asn
130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175
```

```
Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
        210                 215                 220

<210> SEQ ID NO 32
<211> LENGTH: 98
<212> TYPE: PRT
<213> ORGANISM: Artificial Sequence
<220> FEATURE:
<221> NAME/KEY: domain
<223> OTHER INFORMATION: human germline (IGHV3-30*01) heavy chain
      template amino acid sequence

<400> SEQUENCE: 32

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 33
<211> LENGTH: 95
<212> TYPE: PRT
<213> ORGANISM: Artificial Sequence
<220> FEATURE:
<221> NAME/KEY: domain
<223> OTHER INFORMATION: human germline(IGKV1-39*01)light chain template
      amino acid sequence

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 34
<211> LENGTH: 451
<212> TYPE: PRT
<213> ORGANISM: Artificial Sequence
<220> FEATURE:
<221> NAME/KEY: domain
<223> OTHER INFORMATION: HAB-3601 heavy chain amino acid sequence
```

<400> SEQUENCE: 34

Gln Val Gln Leu Val Glu Ser Gly Gly Val Val Gln Pro Gly Arg
1               5                   10                  15

Ser Leu Arg Leu Ser Cys Ala Ala Ser Gly Phe Ala Phe Ser Thr Phe
            20                  25                  30

Gly Met Gly Val Gly Trp Val Arg Gln Ala Pro Gly Lys Gly Leu Glu
        35                  40                  45

Trp Val Ala His Ile Trp Trp Asp Asp Asn Lys Tyr Tyr Asn Pro Ala
    50                  55                  60

Leu Lys Ser Arg Phe Thr Ile Ser Arg Asp Asn Ser Lys Asn Thr Leu
65                  70                  75                  80

Tyr Leu Gln Met Asn Thr Leu Arg Ala Glu Asp Thr Ala Val Tyr Tyr
                85                  90                  95

Cys Ala Arg Arg Pro Leu Gly Ser Tyr Asp Tyr Phe Asp Tyr Trp Gly
            100                 105                 110

Lys Gly Thr Thr Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val

```
                        405                 410                 415
Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
            435                 440                 445

Pro Gly Lys
    450

<210> SEQ ID NO 35
<211> LENGTH: 219
<212> TYPE: PRT
<213> ORGANISM: Artificial Sequence
<220> FEATURE:
<221> NAME/KEY: domain
<223> OTHER INFORMATION: HAB-3601 light chain amino acid sequence

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Arg Val Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 36
<211> LENGTH: 100
<212> TYPE: PRT
<213> ORGANISM: Artificial Sequence
<220> FEATURE:
<221> NAME/KEY: domain
<223> OTHER INFORMATION: human germline (IGHV2-70D*04) heavy chain
      template amino acid sequence

<400> SEQUENCE: 36

Gln Val Thr Leu Lys Glu Ser Gly Pro Ala Leu Val Lys Pro Thr Gln
1               5                   10                  15
```

Thr Leu Thr Leu Thr Cys Thr Phe Ser Gly Phe Ser Leu Ser Thr Ser
                    20                  25                  30

Gly Met Arg Val Ser Trp Ile Arg Gln Pro Pro Gly Lys Ala Leu Glu
                35                  40                  45

Trp Leu Ala Arg Ile Asp Trp Asp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                    85                  90                  95

Cys Ala Arg Ile
            100

<210> SEQ ID NO 37
<211> LENGTH: 101
<212> TYPE: PRT
<213> ORGANISM: Artificial Sequence
<220> FEATURE:
<221> NAME/KEY: domain
<223> OTHER INFORMATION: human germline(IGKV2-40*01)light chain template
      amino acid sequence

<400> SEQUENCE: 37

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Leu Leu Asp Ser
                20                  25                  30

Asp Asp Gly Asn Thr Tyr Leu Asp Trp Tyr Leu Gln Lys Pro Gly Gln
            35                  40                  45

Ser Pro Gln Leu Leu Ile Tyr Thr Leu Ser Tyr Arg Ala Ser Gly Val
    50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Val Gly Val Tyr Tyr Cys Met Gln
                85                  90                  95

Arg Ile Glu Phe Pro
            100

<210> SEQ ID NO 38
<211> LENGTH: 452
<212> TYPE: PRT
<213> ORGANISM: Artificial Sequence
<220> FEATURE:
<221> NAME/KEY: domain
<223> OTHER INFORMATION: HAB-5101 heavy chain amino acid sequence

<400> SEQUENCE: 38

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                    20                  25                  30

Gly Met Gly Val Ser Trp Ile Arg Gln Pro Pro Gly Lys Ala Leu Glu
                35                  40                  45

Trp Leu Ala His Ile Tyr Trp Asp Asp Val Ser Leu Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                    85                  90                  95

```
Cys Ala Arg Arg Arg Ile Ile Thr Val Val Asp Ala Met Asp Tyr Trp
            100                 105                 110

Gly Gln Gly Thr Thr Val Thr Val Ser Ser Ala Ser Thr Lys Gly Pro
            115                 120                 125

Ser Val Phe Pro Leu Ala Pro Ser Ser Lys Ser Thr Ser Gly Gly Thr
            130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                    165                 170                 175

Ala Val Leu Gln Ser Ser Gly Leu Tyr Ser Leu Ser Ser Val Val Thr
                180                 185                 190

Val Pro Ser Ser Ser Leu Gly Thr Gln Thr Tyr Ile Cys Asn Val Asn
                195                 200                 205

His Lys Pro Ser Asn Thr Lys Val Asp Lys Lys Val Glu Pro Lys Ser
            210                 215                 220

Cys Asp Lys Thr His Thr Cys Pro Pro Cys Pro Ala Pro Glu Leu Leu
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
        290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Pro Ala Pro
                325                 330                 335

Ile Glu Lys Thr Ile Ser Lys Ala Lys Gly Gln Pro Arg Glu Pro Gln
                340                 345                 350

Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
            435                 440                 445

Ser Pro Gly Lys
        450

<210> SEQ ID NO 39
<211> LENGTH: 219
<212> TYPE: PRT
<213> ORGANISM: Artificial Sequence
<220> FEATURE:
<221> NAME/KEY: domain
<223> OTHER INFORMATION: HAB-5101 light chain amino acid sequence
```

```
<400> SEQUENCE: 39

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Ser Arg Val Pro Pro Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 40
<211> LENGTH: 454
<212> TYPE: PRT
<213> ORGANISM: Artificial Sequence
<220> FEATURE:
<221> NAME/KEY: domain
<223> OTHER INFORMATION: HAB-9001 heavy chain amino acid sequence

<400> SEQUENCE: 40

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
            20                  25                  30

Gly Met Gly Val Gly Trp Ile Arg Gln Pro Pro Gly Lys Ala Leu Glu
        35                  40                  45

Trp Leu Ala His Ile Trp Trp Asp Asp Asn Lys Tyr Tyr Asn Pro Ala
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly Phe His Leu Gly Ser Arg Gly Asp Tyr Phe Asp
            100                 105                 110

His Trp Gly Gln Gly Thr Thr Val Thr Val Ser Ser Ala Ser Thr Lys
        115                 120                 125
```

Gly Pro Ser Val Phe Pro Leu Ala Pro Ser Ser Lys Ser Thr Ser Gly
    130                 135                 140

Gly Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
            180                 185                 190

Val Thr Val Pro Ser Ser Ser Leu Gly Thr Gln Thr Tyr Ile Cys Asn
        195                 200                 205

Val Asn His Lys Pro Ser Asn Thr Lys Val Asp Lys Lys Val Glu Pro
    210                 215                 220

Lys Ser Cys Asp Lys Thr His Thr Cys Pro Pro Cys Pro Ala Pro Glu
225                 230                 235                 240

Leu Leu Gly Gly Pro Ser Val Phe Leu Phe Pro Pro Lys Pro Lys Asp
                245                 250                 255

Thr Leu Met Ile Ser Arg Thr Pro Glu Val Thr Cys Val Val Val Asp
            260                 265                 270

Val Ser His Glu Asp Pro Glu Val Lys Phe Asn Trp Tyr Val Asp Gly
        275                 280                 285

Val Glu Val His Asn Ala Lys Thr Lys Pro Arg Glu Glu Gln Tyr Asn
    290                 295                 300

Ser Thr Tyr Arg Val Val Ser Val Leu Thr Val Leu His Gln Asp Trp
305                 310                 315                 320

Leu Asn Gly Lys Glu Tyr Lys Cys Lys Val Ser Asn Lys Ala Leu Pro
                325                 330                 335

Ala Pro Ile Glu Lys Thr Ile Ser Lys Ala Lys Gly Gln Pro Arg Glu
            340                 345                 350

Pro Gln Val Tyr Thr Leu Pro Pro Ser Arg Asp Glu Leu Thr Lys Asn
        355                 360                 365

Gln Val Ser Leu Thr Cys Leu Val Lys Gly Phe Tyr Pro Ser Asp Ile
    370                 375                 380

Ala Val Glu Trp Glu Ser Asn Gly Gln Pro Glu Asn Asn Tyr Lys Thr
385                 390                 395                 400

Thr Pro Pro Val Leu Asp Ser Asp Gly Ser Phe Phe Leu Tyr Ser Lys
                405                 410                 415

Leu Thr Val Asp Lys Ser Arg Trp Gln Gln Gly Asn Val Phe Ser Cys
            420                 425                 430

Ser Val Met His Glu Ala Leu His Asn His Tyr Thr Gln Lys Ser Leu
        435                 440                 445

Ser Leu Ser Pro Gly Lys
    450

<210> SEQ ID NO 41
<211> LENGTH: 219
<212> TYPE: PRT
<213> ORGANISM: Artificial Sequence
<220> FEATURE:
<221> NAME/KEY: domain
<223> OTHER INFORMATION: HAB-9001 light chain amino acid sequence

<400> SEQUENCE: 41

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

```
Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Gly
                 85                  90                  95

Ser Arg Val Pro Leu Thr Phe Gly Gln Gly Thr Lys Leu Glu Ile Lys
                100                 105                 110

Arg Thr Val Ala Ala Pro Ser Val Phe Ile Phe Pro Pro Ser Asp Glu
                115                 120                 125

Gln Leu Lys Ser Gly Thr Ala Ser Val Val Cys Leu Leu Asn Asn Phe
130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
                180                 185                 190

Lys His Lys Val Tyr Ala Cys Glu Val Thr His Gln Gly Leu Ser Ser
                195                 200                 205

Pro Val Thr Lys Ser Phe Asn Arg Gly Glu Cys
                210                 215

<210> SEQ ID NO 42
<211> LENGTH: 330
<212> TYPE: PRT
<213> ORGANISM: Artificial Sequence
<220> FEATURE:
<221> NAME/KEY: domain
<223> OTHER INFORMATION: HAB-2401, HAB-3601, HAB-5101, HAB-9001 heavy
      chain constant region amino acid sequence

<400> SEQUENCE: 42

Ala Ser Thr Lys Gly Pro Ser Val Phe Pro Leu Ala Pro Ser Ser Lys
 1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
         35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
                100                 105                 110

Pro Ala Pro Glu Leu Leu Gly Gly Pro Ser Val Phe Leu Phe Pro Pro
                115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160
```

-continued

```
Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
        180                 185                 190

His Gln Asp Trp Leu Asn Gly Lys Glu Tyr Lys Cys Lys Val Ser Asn
    195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
        260                 265                 270

Asn Tyr Lys Thr Thr Pro Pro Val Leu Asp Ser Asp Gly Ser Phe Phe
    275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 43
<211> LENGTH: 107
<212> TYPE: PRT
<213> ORGANISM: Artificial Sequence
<220> FEATURE:
<221> NAME/KEY: domain
<223> OTHER INFORMATION: HAB-2401, HAB-3601, HAB-5101, HAB-9001 light
      chain constant region amino acid sequence

<400> SEQUENCE: 43

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
            85                  90                  95

Pro Val Thr Lys Ser Phe Asn Arg Gly Glu Cys
        100                 105

<210> SEQ ID NO 44
<211> LENGTH: 120
<212> TYPE: PRT
<213> ORGANISM: Artificial Sequence
<220> FEATURE:
<221> NAME/KEY: domain
<223> OTHER INFORMATION: HAB-2401 heavy chain variable region amino acid
      sequence

<400> SEQUENCE: 44

Glu Val Gln Leu Val Gln Ser Gly Ala Glu Val Lys Lys Pro Gly Ala
```

```
                1               5                   10                  15
Ser Val Lys Val Ser Cys Lys Val Ser Gly Tyr Thr Leu Thr Asn Thr
                    20                  25                  30

Tyr Met His Trp Val Arg Gln Ala Pro Gly Lys Gly Leu Glu Trp Met
            35                  40                  45

Gly Arg Ile Asp Pro Thr Asn Gly Asn Thr Lys Tyr Ala Pro Lys Phe
        50                  55                  60

Lys Asp Arg Val Thr Met Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Val Tyr Tyr Tyr Asp Ser Thr Tyr Asn Tyr Trp Gly Lys
            100                 105                 110

Gly Thr Thr Val Thr Val Ser Ser
            115                 120

<210> SEQ ID NO 45
<211> LENGTH: 113
<212> TYPE: PRT
<213> ORGANISM: Artificial Sequence
<220> FEATURE:
<221> NAME/KEY: domain
<223> OTHER INFORMATION: HAB-2401 light chain variable region amino acid
      sequence

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Lys
        35                  40                  45

Val Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp Tyr Asn Tyr Pro Leu Thr Phe Gly Gly Gly Thr Lys Val Glu Ile
            100                 105                 110

Lys

<210> SEQ ID NO 46
<211> LENGTH: 121
<212> TYPE: PRT
<213> ORGANISM: Artificial Sequence
<220> FEATURE:
<221> NAME/KEY: domain
<223> OTHER INFORMATION: HAB-3601 heavy chain variable region amino acid
      sequence

<400> SEQUENCE: 46

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ala Phe Ser Thr Phe
            20                  25                  30

Gly Met Gly Val Gly Trp Val Arg Gln Ala Pro Gly Lys Gly Leu Glu
        35                  40                  45
```

Trp Val Ala His Ile Trp Trp Asp Asp Asn Lys Tyr Tyr Asn Pro Ala
    50                  55                  60

Leu Lys Ser Arg Phe Thr Ile Ser Arg Asp Asn Ser Lys Asn Thr Leu
65                  70                  75                  80

Tyr Leu Gln Met Asn Thr Leu Arg Ala Glu Asp Thr Ala Val Tyr Tyr
                85                  90                  95

Cys Ala Arg Arg Pro Leu Gly Ser Tyr Asp Tyr Phe Asp Tyr Trp Gly
            100                 105                 110

Lys Gly Thr Thr Val Thr Val Ser Ser
            115                 120

<210> SEQ ID NO 47
<211> LENGTH: 112
<212> TYPE: PRT
<213> ORGANISM: Artificial Sequence
<220> FEATURE:
<221> NAME/KEY: domain
<223> OTHER INFORMATION: HAB-3601 light chain variable region amino acid
      sequence

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
                20                  25                  30

Asn Gly Asn Thr Tyr Leu Glu Trp Tyr Gln Gln Lys Pro Gly Lys Ala
            35                  40                  45

Pro Lys Leu Leu Ile Tyr Lys Val Ser Asn Arg Phe Ser Gly Val Pro
50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Arg Val Pro Leu Thr Phe Gly Gly Gly Thr Lys Val Glu Ile Lys
            100                 105                 110

<210> SEQ ID NO 48
<211> LENGTH: 122
<212> TYPE: PRT
<213> ORGANISM: Artificial Sequence
<220> FEATURE:
<221> NAME/KEY: domain
<223> OTHER INFORMATION: HAB-5101 heavy chain variable region amino acid
      sequence

<400> SEQUENCE: 48

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Ala Leu Glu
            35                  40                  45

Trp Leu Ala His Ile Tyr Trp Asp Asp Val Ser Leu Tyr Asn Pro Ser
50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Arg Ile Ile Thr Val Val Asp Ala Met Asp Tyr Trp

```
              100             105                 110
Gly Gln Gly Thr Thr Val Thr Val Ser Ser
            115                 120

<210> SEQ ID NO 49
<211> LENGTH: 112
<212> TYPE: PRT
<213> ORGANISM: Artificial Sequence
<220> FEATURE:
<221> NAME/KEY: domain
<223> OTHER INFORMATION: HAB-5101 light chain variable region amino acid
      sequence

<400> SEQUENCE: 49

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Gly
                85                  90                  95

Ser Arg Val Pro Pro Thr Phe Gly Gly Gly Thr Lys Val Glu Ile Lys
            100                 105                 110

<210> SEQ ID NO 50
<211> LENGTH: 124
<212> TYPE: PRT
<213> ORGANISM: Artificial Sequence
<220> FEATURE:
<221> NAME/KEY: domain
<223> OTHER INFORMATION: HAB-9001 heavy chain variable region amino acid
      sequence

<400> SEQUENCE: 50

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Phe
                20                  25                  30

Gly Met Gly Val Gly Trp Ile Arg Gln Pro Pro Gly Lys Ala Leu Glu
            35                  40                  45

Trp Leu Ala His Ile Trp Trp Asp Asp Asn Lys Tyr Tyr Asn Pro Ala
        50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly Phe His Leu Gly Ser Arg Gly Asp Tyr Phe Asp
            100                 105                 110

His Trp Gly Gln Gly Thr Thr Val Thr Val Ser Ser
        115                 120

<210> SEQ ID NO 51
<211> LENGTH: 112
<212> TYPE: PRT
<213> ORGANISM: Artificial Sequence
```

```
<220> FEATURE:
<221> NAME/KEY: domain
<223> OTHER INFORMATION: HAB-9001 light chain variable region amino acid
      sequence

<400> SEQUENCE: 51

Asp Val Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Arg Val Pro Leu Thr Phe Gly Gln Gly Thr Lys Leu Glu Ile Lys
            100                 105                 110

<210> SEQ ID NO 52
<211> LENGTH: 16
<212> TYPE: PRT
<213> ORGANISM: Artificial Sequence
<220> FEATURE:
<221> NAME/KEY: domain
<223> OTHER INFORMATION: HAB-3601, HAB-9001 HCDR2 amino acid sequence

<400> SEQUENCE: 52

His Ile Trp Trp Asp Asp Asn Lys Tyr Tyr Asn Pro Ala Leu Lys Ser
1               5                   10                  15

<210> SEQ ID NO 53
<211> LENGTH: 9
<212> TYPE: PRT
<213> ORGANISM: Artificial Sequence
<220> FEATURE:
<221> NAME/KEY: domain
<223> OTHER INFORMATION: HAB-5101 LCDR3 amino acid sequence

<400> SEQUENCE: 53

Ser Gln Gly Ser Arg Val Pro Pro Thr
1               5

<210> SEQ ID NO 54
<211> LENGTH: 1350
<212> TYPE: DNA
<213> ORGANISM: Artificial Sequence
<220> FEATURE:
<221> NAME/KEY: Gene
<223> OTHER INFORMATION: HAB-2401 heavy chain nucleotide sequence

<400> SEQUENCE: 54
gaggtgcagc tggtgcagag cggtgccgag gtgaagaagc cgggagcgag cgtgaaagtg      60
agctgcaagg tgagcggcta cacccctgacc aacacctaca tgcactgggt gaggcaggcc    120
cctgggaagg gctggagtg gatgggcagg atcgacccca ccaacggcaa caccaagtac      180
gcccccaagt tcaaggacag ggtgaccatg accgccgaca ccagcaccga cactgcgtac     240
atggagctga gcagcctgag aagcgaggac accgccgtgt actactgcgc caggagggtc    300
tactactacg acagcaccta taactactgg ggtaagggca ccactgtaac cgtgagctct    360
```

```
gcttcgacca agggcccatc ggtcttcccc ctggcaccct cctccaagag cacctctggg      420
ggcacagcgg ccctgggctg cctggtcaag gactacttcc ccgaaccggt gacggtgtcg      480
tggaactcag gcgccctgac cagcggcgtg cacaccttcc cggctgtcct acagtcctca      540
ggactctact ccctcagcag cgtggtgacc gtgccctcca gcagcttggg cacccagacc      600
tacatctgca acgtgaatca caagcccagc aacaccaagg tggacaagaa agttgagccc      660
aaatcttgtg acaaaactca cacatgccca ccgtgcccag cacctgaact cctgggggga      720
ccgtcagtct tcctcttccc cccaaaaccc aaggacaccc tcatgatctc ccggacccct      780
gaggtcacat gcgtggtggt ggacgtgagc cacgaagacc ctgaggtcaa gttcaactgg      840
tacgtggacg gcgtggaggt gcataatgcc aagacaaagc cgcgggagga gcagtacaac      900
agcacgtacc gtgtggtcag cgtcctcacc gtcctgcacc aggactggct gaatggcaag      960
gagtacaagt gcaaggtctc caacaaagcc ctcccagccc ccatcgagaa aaccatctcc     1020
aaagccaaag ggcagccccg agaaccacag gtgtacaccc tgcccccatc ccgggatgag     1080
ctgaccaaga accaggtcag cctgacctgc ctggtcaaag gcttctatcc cagcgacatc     1140
gccgtggagt gggagagcaa tgggcagccg gagaacaact acaagaccac gcctcccgtg     1200
ctggactccg acggctcctt cttcctctac agcaagctca ccgtggacaa gagcaggtgg     1260
cagcagggga acgtcttctc atgctccgtg atgcatgagg ctctgcacaa ccactacacg     1320
cagaagagcc tctccctgtc tccgggtaaa                                     1350

<210> SEQ ID NO 55
<211> LENGTH: 660
<212> TYPE: DNA
<213> ORGANISM: Artificial Sequence
<220> FEATURE:
<221> NAME/KEY: Gene
<223> OTHER INFORMATION: HAB-2401 light chain nucleotide sequence

<400> SEQUENCE: 55
gacatccaga tgacccaaag ccccagctcc ctgagcgcca gcgtggggga cagggtgact       60
atcacctgca agagcagcca gagcctgctg aactcaggca accagaagaa ctacctgacc      120
tggtatcagc agaagcccgg caaggtgccc aagcttctga tctactgggc cagcaccagg      180
gagagcggcg tgcccagcag gttcagtggc agcggtagcg gaaccgactt caccccttaca     240 atctcaagcc tgcagcccga ggacgttgcc acctactact gccagaacga ctacaactac      300
cccctcacct tcggcggagg gactaaggtg gagatcaagc gtacggtggc tgcaccatct      360
gtcttcatct tcccgccatc tgatgagcag ttgaaatctg gaactgcctc tgttgtgtgc      420
ctgctgaata acttctatcc cagagaggcc aaagtacagt ggaaggtgga taacgccctc      480
caatcgggta actcccagga gagtgtcaca gagcaggaca gcaaggacag cacctacagc      540
ctcagcagca ccctgacgct gagcaaagca gactacgaga aacacaaagt ctacgcctgc      600
gaagtcaccc atcagggcct gagctcgccc gtcacaaaga gcttcaacag gggagagtgt     660

<210> SEQ ID NO 56
<211> LENGTH: 1353
<212> TYPE: DNA
<213> ORGANISM: Artificial Sequence
<220> FEATURE:
<221> NAME/KEY: Gene
<223> OTHER INFORMATION: HAB-3601 heavy chain nucleotide sequence

<400> SEQUENCE: 56
caggtgcagc tggtggagag cggcggtggc gtggtgcaac ccggcaggag cctgaggctg       60
```

```
agctgcgctg ccagcggctt cgccttcagc accttcggca tgggcgtggg ctgggtgagg      120
caggcacccg gaaagggcct ggagtgggtg cccatatct ggtgggacga caacaagtac       180
tacaatccag ccctgaagag caggttcacc atcagcaggg acaacagcaa aaacaccctg      240
tacctgcaga tgaataccct gagggccgag gataccgccg tgtactactg cgccaggagg      300
cccctgggct cctacgatta cttcgactac tggggcaagg gaaccaccgt gaccgtgagc      360
agcgcttcga ccaagggccc atcggtcttc cccctggcac cctcctccaa gagcacctct      420
gggggcacag cggccctggg ctgcctggtc aaggactact ccccgaaccc ggtgacggtg      480
tcgtggaact caggcgccct gaccagcggc gtgcacacct tcccggctgt cctacagtcc      540
tcaggactct actccctcag cagcgtggtg accgtgccct ccagcagctt gggcacccag      600
acctacatct gcaacgtgaa tcacaagccc agcaacacca aggtggacaa gaaagttgag      660
cccaaatctt gtgacaaaac tcacacatgc ccaccgtgcc cagcacctga actcctgggg      720
ggaccgtcag tcttcctctt ccccccaaaa cccaaggaca cctcatgat ctccccggacc       780 cctgaggtca catgcgtggt ggtggacgtg agccacgaag accctgaggt caagttcaac      840
tggtacgtgg acggcgtgga ggtgcataat gccaagacaa agccgcggga ggagcagtac      900
aacagcacgt accgtgtggt cagcgtcctc accgtcctgc accaggactg gctgaatggc      960
aaggagtaca gtgcaaggt ctccaacaaa gccctcccag cccccatcga gaaaaccatc      1020
tccaaagcca agggcagcc ccgagaacca caggtgtaca ccctgccccc atcccgggat      1080
gagctgacca gaaccaggt cagcctgacc tgcctggtca aaggcttcta tcccagcgac      1140
atcgccgtgg agtgggagag caatgggcag ccggagaaca actacaagac cacgcctccc      1200
gtgctggact ccgacggctc cttcttcctc tacagcaagc tcaccgtgga caagagcagg      1260
tggcagcagg ggaacgtctt ctcatgctcc gtgatgcatg aggctctgca caaccactac      1320
acgcagaaga gcctctccct gtctccgggt aaa                                  1353
```

<210> SEQ ID NO 57
<211> LENGTH: 657
<212> TYPE: DNA
<213> ORGANISM: Artificial Sequence
<220> FEATURE:
<221> NAME/KEY: Gene
<223> OTHER INFORMATION: HAB-3601 light chain nucleotide sequence

<400> SEQUENCE: 57

```
gacatccaga tgacccagag ccccagcagt ctgagcgcca gcgtgggcga cagggtcacc       60
atcacctgta ggagcagcca gagcatcgtg cacagcaacg gcaacaccta cctggagtgg      120
tatcagcaaa agcccggcaa ggccccaag cttctgatat acaaggtgag caacaggttc       180
tcaggcgttc ccagtaggtt cagcggaagc ggcagcggga ccgacttcac cctgaccatc      240
agctccctgc agcccgagga cttcgccacc tactactgct ccagggcag ccgggtgcct       300 ctgacctttg gtgggggcac caaggtggag attaagcgta cggtggctgc accatctgtc      360
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgt         657
```

<210> SEQ ID NO 58
<211> LENGTH: 1356
<212> TYPE: DNA
<213> ORGANISM: Artificial Sequence
<220> FEATURE:
<221> NAME/KEY: Gene
<223> OTHER INFORMATION: HAB-5101 heavy chain nucleotide sequence

<400> SEQUENCE: 58

```
caggtgaccc tgaaagaaag cggccctgct ctggtgaagc ccacccagac cctcaccctg      60
acctgcacct tcagcggctt cagcttgagc accagcggca tgggcgtgag ctggatcagg     120
cagcctcccg gcaaggccct ggagtggctg gcccacatct actgggacga cgtgagcctg     180
tacaaccta gcctgaagag ccgcctgaca atcagcaagg acaccagcaa gaaccaggtg     240
gtgctgacca tgaccaacat ggaccccgtg gacaccgcca cctactactg cgccaggagg     300
aggatcatca ccgtggtgga cgccatggac tattggggcc agggcaccac tgtgaccgtg     360
agcagcgctt cgaccaaggg cccatcggtc ttccccctgg cacctcctc aagagcacc     420
tctggggca cagcggccct gggctgcctg gtcaaggact acttccccga accggtgacg     480
gtgtcgtgga actcaggcgc cctgaccagc ggcgtgcaca ccttcccggc tgtcctacag     540
tcctcaggac tctactccct cagcagcgtg gtgaccgtgc cctccagcag cttgggcacc     600
cagacctaca tctgcaacgt gaatcacaag cccagcaaca ccaaggtgga caagaaagtt     660
gagcccaaat cttgtgacaa aactcacaca tgcccaccgt gcccagcacc tgaactcctg     720
gggggaccgt cagtcttcct cttcccccca aaacccaagg acaccctcat gatctcccgg     780
acccctgagg tcacatgcgt ggtggtggac gtgagccacg aagaccctga ggtcaagttc     840
aactggtacg tggacggcgt ggaggtgcat aatgccaaga caaagccgcg ggaggagcag     900
tacaacagca cgtaccgtgt ggtcagcgtc ctcaccgtcc tgcaccagga ctggctgaat     960
ggcaaggagt acaagtgcaa ggtctccaac aaagccctcc cagcccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga caactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga gagcctctc cctgtctccg ggtaaa                               1356
```

<210> SEQ ID NO 59
<211> LENGTH: 657
<212> TYPE: DNA
<213> ORGANISM: Artificial Sequence
<220> FEATURE:
<221> NAME/KEY: Gene
<223> OTHER INFORMATION: HAB-5101 light chain nucleotide sequence

<400> SEQUENCE: 59

```
gacgtcgtga tgacccagac cccctgagc ctgccgtga cctggcga gccgccagc       60
atcagctgca ggagcagcca gagcatcgtg cacagcaacg caacacccta cctggagtgg     120
tacctgcaga agcccggtca gagccccaag ctgctgatat acaaggtgag caacaggttc    180
agcggcgtgc ccgacaggtt ttccggcagc ggaagcggca ccgacttcac cctgaagatc    240
agccgcgtgg aggccgagga cgtgggcgtg tactactgca gtcagggaag ccgagtgccc     300
cccacctttg gaggcggaac taaggtggag atcaagcgta cggtggctgc accatctgtc     360
```

```
ttcatcttcc cgccatctga tgagcagttg aaatctggaa ctgcctctgt tgtgtgcctg      420
ctgaataact tctatcccag agaggccaaa gtacagtgga aggtggataa cgccctccaa      480
tcgggtaact cccaggagag tgtcacagag caggacagca aggacagcac ctacagcctc      540
agcagcaccc tgacgctgag caaagcagac tacgagaaac acaaagtcta cgcctgcgaa      600
gtcacccatc agggcctgag ctcgcccgtc acaaagagct tcaacagggg agagtgt        657
```

<210> SEQ ID NO 60
<211> LENGTH: 1362
<212> TYPE: DNA
<213> ORGANISM: Artificial Sequence
<220> FEATURE:
<221> NAME/KEY: Gene
<223> OTHER INFORMATION: HAB-9001 heavy chain nucleotide sequence

<400> SEQUENCE: 60

```
caggtgaccc tcaaggaatc tggccctgca ctggtgaagc ccacccagac cctgacgctg       60
acctgcacct ttagcggctt cagcttgagc accttcggca tgggcgtggg ctggatcagg      120
cagcctcccg gaaaggccct ggagtggctg gcccacatct ggtgggacga caacaagtac      180
tacaaccccg ctctgaagag ccgcctgaca atcagcaagg acaccagcaa gaaccaggtg      240
gtgctgacca tgaccaacat ggaccccgtg acaccgcca cctactactg cgccaggagg       300
ggcttccacc ttggcagcag gggcgactac ttcgaccact ggggcaagg caccactgtg      360 accgtgagca gcgcttcgac caagggccca tcggtcttcc cctggcacc tcctccaag      420 agcacctctg ggggcacagc ggccctgggc tgcctggtca aggactactt ccccgaaccg      480
gtgacggtgt cgtggaactc aggcgccctg accagcggcg tgcacacctt cccggctgtc      540
ctacagtcct caggactcta ctccctcagc agcgtggtga ccgtgccctc agcagcttg      600 ggcacccaga cctacatctg caacgtgaat cacaagccca gcaacaccaa ggtggacaag      660
aaagttgagc ccaaatcttg tgacaaaact cacacatgcc caccgtgccc agcacctgaa      720
ctcctggggg gaccgtcagt cttcctcttc cccccaaaac ccaaggacac cctcatgatc      780
tcccggaccc ctgaggtcac atgcgtggtg gtggacgtga gccacgaaga ccctgaggtc      840
aagttcaact ggtacgtgga cggcgtggag gtgcataatg ccaagacaaa gccgcgggag      900
gagcagtaca acagcacgta ccgtgtggtc agcgtcctca ccgtcctgca ccaggactgg      960
ctgaatggca aggagtacaa gtgcaaggtc tccaacaaag ccctcccagc ccccatcgag    1020
aaaaccatct ccaaagccaa agggcagccc cgagaaccac aggtgtacac cctgccccca    1080
tcccgggatg agctgaccaa gaaccaggtc agcctgacct gcctggtcaa aggcttctat    1140
cccagcgaca tcgccgtgga gtgggagagc aatgggcagc cggagaacaa ctacaagacc    1200
acgcctcccg tgctggactc cgacggctcc ttcttcctct acagcaagct caccgtggac    1260
aagagcaggt ggcagcaggg gaacgtcttc tcatgctccg tgatgcatga ggctctgcac    1320
aaccactaca cgcagaagag cctctccctg tctccgggta aa                      1362
```

<210> SEQ ID NO 61
<211> LENGTH: 657
<212> TYPE: DNA
<213> ORGANISM: Artificial Sequence
<220> FEATURE:
<221> NAME/KEY: Gene
<223> OTHER INFORMATION: HAB-9001 light chain nucleotide sequence

<400> SEQUENCE: 61

```
gacgtcgtga tgacccagac cccctgagc ctgcccgtga ccccaggaga accgccagc        60
```

```
atcagctgca ggagcagcca gagcatcgtg cacagcaacg gcaacaccta cctggagtgg    120
tacctgcaga agcctggcca aagcccccag ctgctgatat acaaggtgag caacaggttc    180
agcggcgtgc ccgataggtt ctctggcagt ggcagcggga ccgacttcac cctgaagatt    240
agcagagtgg aggccgagga cgtgggcgtg tactactgct tccaaggcag ccgcgtgccc    300
ctgaccttcg gccagggcac taagctggag atcaagcgta cggtggctgc accatctgtc    360
ttcatcttcc cgccatctga tgagcagttg aaatctggaa ctgcctctgt tgtgtgcctg    420
ctgaataact tctatcccag agaggccaaa gtacagtgga aggtggataa cgccctccaa    480
tcgggtaact cccaggagag tgtcacagag caggacagca aggacagcac ctacagcctc    540
agcagcaccc tgacgctgag caaagcagac tacgagaaac acaaagtcta cgcctgcgaa    600
gtcacccatc agggcctgag ctcgcccgtc acaaagagct tcaacagggg agagtgt      657
```

<210> SEQ ID NO 62
<211> LENGTH: 324
<212> TYPE: PRT
<213> ORGANISM: Artificial Sequence
<220> FEATURE:
<221> NAME/KEY: domain
<223> OTHER INFORMATION: mIgG1 heavy chain constant region amino acid
      sequence

<400> SEQUENCE: 62

```
Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Glu Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
```

```
                        245                 250                 255

Glu Trp Gln Trp Asn Gly Gln Pro Ala Glu Asn Tyr Lys Asn Thr Gln
            260                 265                 270

Pro Ile Met Asn Thr Asn Gly Ser Tyr Phe Val Tyr Ser Lys Leu Asn
        275                 280                 285

Val Gln Lys Ser Asn Trp Glu Ala Gly Asn Thr Phe Thr Cys Ser Val
    290                 295                 300

Leu His Glu Gly Leu His Asn His His Thr Glu Lys Ser Leu Ser His
305                 310                 315                 320

Ser Pro Gly Lys

<210> SEQ ID NO 63
<211> LENGTH: 107
<212> TYPE: PRT
<213> ORGANISM: Artificial Sequence
<220> FEATURE:
<221> NAME/KEY: domain
<223> OTHER INFORMATION: mIgG1 light chain constant region amino acid
      sequence

<400> SEQUENCE: 63

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
        35                  40                  45

Gln Asn Gly Val Leu Asn Ser Trp Thr Asp Gln Asp Ser Lys Asp Ser
    50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                85                  90                  95

Pro Ile Val Lys Ser Phe Asn Arg Asn Glu Cys
            100                 105

<210> SEQ ID NO 64
<211> LENGTH: 330
<212> TYPE: PRT
<213> ORGANISM: Artificial Sequence
<220> FEATURE:
<221> NAME/KEY: domain
<223> OTHER INFORMATION: mIgG2a heavy chain constant region amino acid
      sequence

<400> SEQUENCE: 64

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95
```

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
            115                 120                 125

Lys Ile Lys Asp Val Leu Met Ile Ser Leu Ser Pro Ile Val Thr Cys
            130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                    165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
            195                 200                 205

Lys Asp Leu Pro Ala Pro Ile Glu Arg Thr Ile Ser Lys Pro Lys Gly
            210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                    245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
            275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                    325                 330

<210> SEQ ID NO 65
<211> LENGTH: 107
<212> TYPE: PRT
<213> ORGANISM: Artificial Sequence
<220> FEATURE:
<221> NAME/KEY: domain
<223> OTHER INFORMATION: mIgG2a light chain constant region amino acid
      sequence

<400> SEQUENCE: 65

Arg Ala Asp Ala Ala Pro Thr Val Ser Ile Phe Pro Pro Ser Ser Glu
1               5                   10                  15

Gln Leu Thr Ser Gly Gly Ala Ser Val Val Cys Phe Leu Asn Asn Phe
            20                  25                  30

Tyr Pro Lys Asp Ile Asn Val Lys Trp Lys Ile Asp Gly Ser Glu Arg
            35                  40                  45

Gln Asn Gly Val Leu Asn Ser Trp Thr Asp Gln Asp Ser Lys Asp Ser
        50                  55                  60

Thr Tyr Ser Met Ser Ser Thr Leu Thr Leu Thr Lys Asp Glu Tyr Glu
65                  70                  75                  80

Arg His Asn Ser Tyr Thr Cys Glu Ala Thr His Lys Thr Ser Thr Ser
                    85                  90                  95

Pro Ile Val Lys Ser Phe Asn Arg Asn Glu Cys
            100                 105

<210> SEQ ID NO 66
<211> LENGTH: 120
<212> TYPE: PRT
<213> ORGANISM: Artificial Sequence
<220> FEATURE:
<221> NAME/KEY: domain
<223> OTHER INFORMATION: HAB-2401 grafted VH

<400> SEQUENCE: 66

```
Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Asn Thr
            20                  25                  30

Tyr Met His Trp Val Arg Gln Ala Pro Gly Lys Gly Leu Glu Trp Met
        35                  40                  45

Gly Arg Ile Asp Pro Thr Asn Gly Asn Thr Lys Tyr Ala Pro Lys Phe
    50                  55                  60

Lys Asp Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr Arg Val Tyr Tyr Asp Ser Thr Tyr Asn Tyr Trp Gly Lys
            100                 105                 110

Gly Thr Thr Val Thr Val Ser Ser
        115                 120
```

<210> SEQ ID NO 67
<211> LENGTH: 113
<212> TYPE: PRT
<213> ORGANISM: Artificial Sequence
<220> FEATURE:
<221> NAME/KEY: domain
<223> OTHER INFORMATION: HAB-2401 grafted VL

<400> SEQUENCE: 67

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Asn Tyr Leu Thr Trp Tyr Gln Gln Lys Pro Gly Lys
        35                  40                  45

Val Pro Lys Leu Leu Ile Tyr Trp Ala Ser Thr Arg Glu Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp Tyr Asn Tyr Pro Leu Thr Phe Gly Gly Gly Thr Lys Val Glu Ile
            100                 105                 110

Lys
```

<210> SEQ ID NO 68
<211> LENGTH: 121
<212> TYPE: PRT
<213> ORGANISM: Artificial Sequence
<220> FEATURE:
<221> NAME/KEY: domain
<223> OTHER INFORMATION: HAB-3601 grafted VH

<400> SEQUENCE: 68

-continued

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Thr Phe
            20                  25                  30

Gly Met Gly Val Gly Trp Val Arg Gln Ala Pro Gly Lys Gly Leu Glu
        35                  40                  45

Trp Val Ala His Ile Trp Trp Asp Asp Lys Tyr Tyr Asn Pro Ala
50                  55                  60

Leu Lys Ser Arg Phe Thr Ile Ser Arg Asp Asn Ser Lys Asn Thr Leu
65                  70                  75                  80

Tyr Leu Gln Met Asn Ser Leu Arg Ala Glu Asp Thr Ala Val Tyr Tyr
                85                  90                  95

Cys Ala Arg Arg Pro Leu Gly Ser Tyr Asp Tyr Phe Asp Tyr Trp Gly
            100                 105                 110

Lys Gly Thr Thr Val Thr Val Ser Ser
            115                 120

<210> SEQ ID NO 69
<211> LENGTH: 112
<212> TYPE: PRT
<213> ORGANISM: Artificial Sequence
<220> FEATURE:
<221> NAME/KEY: domain
<223> OTHER INFORMATION: HAB-3601 grafted VL

<400> SEQUENCE: 69

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Ile Val His Ser
            20                  25                  30

Asn Gly Asn Thr Tyr Leu Glu Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Phe Gln Gly
                85                  90                  95

Ser Arg Val Pro Leu Thr Phe Gly Gly Gly Thr Lys Val Glu Ile Lys
            100                 105                 110

<210> SEQ ID NO 70
<211> LENGTH: 122
<212> TYPE: PRT
<213> ORGANISM: Artificial Sequence
<220> FEATURE:
<221> NAME/KEY: domain
<223> OTHER INFORMATION: HAB-5101 grafted VH

<400> SEQUENCE: 70

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Val Ser Leu Tyr Asn Pro Ser
50                  55                  60

```
Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Ile Ile Thr Val Val Asp Ala Met Asp Tyr Trp
            100                 105                 110

Gly Gln Gly Thr Thr Val Thr Val Ser Ser
            115                 120
```

<210> SEQ ID NO 71
<211> LENGTH: 112
<212> TYPE: PRT
<213> ORGANISM: Artificial Sequence
<220> FEATURE:
<221> NAME/KEY: domain
<223> OTHER INFORMATION: HAB-5101 grafted VL

<400> SEQUENCE: 71

```
Asp Ile Val Met Thr Gln Thr Pro Leu Ser Leu Pro Val Thr Pro Gly
  1               5                  10                  15

Glu Pro Ala Ser Ile Ser Cys Arg Ser Gln Ser Ile Val His Ser
                 20                  25                  30

Asn Gly Asn Thr Tyr Leu Glu Trp Tyr Leu Gln Lys Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Cys Gln Gly
                 85                  90                  95

Ser Arg Val Pro Pro Thr Phe Gly Gly Gly Thr Lys Val Glu Ile Lys
            100                 105                 110
```

<210> SEQ ID NO 72
<211> LENGTH: 124
<212> TYPE: PRT
<213> ORGANISM: Artificial Sequence
<220> FEATURE:
<221> NAME/KEY: domain
<223> OTHER INFORMATION: HAB-9001 grafted VH

<400> SEQUENCE: 72

```
Gln Val Thr Leu Lys Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Phe
                 20                  25                  30

Gly Met Gly Val Gly Trp Ile Arg Gln Pro Pro Gly Lys Ala Leu Glu
             35                  40                  45

Trp Leu Ala His Ile Trp Trp Asp Asp Lys Tyr Tyr Asn Pro Ala
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Gly Phe His Leu Gly Ser Arg Gly Asp Tyr Phe Asp
            100                 105                 110

His Trp Gly Gln Gly Thr Thr Val Thr Val Ser Ser
            115                 120
```

```
<210> SEQ ID NO 73
<211> LENGTH: 112
<212> TYPE: PRT
<213> ORGANISM: Artificial Sequence
<220> FEATURE:
<221> NAME/KEY: domain
<223> OTHER INFORMATION: HAB-9001 grafted VL

<400> SEQUENCE: 73

Asp Ile Val Met Thr Gln Thr Pro Leu Ser Leu Pro Val Thr Pro Gly
1               5                   10                  15

Glu Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser Arg Val Pro Leu Thr Phe Gly Gln Gly Thr Lys Leu Glu Ile Lys
                100                 105                 110
```